United States Patent
Jung et al.

(10) Patent No.: US 11,680,071 B2
(45) Date of Patent: Jun. 20, 2023

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 429 days.

(21) Appl. No.: 17/055,706

(22) PCT Filed: Jul. 2, 2019

(86) PCT No.: PCT/KR2019/008071
§ 371 (c)(1),
(2) Date: Nov. 16, 2020

(87) PCT Pub. No.: WO2020/009441
PCT Pub. Date: Jan. 9, 2020

(65) Prior Publication Data
US 2021/0214369 A1    Jul. 15, 2021

(30) Foreign Application Priority Data

Jul. 3, 2018   (KR) .................. 10-2018-0077238
Jun. 28, 2019  (KR) .................. 10-2019-0078376

(51) Int. Cl.
*C07D 495/04*     (2006.01)
*C07D 497/04*     (2006.01)
(Continued)

(52) U.S. Cl.
CPC ......... *C07D 495/04* (2013.01); *C07D 519/00* (2013.01); *H10K 85/615* (2023.02);
(Continued)

(58) Field of Classification Search
CPC .. C07D 495/04; C07D 497/04; H10K 85/654; H10K 85/657; H10K 85/6572; H10K 85/6576; H10K 50/12
See application file for complete search history.

(56) References Cited

U.S. PATENT DOCUMENTS

2004/0251816 A1   12/2004   Leo et al.
2017/0222160 A1   8/2017    Lee et al.

FOREIGN PATENT DOCUMENTS

EP   2301921 A1   3/2011
EP   2301926 A1   3/2011
(Continued)

OTHER PUBLICATIONS

English-language translation of KR-20170093061-A.*

*Primary Examiner* — Vu A Nguyen
(74) *Attorney, Agent, or Firm* — Dentons US LLP

(57) ABSTRACT

Provided is a compound of Chemical Formula 1:

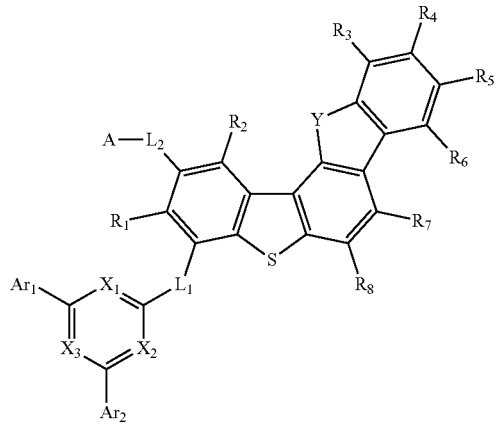

wherein:
$X_1$ to $X_3$ are each independently N or CH, provided that at least two of $X_1$ to $X_3$ are N,
Y is O or S,
$L_1$ and $L_2$ are each independently a single bond, or a substituted or unsubstituted $C_{6-60}$ arylene or $C_{2-60}$ heteroarylene containing one or more of O, N, Si, or S, and
A is Chemical Formula 2 or 3, (Continued)

Chemical Formula 2

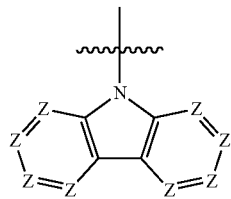

Chemical Formula 3

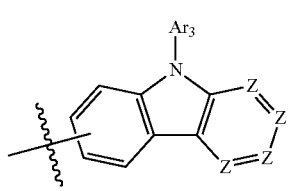

each Z is independently CR, or two adjacent Zs are C each linked to the following Chemical Formula 4 at * to form a fused ring, and the rest are each independently CR:

Chemical Formula 4

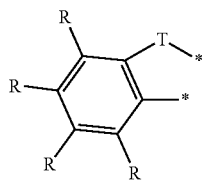

T is O, S, $CQ_1Q_2$, or $NAr_4$, and
$Ar_1$ to $Ar_4$ are each independently a substituted or unsubstituted $C_{6-60}$ aryl or $C_{2-60}$ heteroaryl containing one or more of N, O, or S,
and an organic light emitting device including the same.

10 Claims, 1 Drawing Sheet

(51) Int. Cl.
*H01L 51/00* (2006.01)
*H01L 51/50* (2006.01)
*C07D 519/00* (2006.01)
*H10K 85/60* (2023.01)

(52) U.S. Cl.
CPC ....... *H10K 85/654* (2023.02); *H10K 85/6572* (2023.02); *H10K 85/6574* (2023.02); *H10K 85/6576* (2023.02)

(56) References Cited

FOREIGN PATENT DOCUMENTS

| | | | |
|---|---|---|---|
| JP | 2015-019018 | 1/2015 | |
| JP | 2015-019019 | 1/2015 | |
| KR | 10-2000-0051826 | 8/2000 | |
| KR | 10-2011-0018340 | 2/2011 | |
| KR | 10-2012-0120886 | 11/2012 | |
| KR | 10-1340241 | 12/2013 | |
| KR | 10-2017-0093061 | 8/2017 | |
| KR | 20170093061 A * | 8/2017 | ............. C09K 11/06 |
| WO | 2003-012890 | 2/2003 | |
| WO | 2009-148015 | 12/2009 | |
| WO | 2009-148062 | 12/2009 | |

* cited by examiner

【FIG. 1】
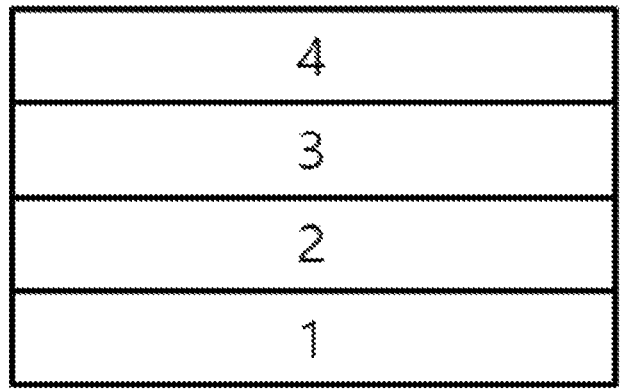
【FIG. 2】
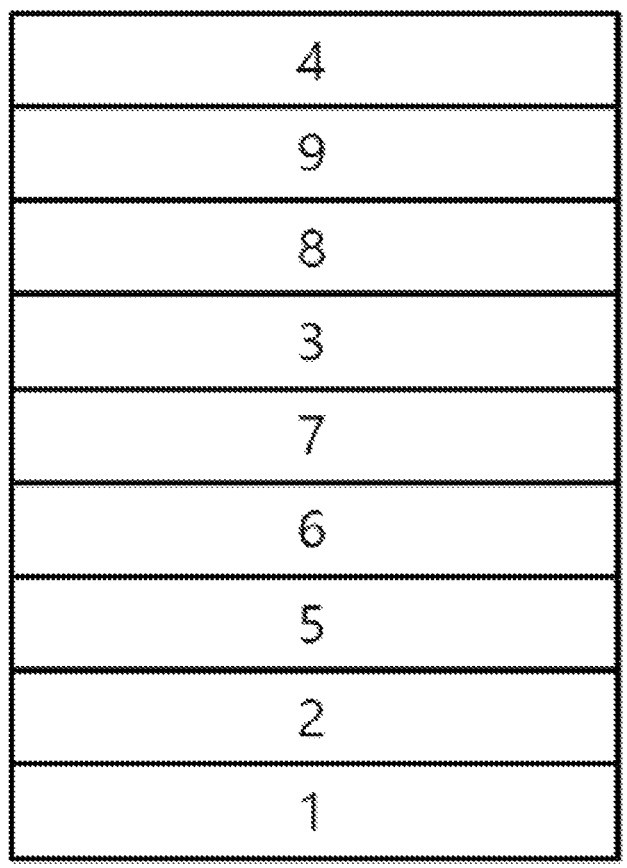

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/008071 filed on Jul. 2, 2019, which claims the benefits of the filing dates of Korean Patent Application No. 10-2018-0077238 filed with the Korean Intellectual Property Office on Jul. 3, 2018, and Korean Patent Application No. 10-2019-0078376 filed with the Korean Intellectual Property Office on Jun. 28, 2019, the entire contents of which are incorporated herein by reference.

FIELD OF THE INVENTION

The present invention relates to a novel compound and to an organic light emitting device including the same.

BACKGROUND

In general, an organic light emitting phenomenon refers to a phenomenon where electrical energy is converted into light energy by using an organic material.

The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode.

The organic material layer frequently has a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like.

In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 1) Korean Patent Laid-open Publication No. 10-2000-0051826

SUMMARY OF THE INVENTION

It is an object of the present invention to provide a novel compound and an organic light emitting device including the same.

In one aspect of the invention, provided is a compound of Chemical Formula 1:

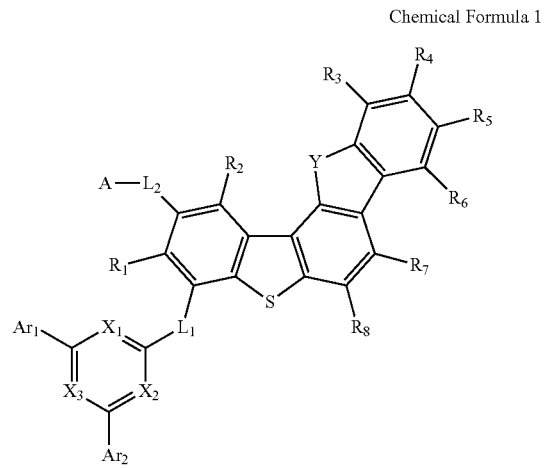

Chemical Formula 1 wherein, in Chemical Formula 1:

$X_1$ to $X_3$ are each independently N or CH, provided that at least two of $X_1$ to $X_3$ are N;

Y is O or S;

$L_1$ and $L_2$ are each independently a single bond, a substituted or unsubstituted $C_{6-60}$ arylene, or a substituted or unsubstituted $C_{2-60}$ heteroarylene containing one or more heteroatoms selected from the group consisting of O, N, Si, and S; and A is one of Chemical Formula 2 or 3:

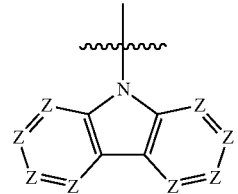

Chemical Formula 2

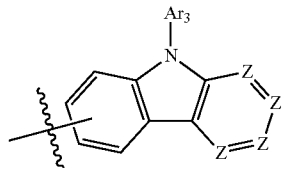

Chemical Formula 3 wherein, in Chemical Formulae 2 and 3:

each Z is independently CR; or two adjacent Zs are C that are linked to the following Chemical Formula 4 to form a fused ring, and the rest are each independently CR:

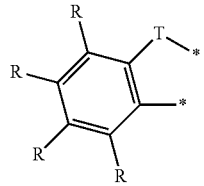

Chemical Formula 4 wherein, in Chemical Formula 4:

T is O, S, $CQ_1Q_2$, or $NAr_4$;

$Ar_1$ to $Ar_4$ are each independently a substituted or unsubstituted $C_{6-60}$ aryl, or a substituted or unsubstituted $C_{2-60}$ heteroaryl containing one or more selected from the group consisting of N, O, and S;

R and $R_1$ to $R_8$ are each independently hydrogen, deuterium, a halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{2-60}$ heteroaryl containing one or more heteroatoms selected from the group consisting of N, O, and S;

$Q_1$ and $Q_2$ are each independently hydrogen, deuterium, a halogen, cyano, nitro, amino, a substituted or unsubstituted $C_{1-60}$ alkyl, or a substituted or unsubstituted $C_{6-60}$ aryl, and

* indicates a point which is attached to two adjacent Z of Chemical Formula 2 or 3.

In another aspect of the invention, there is provided an organic light emitting device including: a first electrode; a second electrode provided opposite to the first electrode; and one or more organic material layers provided between the first electrode and the second electrode, wherein one or more layers of the organic material layers includes the compound of Chemical Formula 1.

The compound of Chemical Formula 1 described above can be used as a material of an organic material layer of an organic light emitting device, and can improve efficiency, achieve a low driving voltage, and/or improve lifetime characteristics in the organic light emitting device.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION

Hereinafter, the present invention will be described in more detail to help understanding of the present invention.

As used herein, the notation

means a bond linked to another substituent group, and the single bond means that there is no separate atom at a part represented as $L_1$ and $L_2$.

As used herein, the term "substituted or unsubstituted" means being unsubstituted or substituted with one or more substituents selected from the group consisting of deuterium, a halogen group, a cyano group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O, and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae, but is not limited thereto:

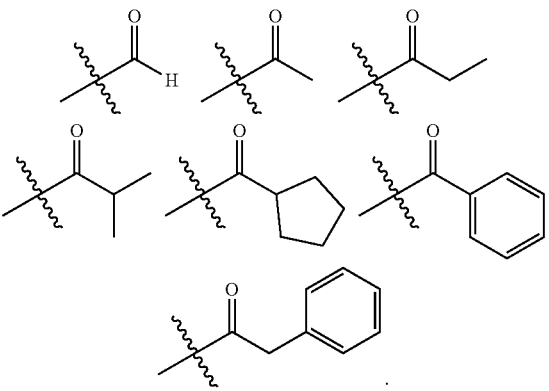

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

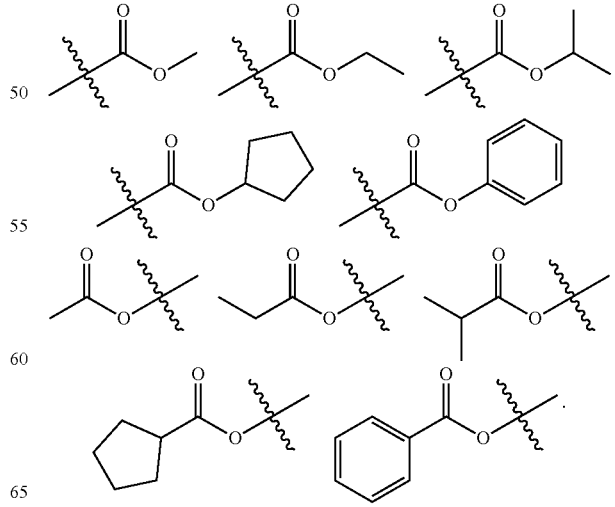

In the present specification, the number of carbon atoms of an imide group is not particularly limited, but is preferably 1 to 25. Specifically, the imide group can be a compound having the following structural formulae, but is not limited thereto:

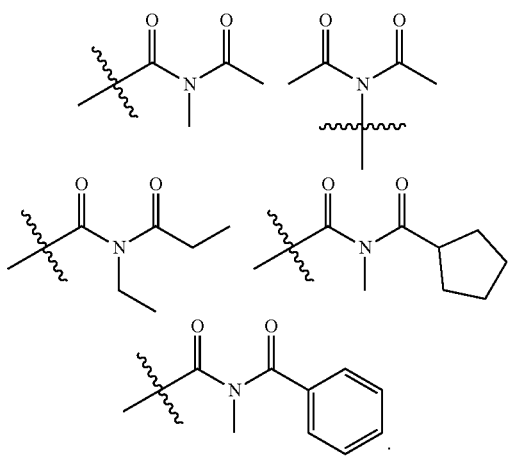

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, and iodine.

In the present specification, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40.

According to one embodiment, the number of carbon atoms of the alkenyl group is 2 to 20.

According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methyl-cyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20.

The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, or the like, but are not limited thereto.

In the present specification, a fluorenyl group can be substituted, and two substituent groups can be bonded to each other to form a spiro structure. In the case where the fluorenyl group is substituted,

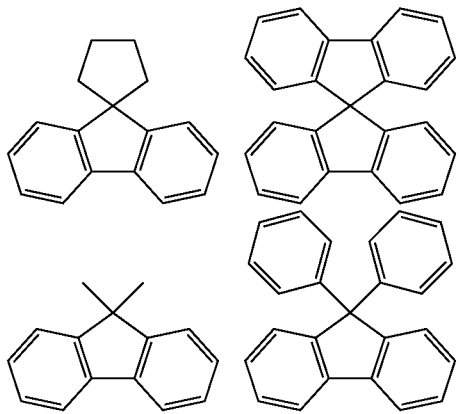

and the like can be formed. However, the structure is not limited thereto.

In the present specification, a heteroaryl is a heteroaryl including one or more of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heteroaryl group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heteroaryl group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heteroaryl group can be applied, except that the heterocycle is not a monovalent group but is formed by combining two substituent groups.

Meanwhile, according to the invention, there is provided a compound of Chemical Formula 1 described above.

In Chemical Formula 1:

$X_1$ to $X_3$ can be N; or $X_1$ and $X_2$ can be N, and $X_3$ can be CH; or $X_1$ and $X_3$ can be N, and $X_2$ can be CH.

In addition, $L_1$ and $L_2$ can each independently be a single bond, or a substituted or unsubstituted phenylene, a substituted or unsubstituted biphenylene, a substituted or unsubstituted naphthylene, a substituted or unsubstituted phenanthrenylene, a substituted or unsubstituted anthracenylene, a substituted or unsubstituted fluoranthenylene, a substituted or unsubstituted triphenylenylene, a substituted or unsubstituted pyrenylene, a substituted or unsubstituted carbazolylene, a substituted or unsubstituted fluorenylene, or a substituted or unsubstituted spiro-fluorenylene.

For example, $L_1$ and $L_2$ can each independently be a single bond, phenylene, or biphenylylene.

At this time, at least one of $L_1$ and $L_2$ can be a single bond.

Further, $Ar_1$ and $Ar_2$ can each independently be a substituted or unsubstituted $C_{6-20}$ aryl, or a substituted or unsubstituted $C_{2-20}$ heteroaryl containing one heteroatom selected from the group consisting of O, N, and S.

For example, $Ar_1$ and $Ar_2$ can each independently be phenyl, biphenylyl, terphenylyl, naphthyl, phenanthrenyl, dibenzothiophenyl, or carbazolyl.

Alternatively, $Ar_1$ and $Ar_2$ can both be phenyl.

Further, in Chemical Formula 1, A can have a structure of Chemical Formula 2 or 3, or can have a structure in which Chemical Formula 2 or 3 is condensed with Chemical Formula 4, respectively. Such A can specifically be one of the following Chemical Formulas 4a to 4n:

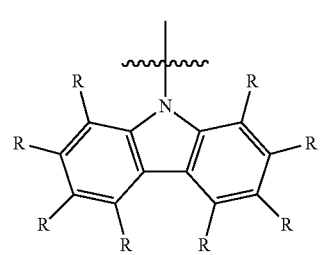

4a

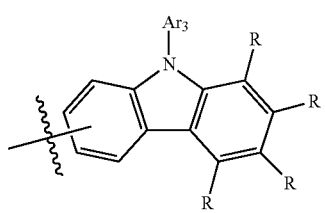

4b

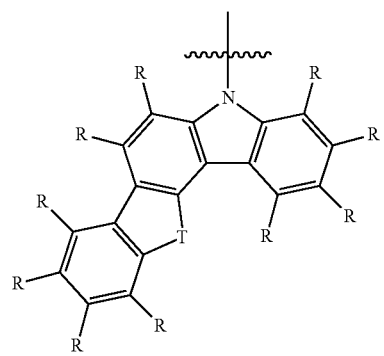

4c

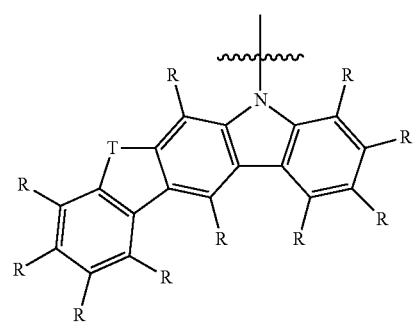

4d

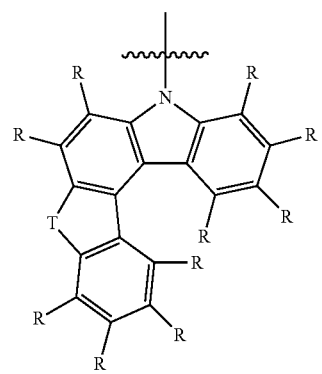

4e

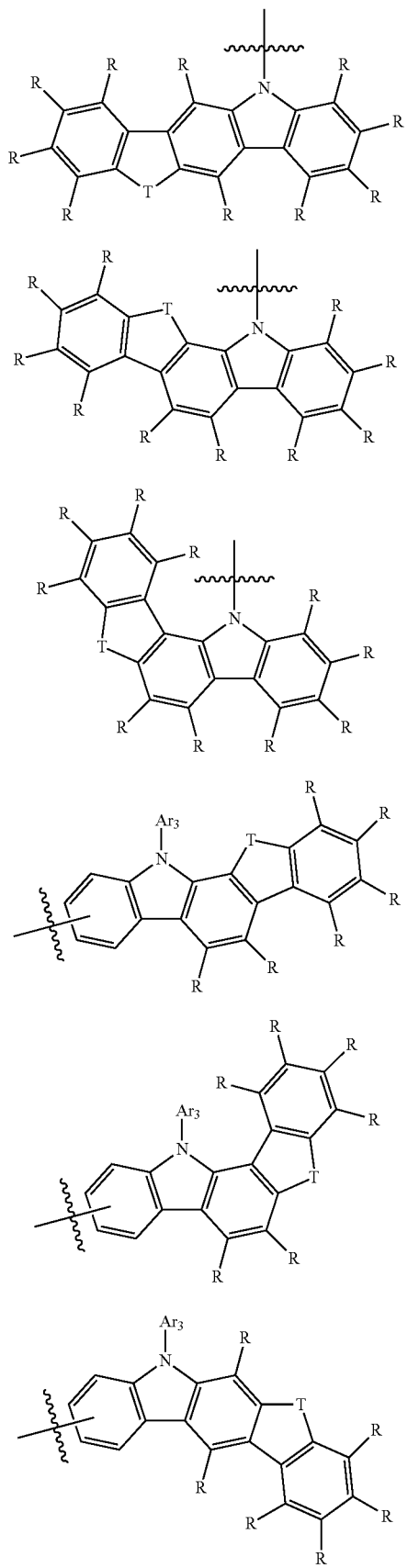
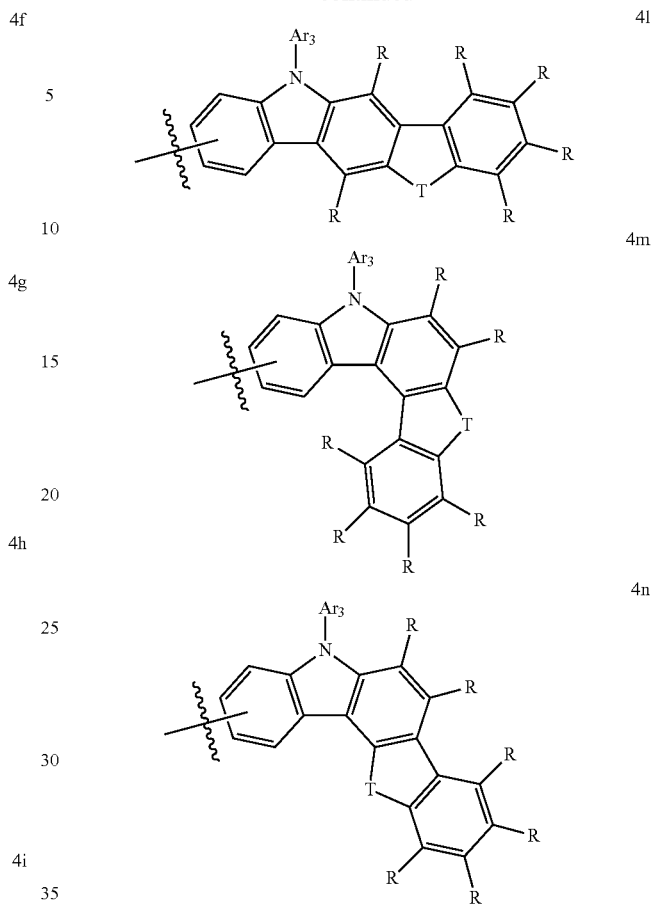

wherein, in Chemical Formulas 4a to 4n:

T, Ar$_3$, and R are the same as those defined in Chemical Formula 1, and each substituent R in the Chemical Formula can be the same as or different from each other.

For example, in Chemical Formulas 4a to 4n:

T is O, S, CQ$_1$Q$_2$, or NAr$_4$;

Ar$_3$ and Ar$_4$ are each independently a C$_{6-20}$ aryl;

each R is independently hydrogen or a C$_{6-20}$ aryl; and

Q$_1$ and Q$_2$ can each independently be hydrogen, a C$_{1-10}$ alkyl, or a C$_{6-20}$ aryl.

Specifically, for example, in Chemical Formulas 4a to 4n, Ar$_3$ and Ar$_4$ are phenyl, each R can independently be hydrogen or phenyl, and Q$_1$ and Q$_2$ can be methyl, but are not limited thereto.

Alternatively, A can be any one of the following Chemical Formulas 5a to 5l:

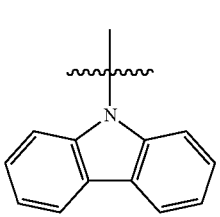

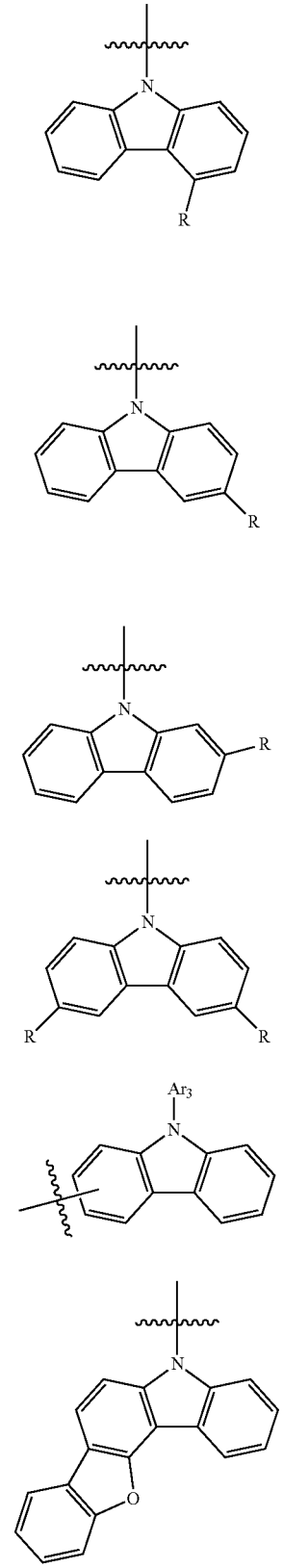
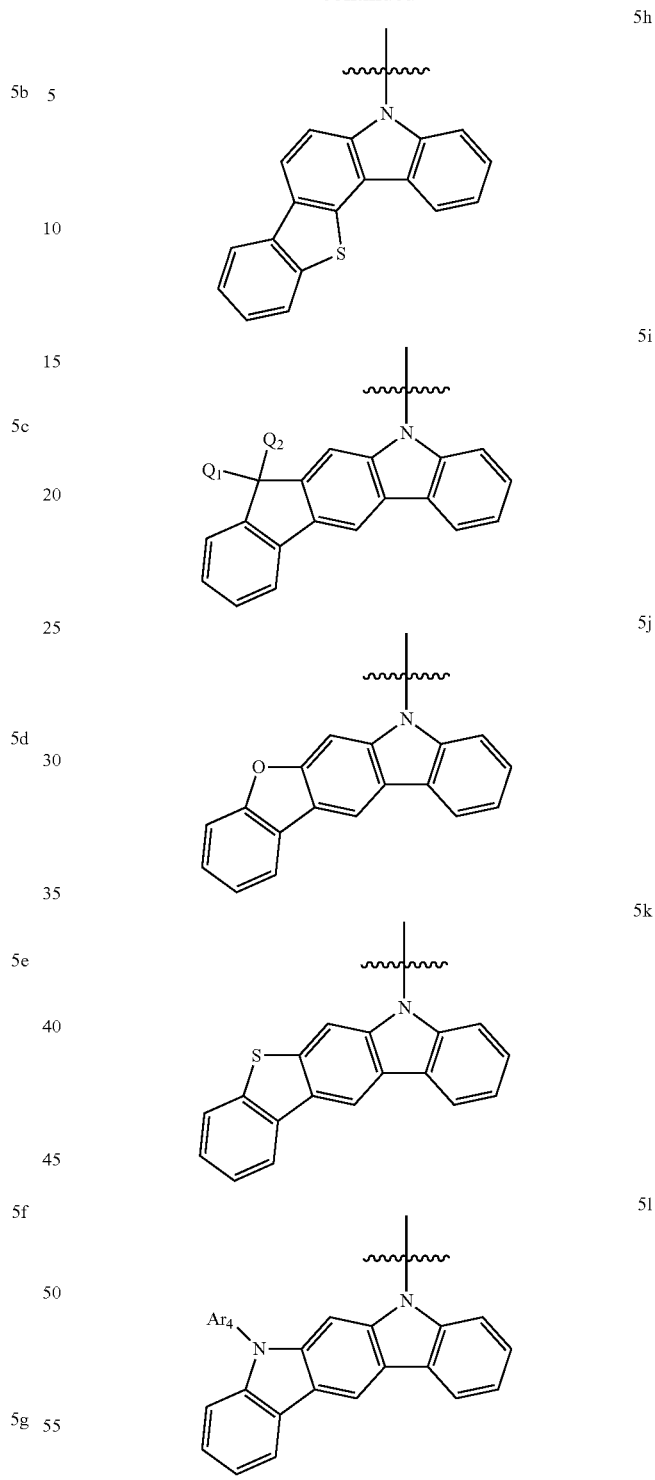

wherein, in Chemical Formulas 5a to 5l:
R, $Ar_3$, $Ar_4$, $Q_1$, and $Q_2$ are the same as those defined in Chemical Formula 1.

For example, in Chemical Formulas 5a to 5l:
R, $Ar_3$, and $Ar_4$ are each independently a $C_{6-20}$ aryl; and $Q_1$ and $Q_2$ can be each independently a $C_{1-10}$ alkyl.

Specifically, for example, in Chemical Formulas 5a to 5l, R, $Ar_3$, and $Ar_4$ can be phenyl, and $Q_1$ and $Q_2$ can be methyl, but are not limited thereto.

Further, $R_1$ to $R_8$ are each independently hydrogen, deuterium, a halogen, cyano, nitro, amino, a $C_{1-20}$ alkyl, or a $C_{6-20}$ aryl.

Specifically, $R_1$ to $R_8$ can all be hydrogen, but are not limited thereto.

In addition, the above-mentioned compound can be any one of the following Chemical Formulas 1-1 to 1-3:

Chemical Formula 1-1

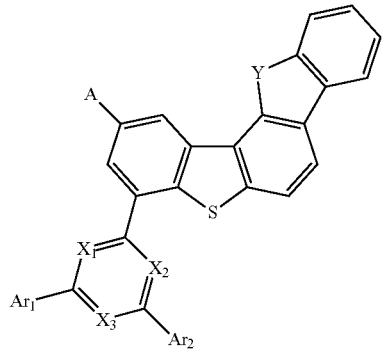

Chemical Formula 1-2

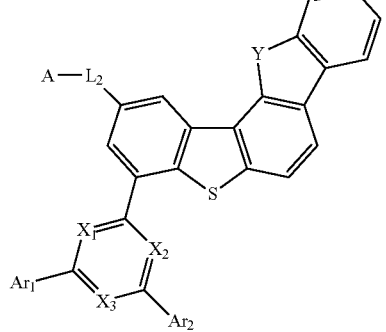

Chemical Formula 1-3

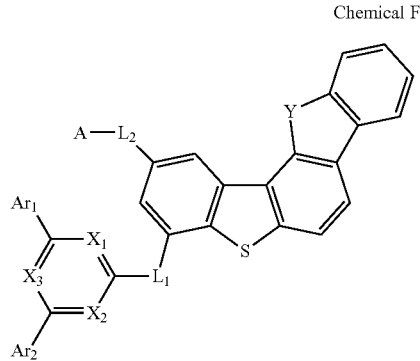

wherein, in Chemical Formulas 1-1 to 1-3:

$X_1$ to $X_3$, Y, $L_1$, $L_2$, A, $Ar_1$, and $Ar_2$ are the same as those defined in Chemical Formula 1 above.

For example, the above-mentioned compound can be any one compound selected from the group consisting of the following compounds:

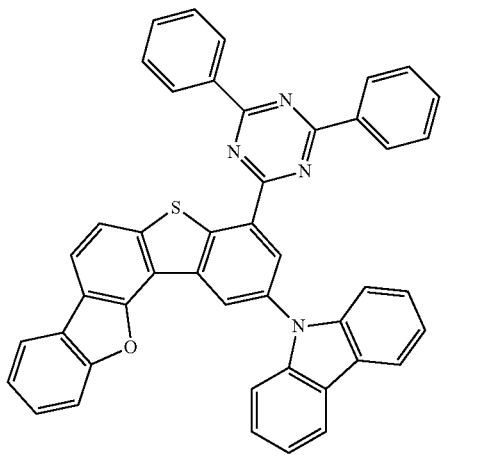

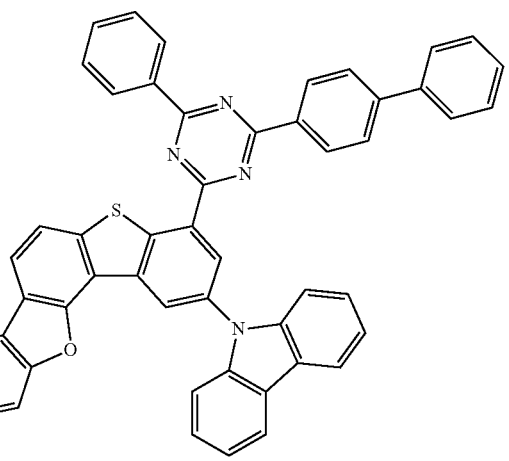

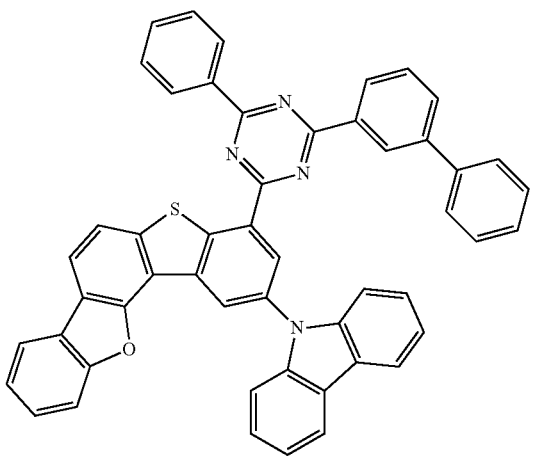

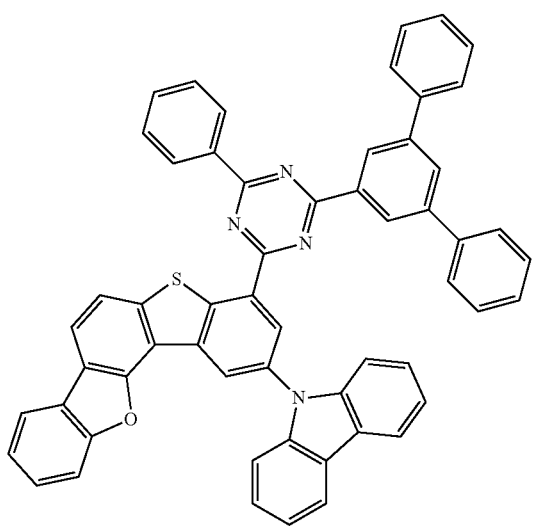
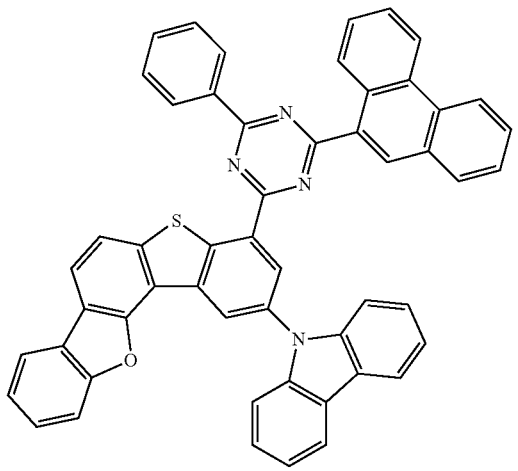
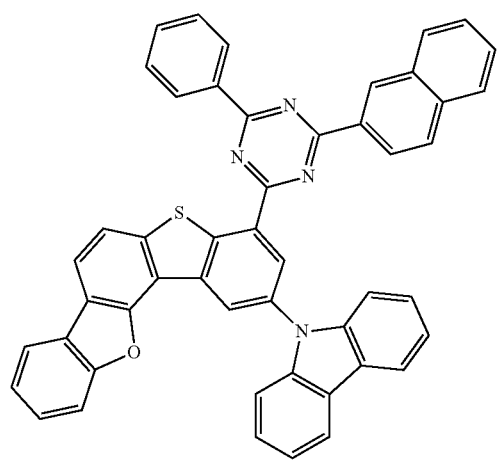
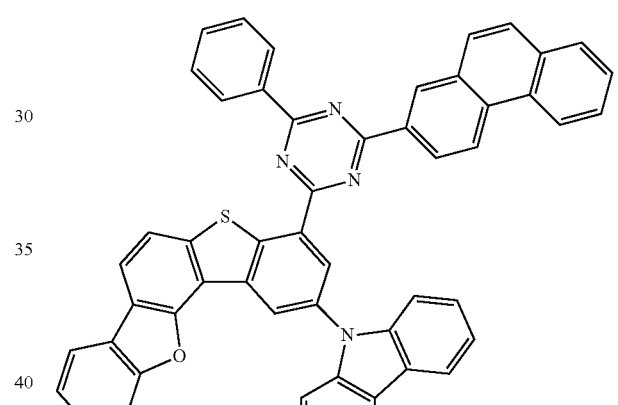
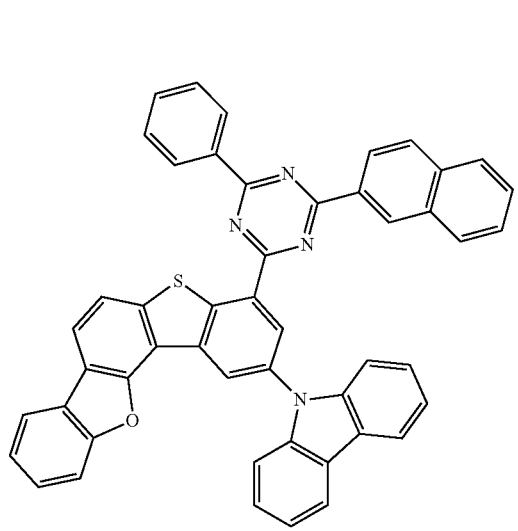
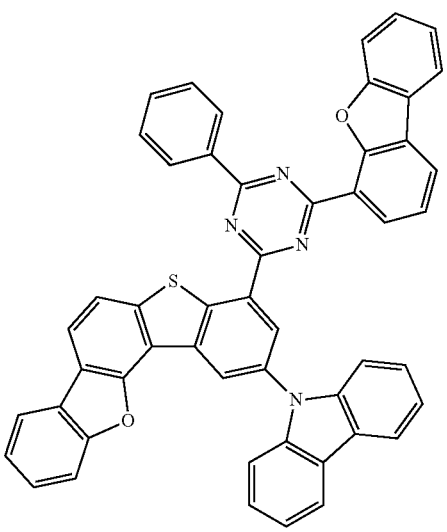

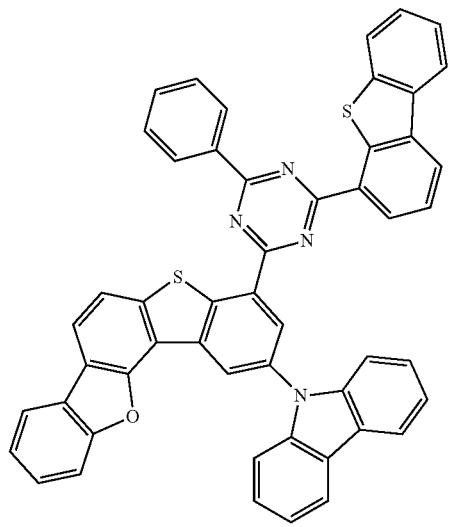
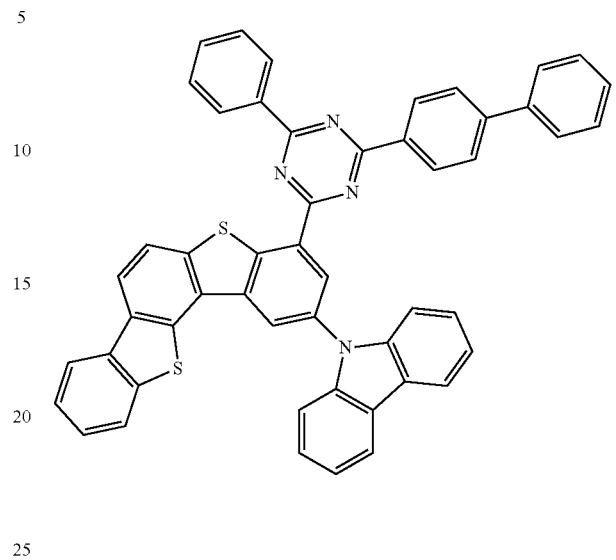
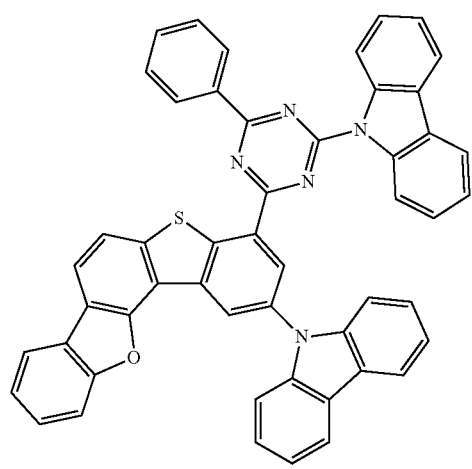
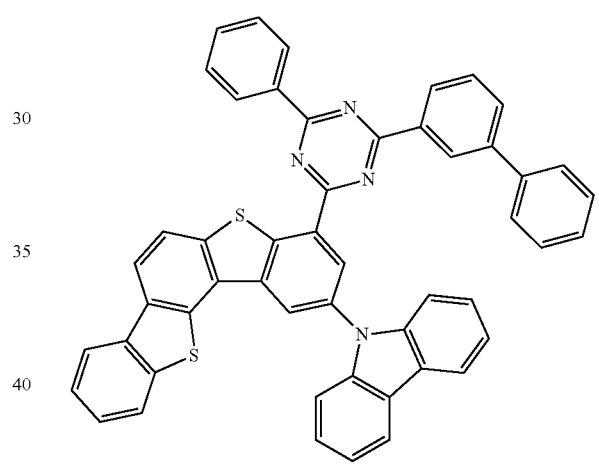
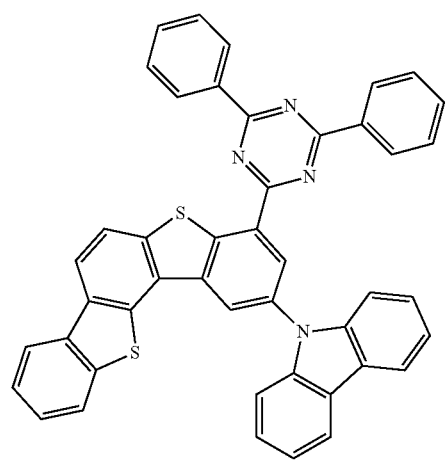
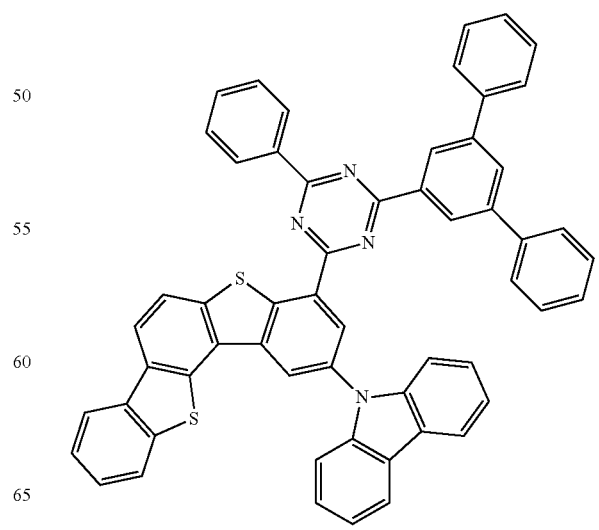

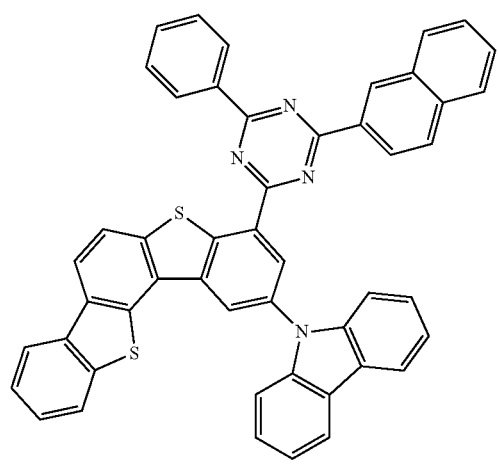
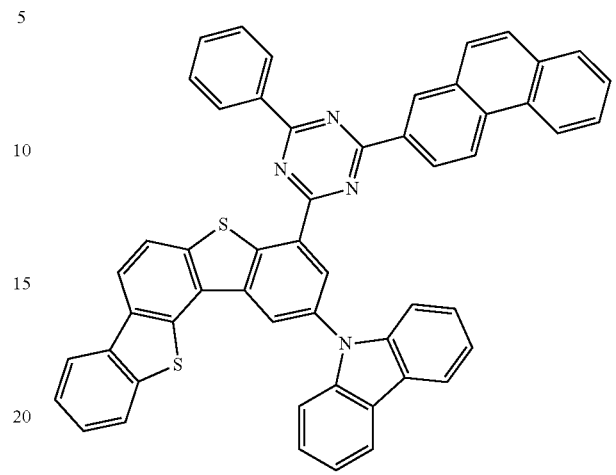
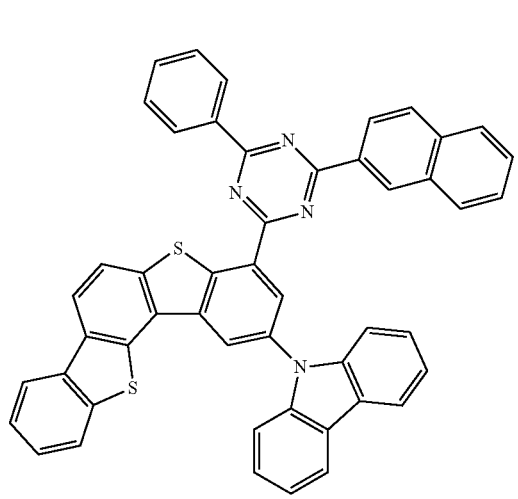
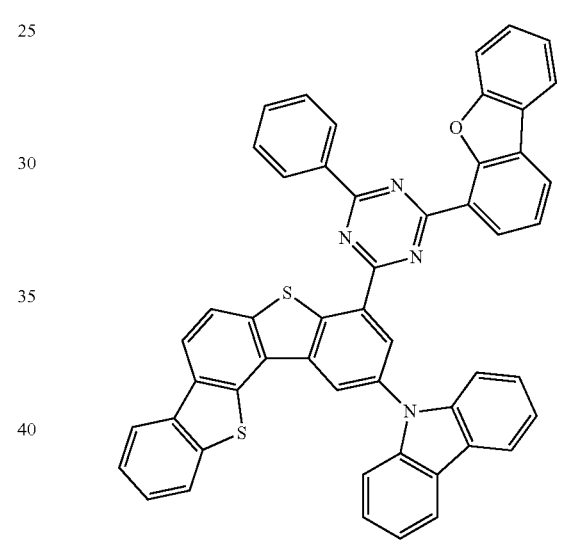
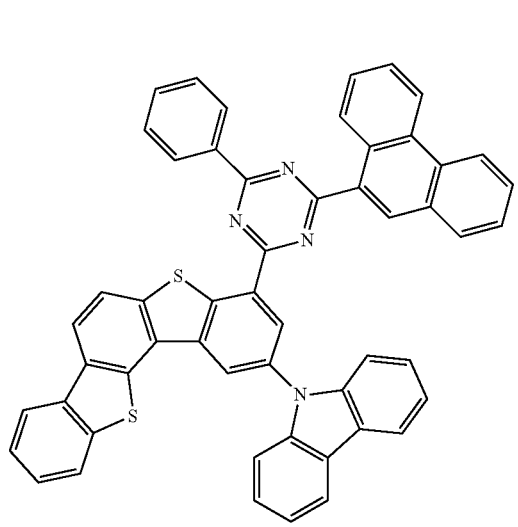
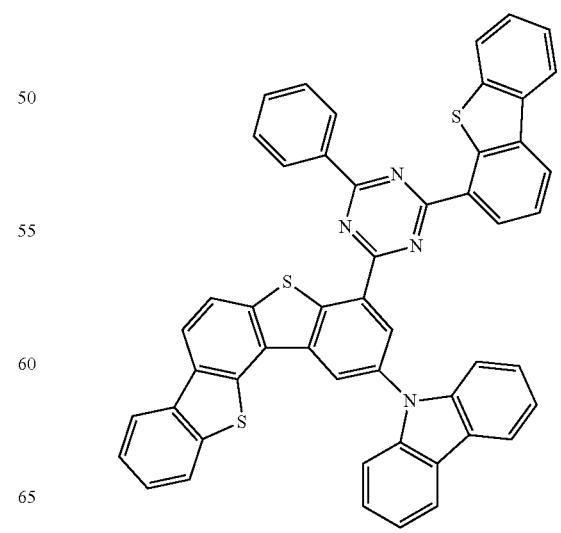

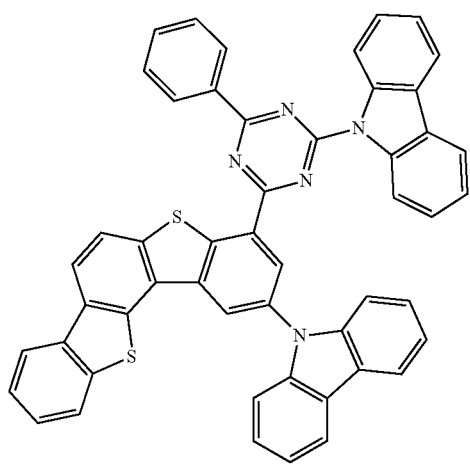
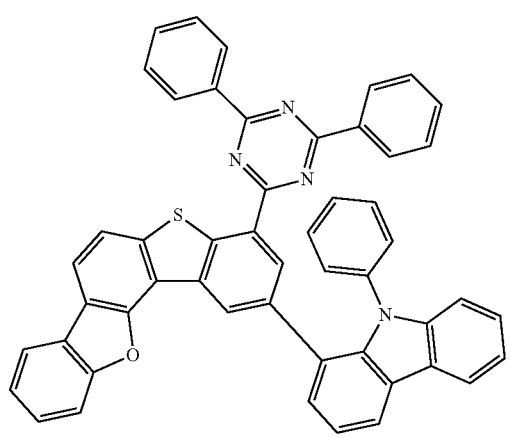
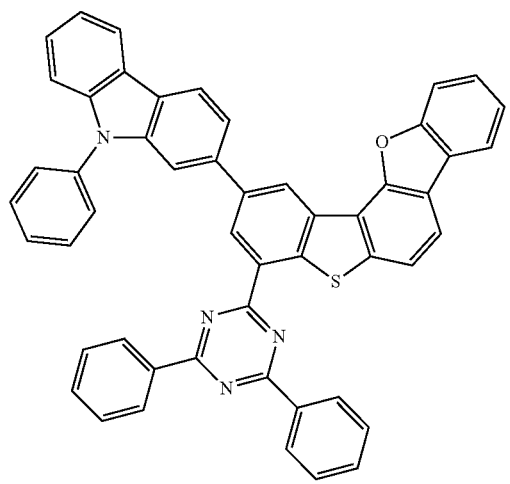
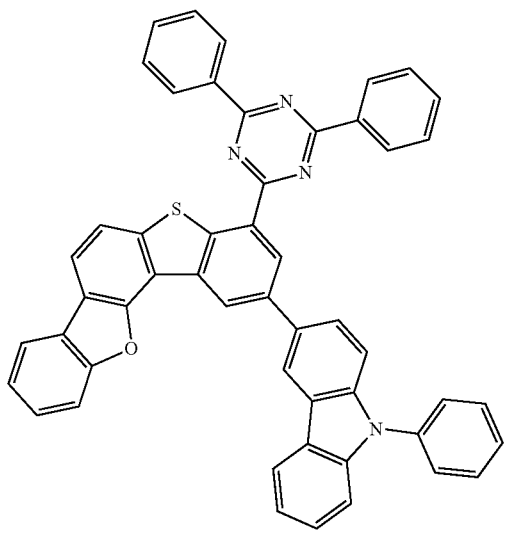
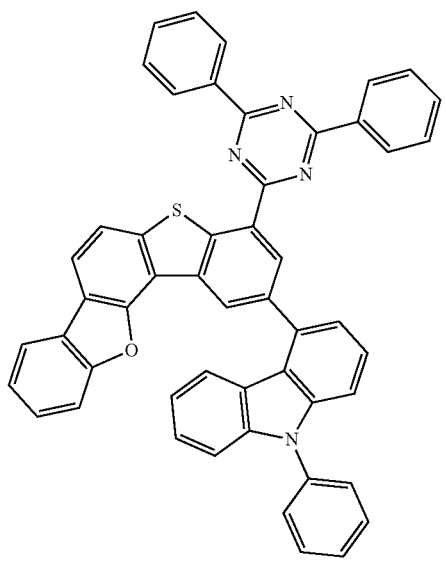
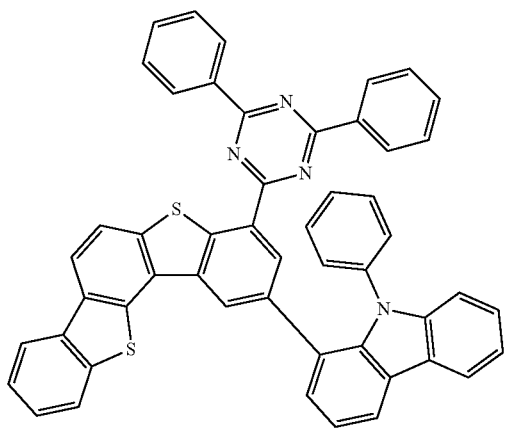

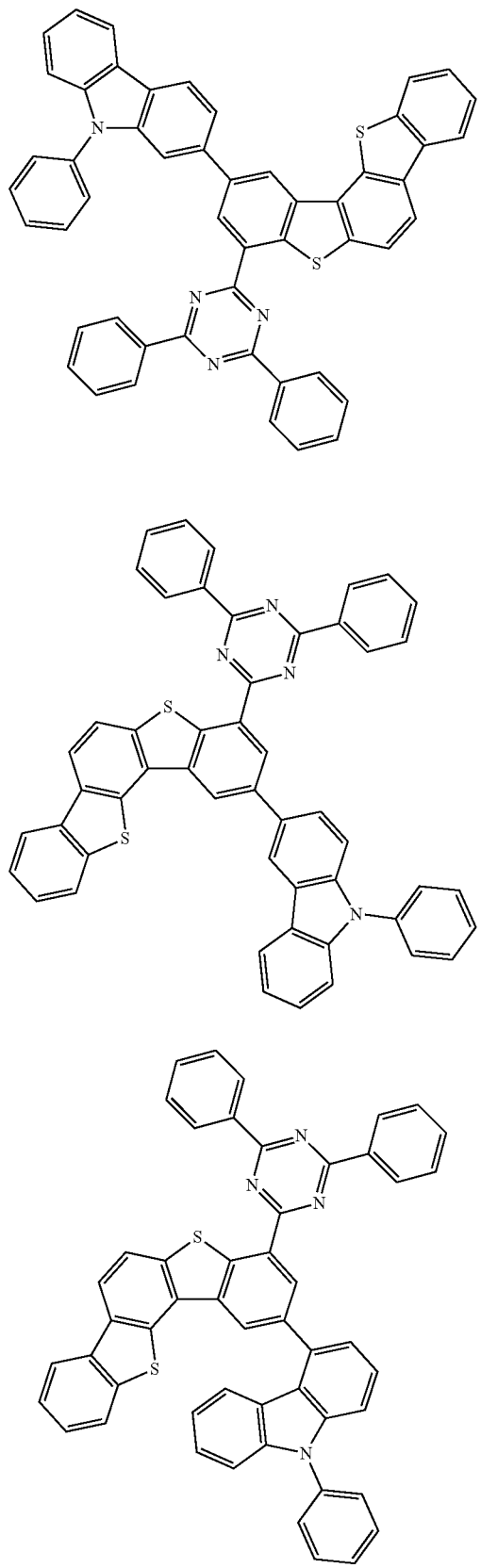 [SMILES: c1ccc(-c2nc(-c3ccccc3)nc(-c3cc(-c4ccc5c6ccccc6n(-c6ccccc6)c5c4)cc4c3sc3ccc5c6ccccc6sc5c34)n2)cc1 ; c1ccc(-c2nc(-c3ccccc3)nc(-c3cc(-c4ccc5c(c4)c4ccccc4n5-c4ccccc4)cc4c3sc3ccc5c6ccccc6sc5c34)n2)cc1 ; c1ccc(-c2nc(-c3ccccc3)nc(-c3cc(-c4cccc5c4c4ccccc4n5-c4ccccc4)cc4c3sc3ccc5c6ccccc6sc5c34)n2)cc1]
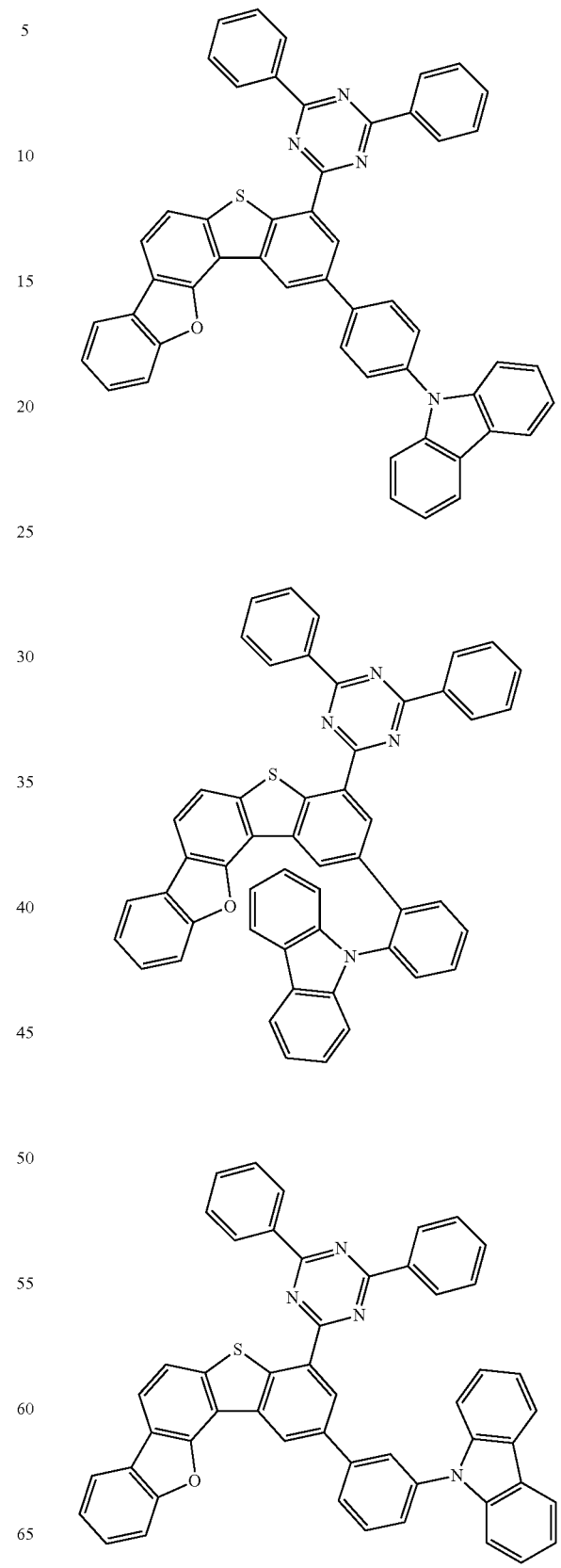

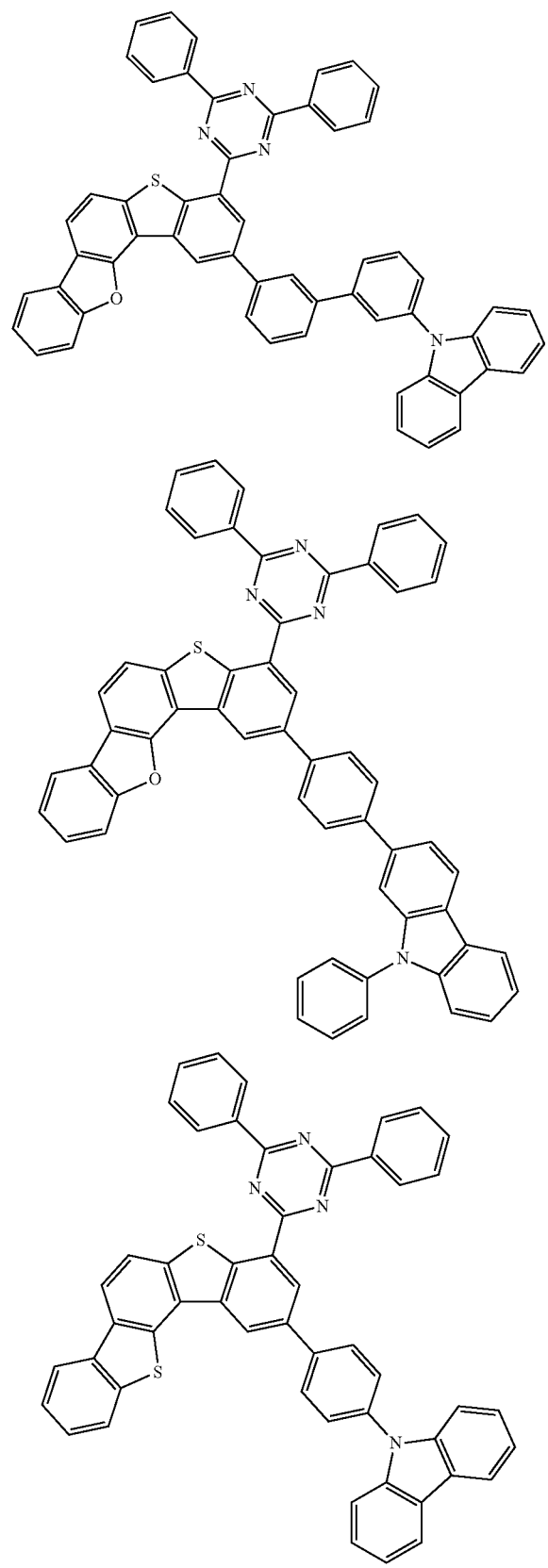
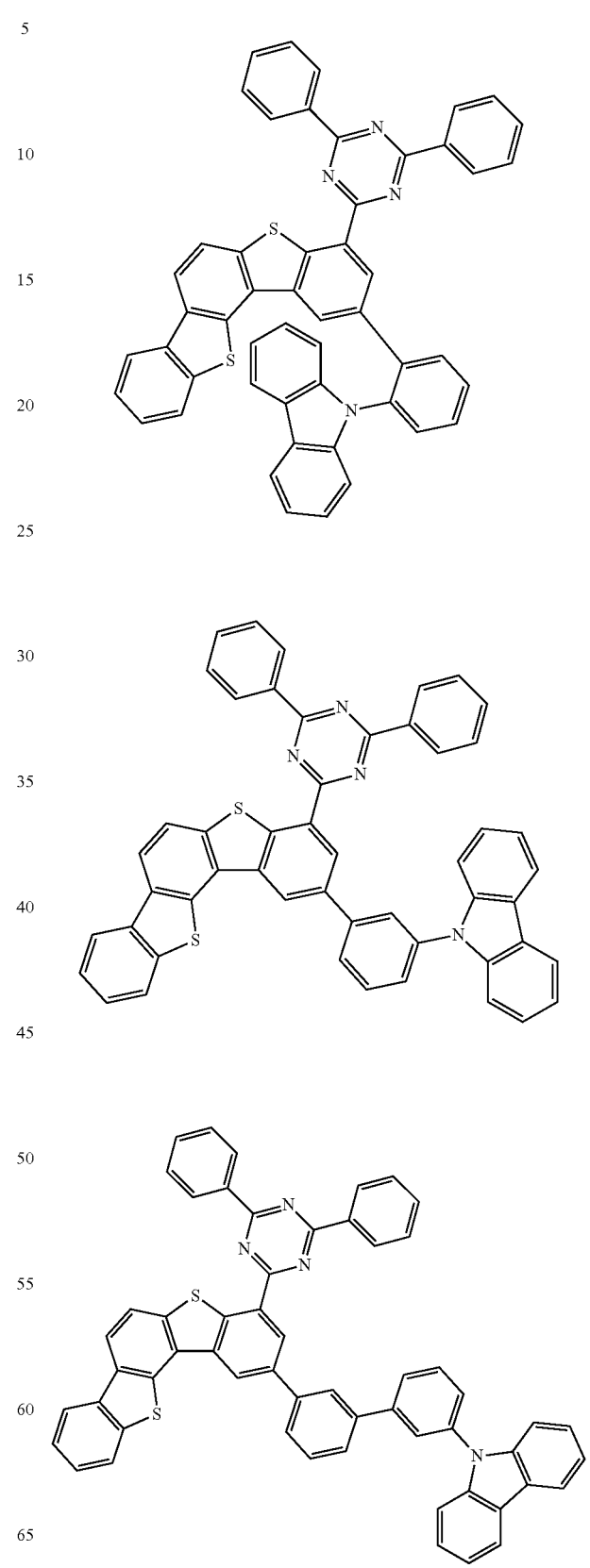

-continued
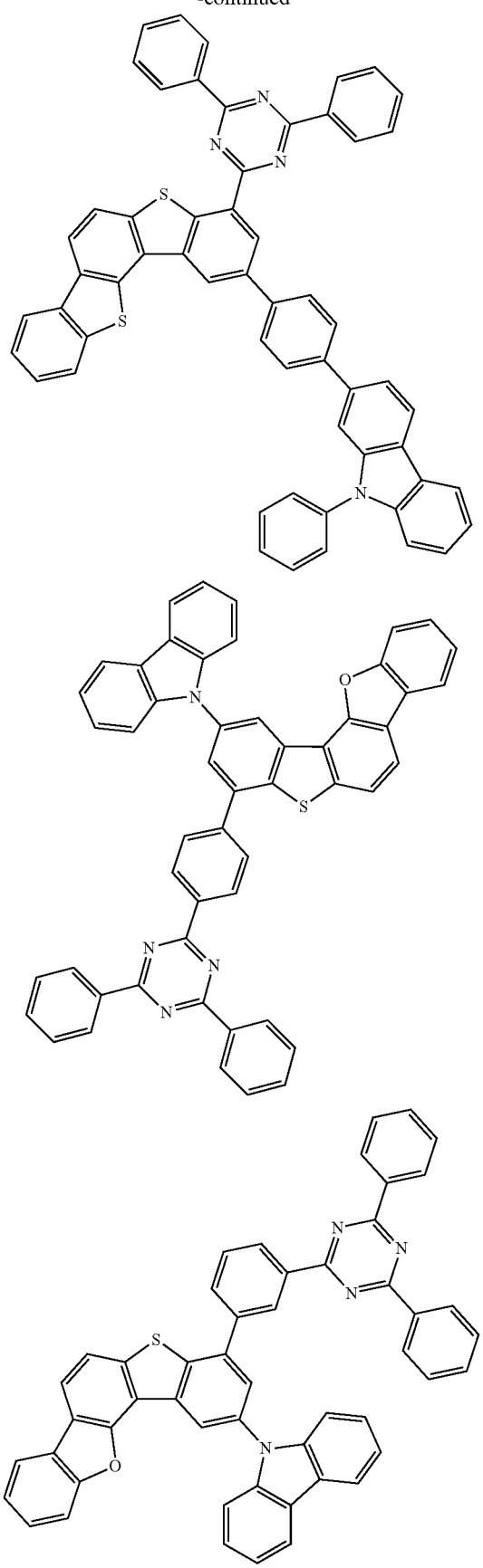
-continued
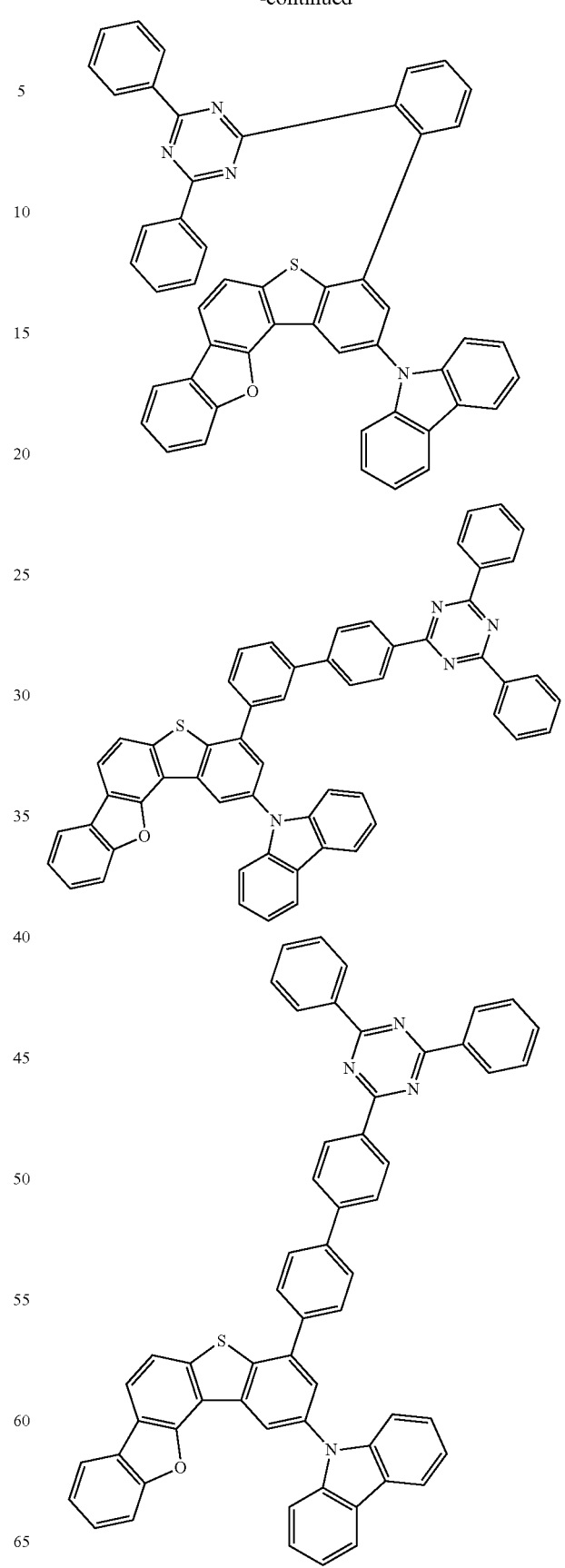

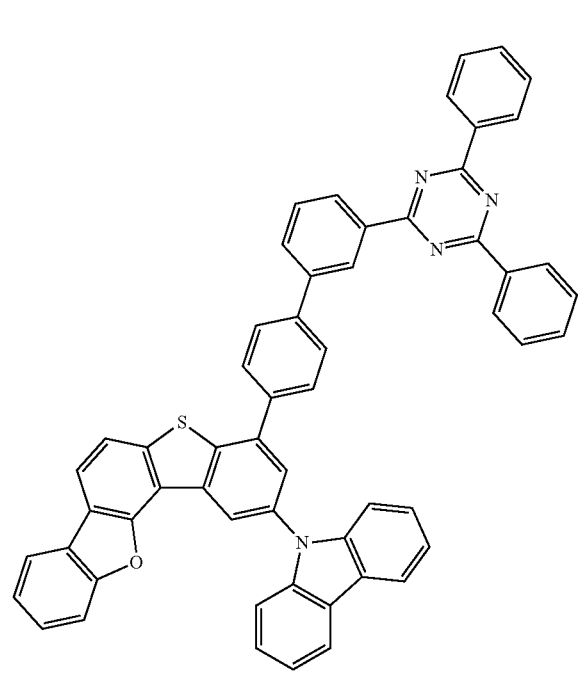
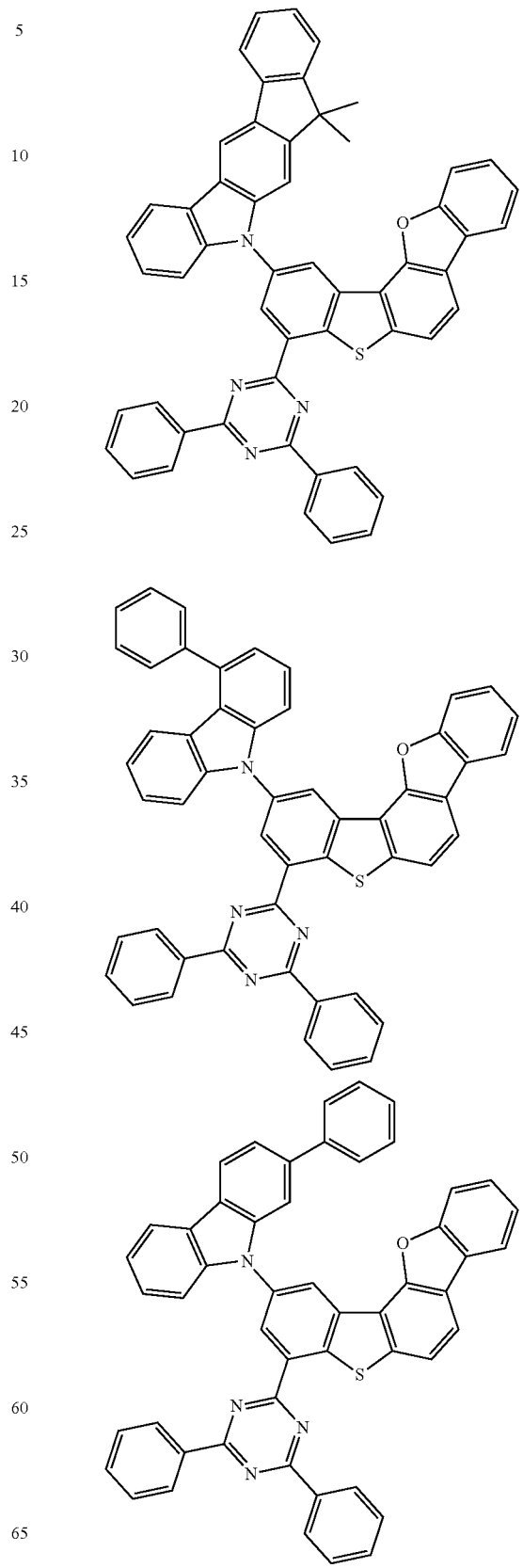

31
-continued
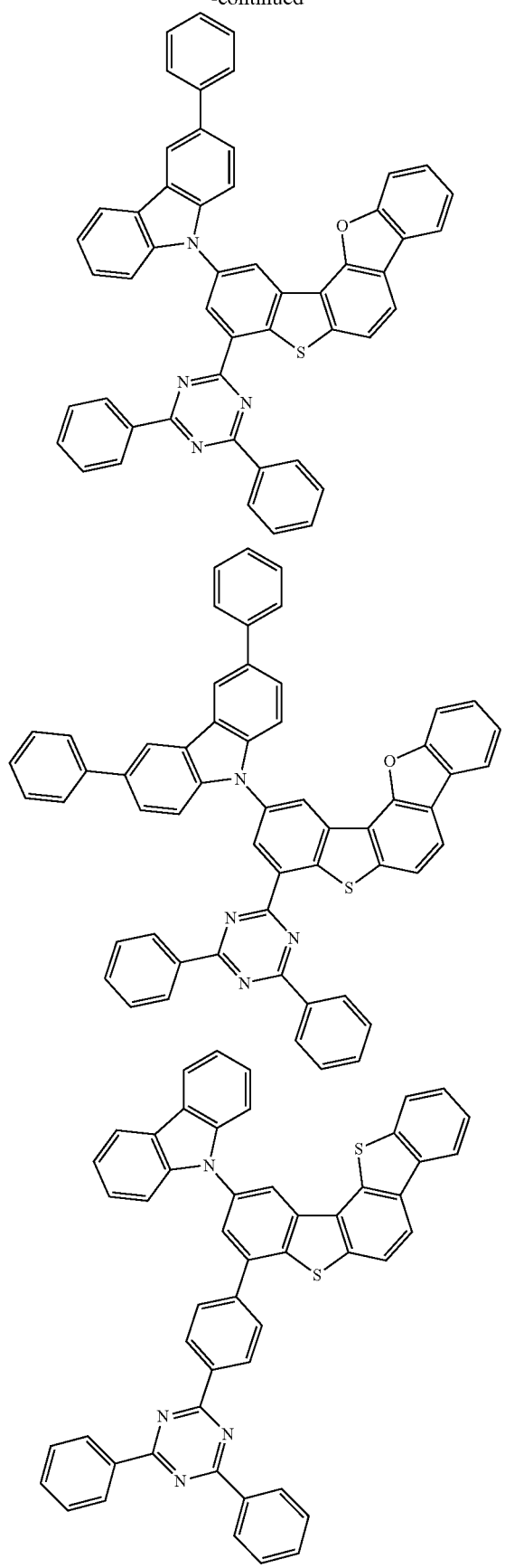
32
-continued
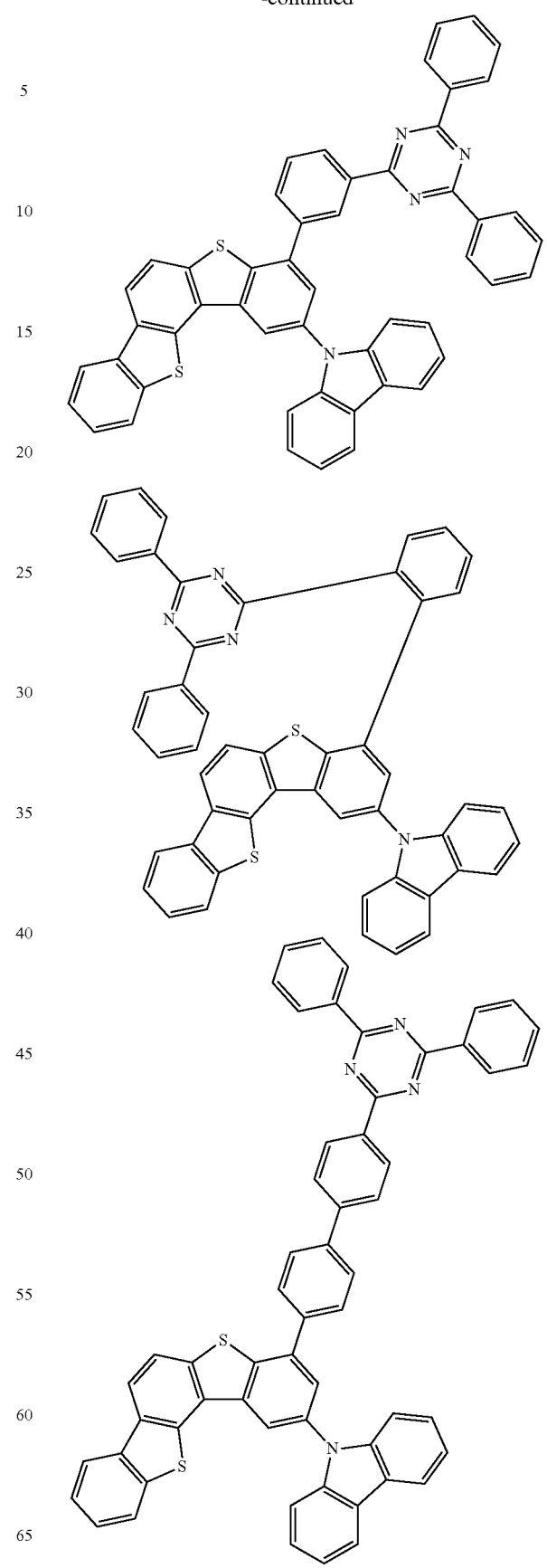

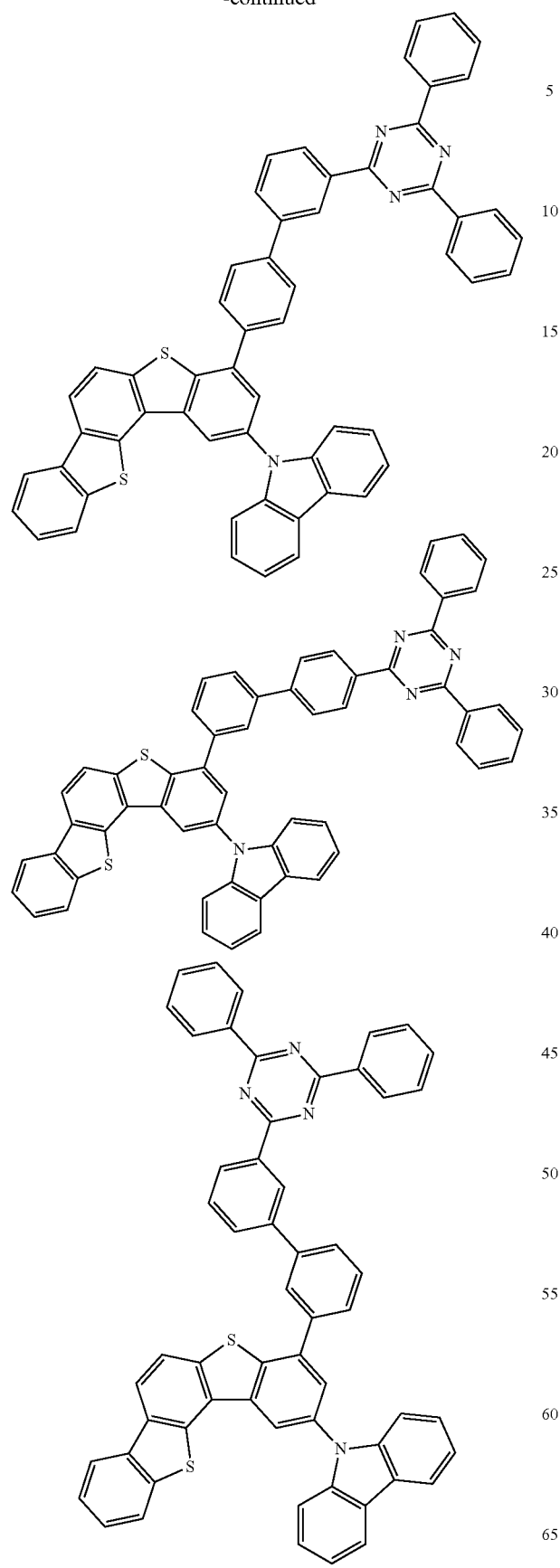
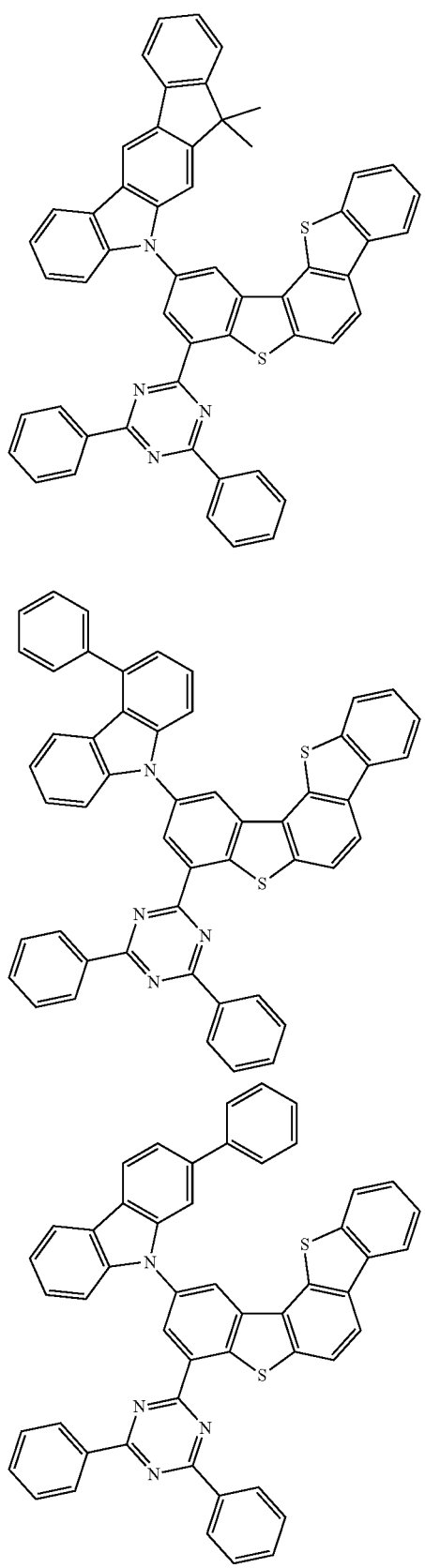

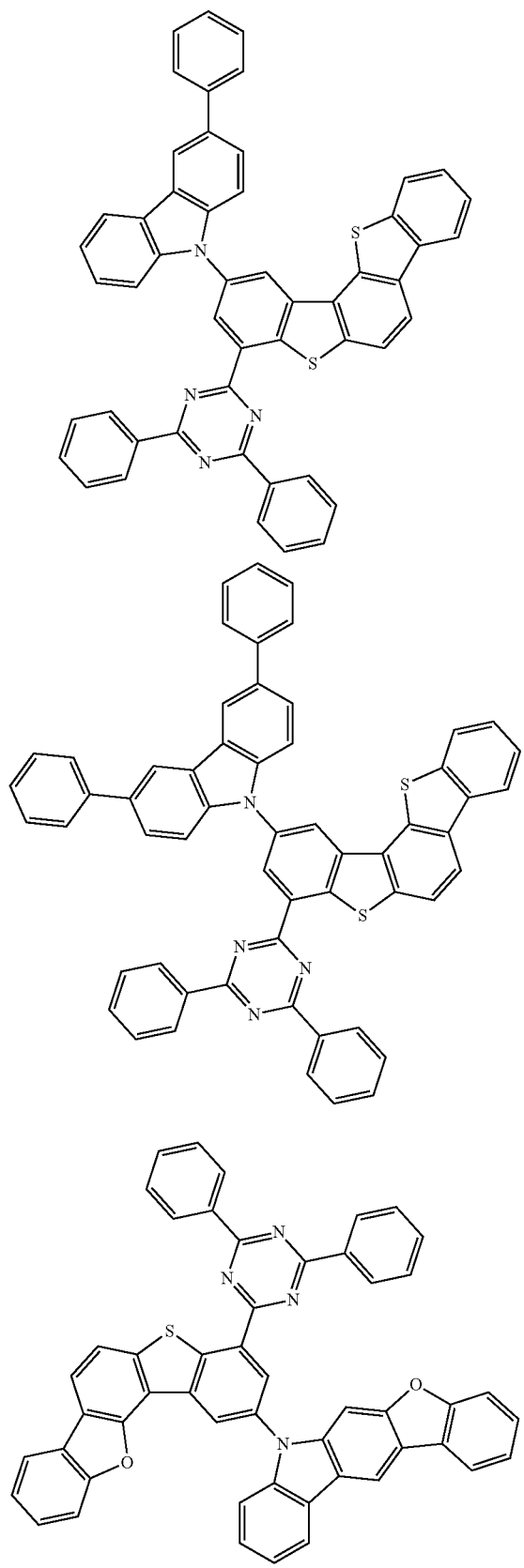
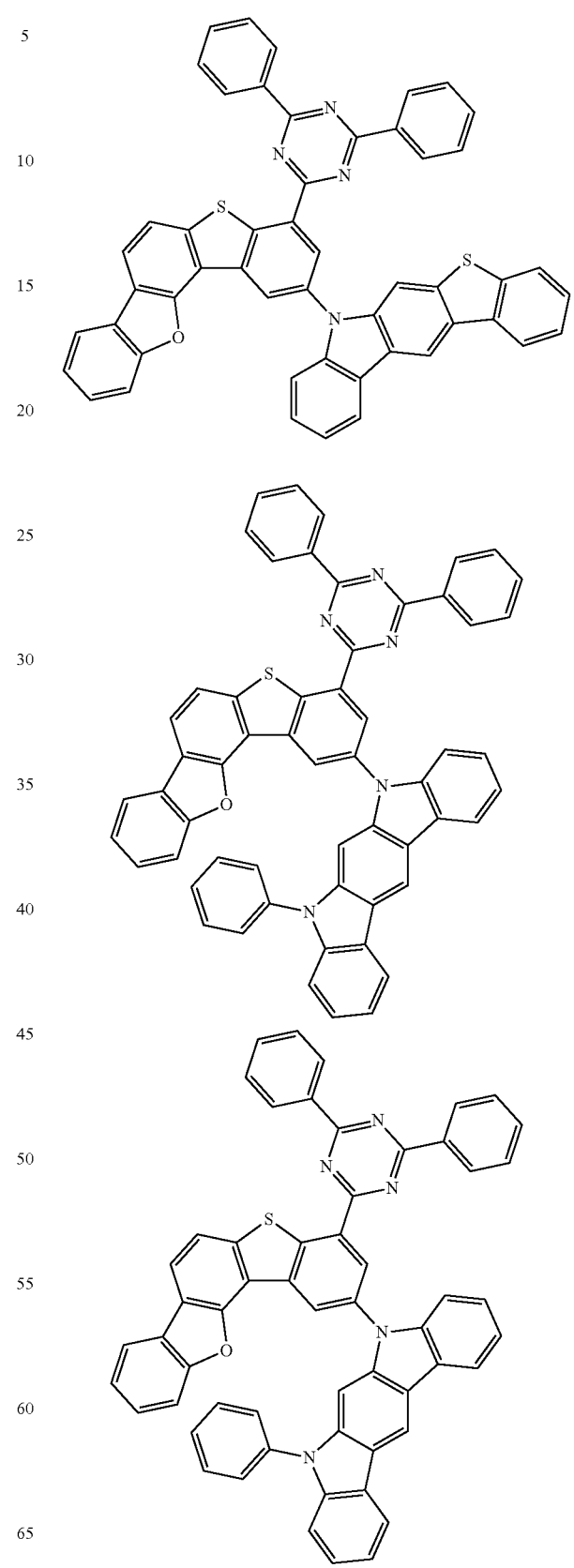

-continued
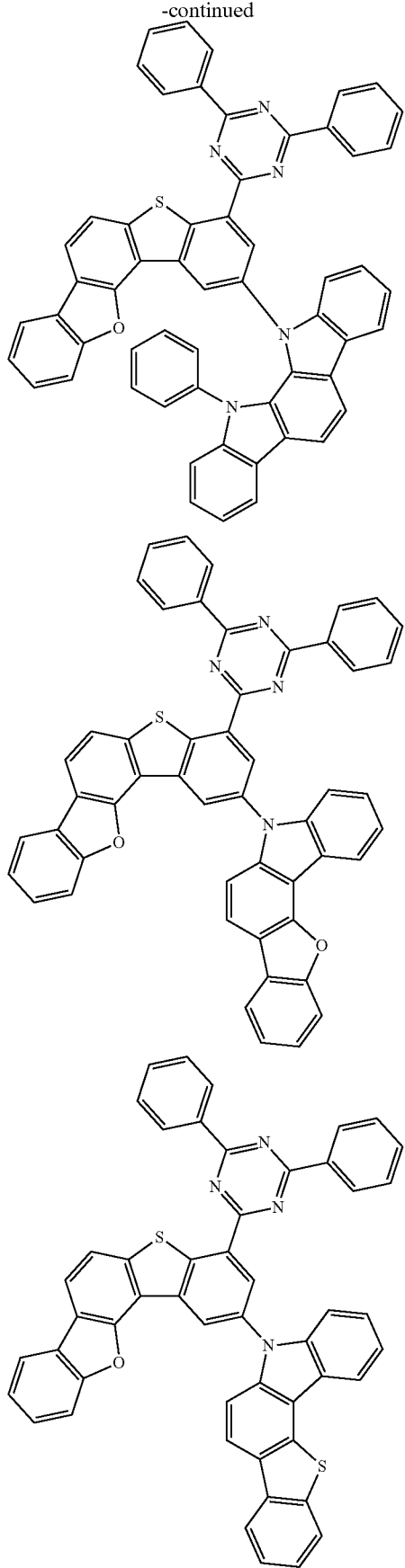
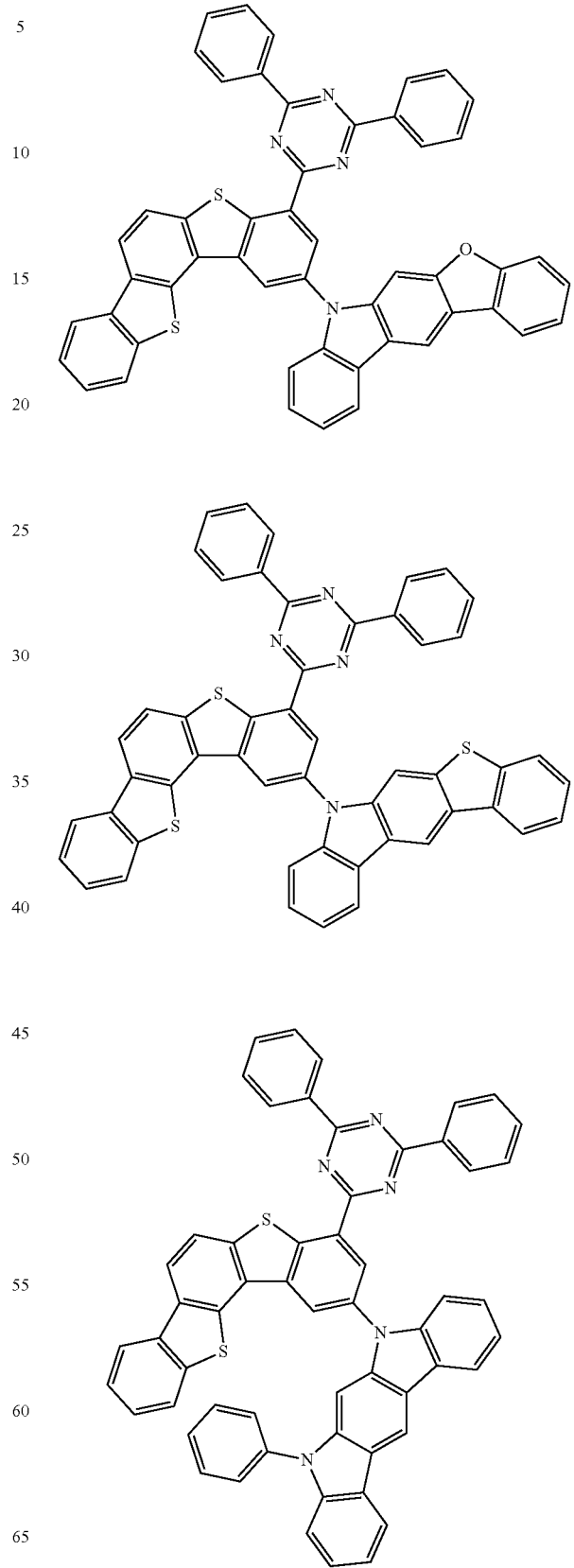

-continued
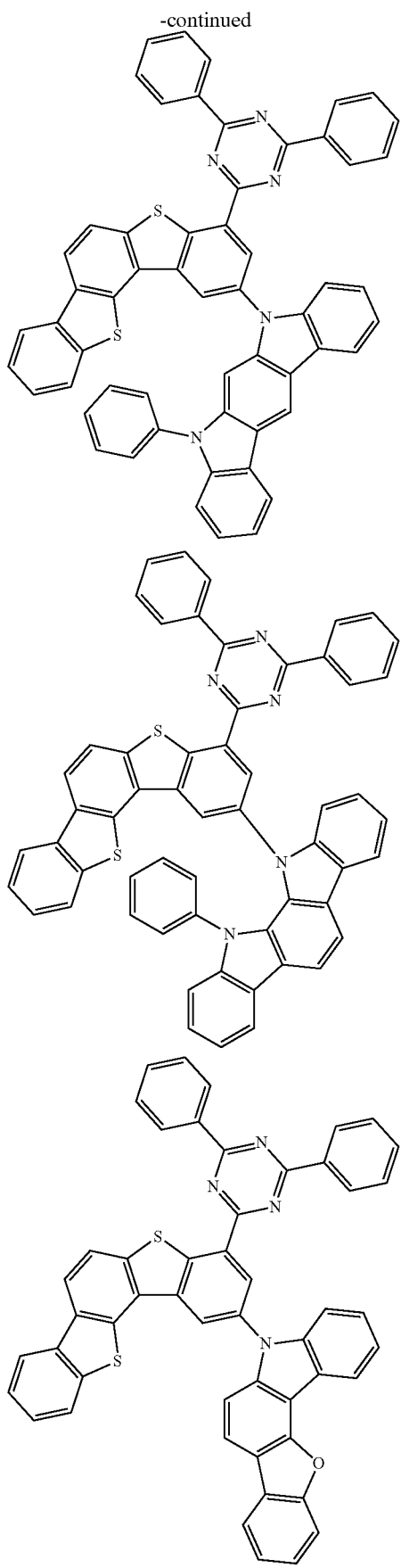
-continued
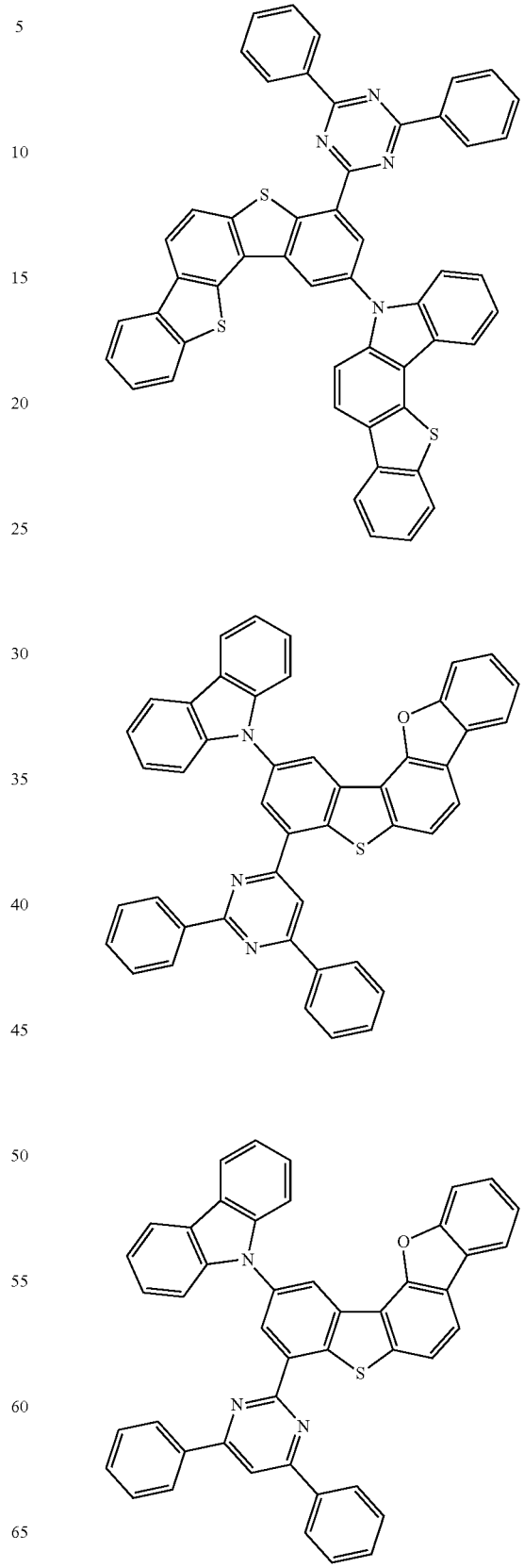

41
-continued

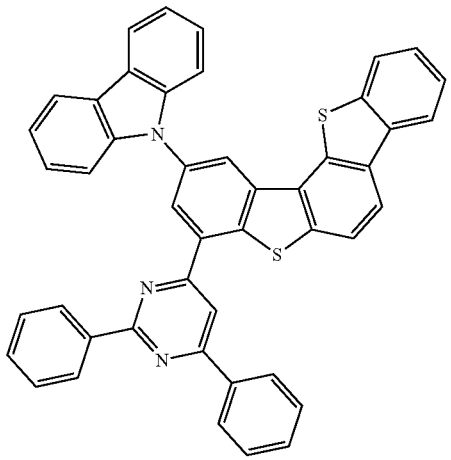

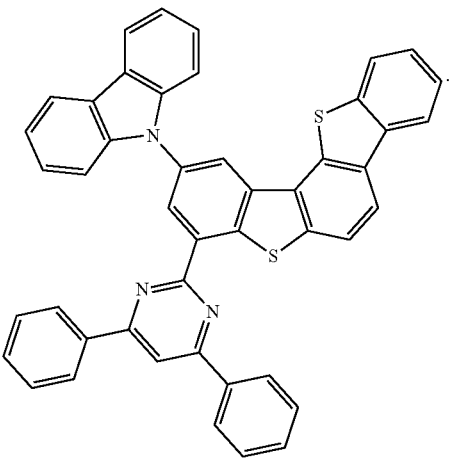 [SMILES: c1ccc(-c2cc(-c3ccccc3)nc(-c3cc(-n4c5ccccc5c5ccccc54)cc4c3sc3ccc5c6ccccc6sc5c34)n2)cc1]

The compound of Chemical Formula 1 can be prepared, for example, according to the preparation method as shown in the following Reaction Scheme 1.

Reaction Scheme 1

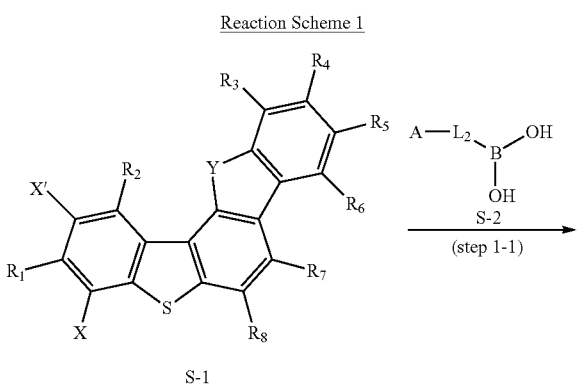

42
-continued

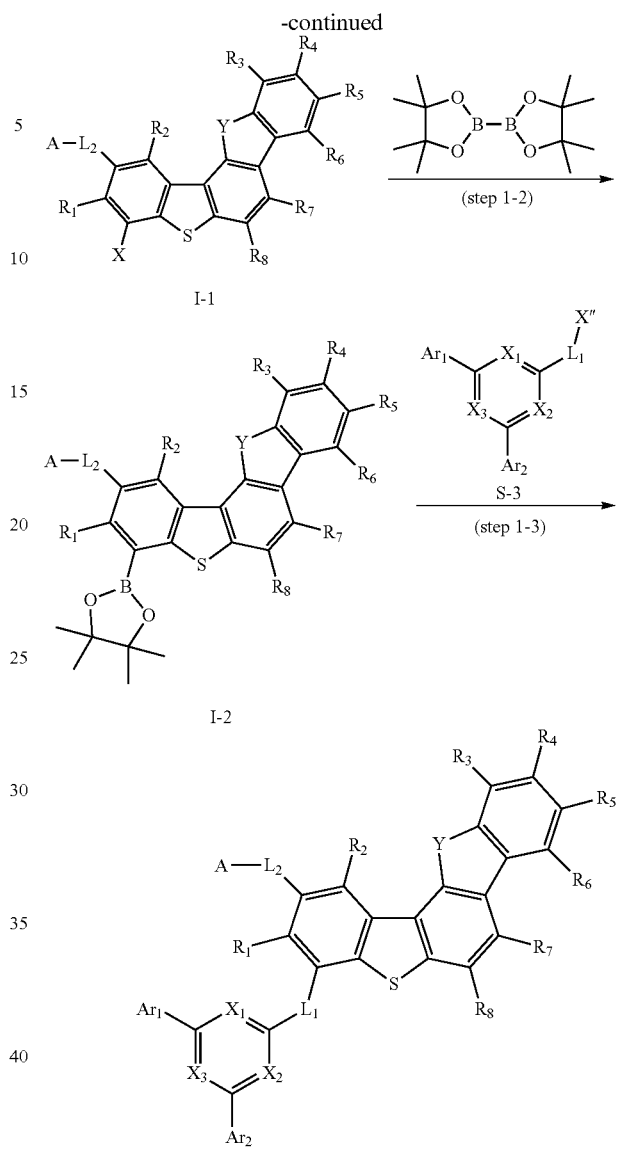

In Reaction Scheme 1, X, X', and X" are each independently a halogen, preferably bromo or chloro, and the definition of each substituent is as defined above.

Step 1-1 is a step of preparing an intermediate compound 1-1 by introducing a carbazole-based substituent into a starting material S-1, step 1-2 is a step for preparing an intermediate compound 1-2 by introducing a reactive group for Suzuki-coupling reaction, and step 1-3 is a step of preparing a compound of Chemical Formula 1 by introducing a triazine-based substituent through a Suzuki-coupling reaction.

At this time, the Suzuki-coupling reaction is preferably carried out in the presence of a palladium catalyst and a base, and the reactive group for the reaction can be modified into a reactive group known in the art.

Such a preparation method can be as further specified in preparation examples described hereinafter.

The compound of Chemical Formula 1 has a structure in which a triazine-based substituent and a carbazole-based substituent are simultaneously bonded to a benzofurodibenzothiophene or benzothienodibenzothiophene core. Thus, the organic light emitting device employing this compound can have a high efficiency, a low driving voltage, high luminance, and a long lifetime as compared with a conventional organic light emitting device employing a compound having a benzofurodibenzothiophene or benzothienodibenzothiophene core.

In another embodiment of the invention, there is provided an organic light emitting device including the compound of Chemical Formula 1 described above.

As an example, provided is an organic light emitting device including: a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present invention can have a single layer structure, or it can have a multilayered structure in which two or more organic material layers are stacked.

For example, the organic light emitting device of the present invention can have a structure including a hole injection layer, a hole transport layer, an electron blocking layer, a light emitting layer, an electron transport layer, an electron injection layer, and the like as the organic material layer.

However, the structure of the organic light emitting device is not limited thereto, and it can include a smaller number of organic layers.

Further, the organic material layer can include a light emitting layer, wherein the light emitting layer includes a compound of Chemical Formula 1.

In particular, the compound according to the present invention can be used as a host in a light emitting layer.

Specifically, the compound according to the present invention can be used as a green phosphorescent host in the light emitting layer.

Further, the organic material layer can include a light emitting layer, wherein the light emitting layer includes two or more kinds of hosts. At this time, one of the hosts can be a compound of Chemical Formula 1.

Further, the organic material layer can include an electron transport layer or an electron injection layer, wherein the electron transport layer or the electron injection layer can include a compound of Chemical Formula 1.

The organic material layer of the organic light emitting device of the present invention can have a single layer structure, or it can have a multilayered structure in which two or more organic material layers are stacked.

For example, the organic light emitting device of the present invention can have a structure further including a hole injection layer and a hole transport layer provided between the first electrode and the light emitting layer, and an electron transport layer and an electron injection layer provided between the light emitting layer and the second electrode, in addition to the light emitting layer.

However, the structure of the organic light emitting device is not limited thereto, and it can include a smaller number of organic layers or a larger number of organic layers.

Further, the organic light emitting device according to the present invention can be a normal type of organic light emitting device in which an anode, one or more organic material layers, and a cathode are sequentially stacked on a substrate, wherein the first electrode is an anode, and the second electrode is a cathode.

Further, the organic light emitting device according to the present invention can be an inverted type of organic light emitting device in which a cathode, one or more organic material layers, and an anode are sequentially stacked on a substrate, wherein the first electrode is a cathode and the second electrode is an anode.

For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4.

In such a structure, the compound of Chemical Formula 1 can be included in the light emitting layer.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4.

In such a structure, the compound of Chemical Formula 1 can be included in one or more layers of the hole injection layer, the hole transport layer, the light emitting layer, and the electron transport layer.

Preferably, the compound of Chemical Formula 1 can be included in the light emitting layer.

The organic light emitting device according to the present invention can be manufactured by materials and methods known in the art, except that one or more layers of the organic material layers include the compound of Chemical Formula 1.

In addition, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate.

In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon.

In addition to such a method, the organic light emitting device can be manufactured by sequentially depositing a cathode material, an organic material layer, and an anode material on a substrate.

In addition, the compound of Chemical Formula 1 can be formed into an organic layer by a solution coating method as well as a vacuum deposition method at the time of manufacturing an organic light emitting device.

Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (International Publication WO2003/012890).

However, the manufacturing method is not limited thereto.

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer.

Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline; and the like, but are not limited thereto.

As the cathode material, generally, a material having a small work function is preferably used so that electrons can be easily injected into the organic material layer.

Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film.

It is preferable that a HOMO (highest occupied molecular orbital) of the hole injection material is between the work function of the anode material and a HOMO of a peripheral organic material layer.

Specific examples of the hole injection material include metal porphyrine, oligothiophene, an arylamine-based organic material, a hexanitrile-hexaazatriphenylene-based organic material, a quinacridone-based organic material, a perylene-based organic material, anthraquinone, polyaniline, and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer.

Specific examples thereof include an arylamine-based organic material, a conductive polymer, a block copolymer in which a conjugate portion and a non-conjugate portion are present together, and the like, but are not limited thereto.

The electron blocking layer refers to a layer that is formed on the hole transport layer and is preferably disposed in contact with the light emitting layer to adjust hole mobility, prevent excessive movement of electrons and increase the probability of hole-electron bonding, thereby serving to improve the efficiency of an organic light emitting diode.

The electron blocking layer includes an electron blocking material, and examples of such electron blocking materials include arylamine-based organic materials and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence.

Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole-, benzothiazole-, and benzimidazole-based compound; a poly(p-phenylenevinylene) (PPV)-based polymer; a spiro compound; polyfluorene, rubrene, and the like; but are not limited thereto.

The light emitting layer can include a host material and a dopant material as described above.

The host material can include the compound of Chemical Formula 1.

Alternatively, the light emitting layer includes two or more kinds of hosts, wherein one of the hosts is a compound of Chemical Formula 1, and the other host material can be a fused aromatic ring derivative, a heterocyclic-containing compound, or the like.

Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

For example, the light emitting layer can include two kinds of hosts, wherein the two kinds of hosts can be a compound of Chemical Formula 1 and a biscarbazole derivative, respectively.

Examples of the dopant material include an aromatic amine derivative, a styrylamine compound, a boron complex, a fluoranthene compound, a metal complex, and the like.

Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted.

Specific examples thereof include styrylamine, styryldiamine, styryltriamine, styryltetramine, and the like, but are not limited thereto.

Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons.

Specific examples thereof include: an Al complex of 8-hydroxyquinoline; a complex including $Alq_3$; an organic radical compound; a hydroxyflavone-metal complex; and the like, but are not limited thereto.

The electron transport layer can be used with any desired cathode material, as used according to the related art.

In particular, appropriate examples of the cathode material are a typical material which has a low work function, followed by an aluminum layer or a silver layer.

Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention can be a front emission type, a back emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples.

However, these examples are presented for illustrative purposes only, and are not intended to limit the scope of the present invention.

Preparation Example A: Preparation of Intermediate Compound A-4

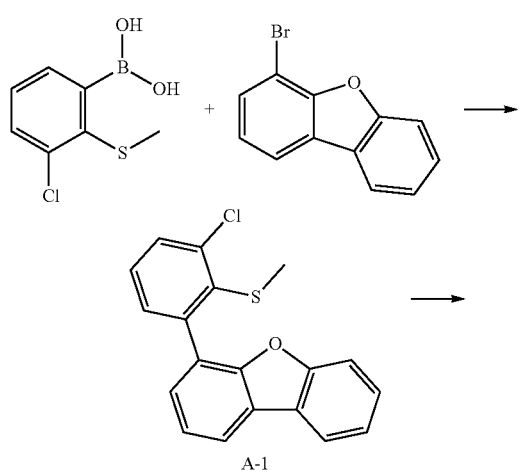

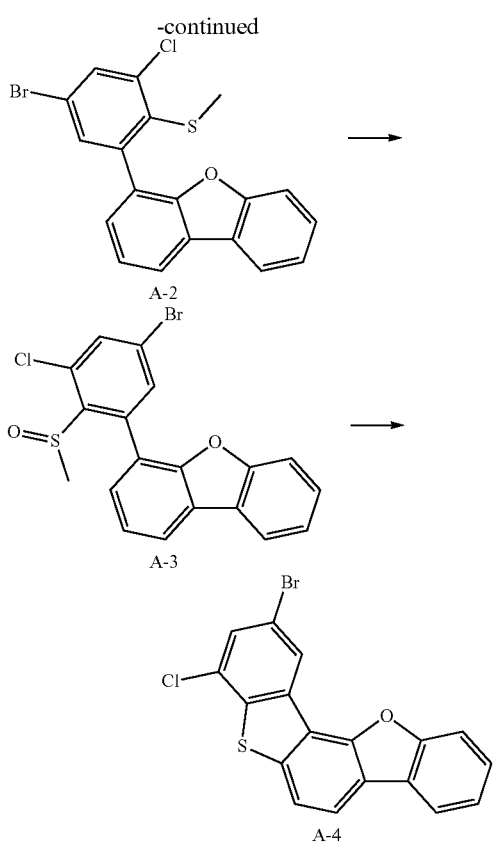

1) Preparation of Compound A-1

(3-chloro-2-(methylthio)phenyl)boronic acid (50.0 g, 247.5 mmol) and 4-bromodibenzo[b,d]furan (60.9 g, 247.5 mmol) were added to 400 ml of tetrahydrofuran under a nitrogen atmosphere, and the mixture was stirred and refluxed. Then, potassium carbonate (102.6 g, 742.5 mmol) was added to and dissolved in 200 ml of water and sufficiently stirred, to which tetrakistriphenyl-phosphinopalladium (8.6 g, 3 mol %) was added. After reaction for 12 hours, the reaction mixture was cooled to room temperature, the organic layer and the aqueous layer were separated, and then the organic layer was distilled under reduced pressure. The distillate was extracted with chloroform and water, and then the organic layer was dried with magnesium sulfate. Subsequently, the organic layer was dried, and then recrystallized with ethanol to prepare Compound A-1 (56.1 g, 70%).

MS: $[M+H]^+$=325

2) Preparation of Compound A-2

Compound A-1 (56.1 g, 173.1 mmol) was added to and dissolved in 500 ml of chloroform under a nitrogen atmosphere and sufficiently stirred at 0° C., and then bromine (32.8 g, 207.8 mmol) was slowly added dropwise. The reaction mixture was gradually heated to room temperature and allowed to react for 8 hours, and then water was added to terminate the reaction. Then, the reaction mixture was each extracted three times with water and sodium thiosulfate solution, and the organic layer was distilled under reduced pressure. The distillate was extracted with chloroform and water, and then the organic layer was dried with magnesium sulfate. Subsequently, the organic layer was dried, and then recrystallized with ethanol to prepare Compound A-2 (58.5 g, 84%).

MS: [M+H]$^+$=403

3) Preparation of Compound A-3

Compound A-2 (58.5 g, 145.5 mmol) was added to and dissolved in 600 ml of acetic acid under a nitrogen atmosphere and sufficiently stirred at room temperature, and then hydrogen peroxide (16.5 g, 145.5 mmol) was slowly added dropwise. The reaction mixture was gradually heated to room temperature and allowed to react for 24 hours, and then water was added to terminate the reaction. Then, the reaction mixture was extracted three times with water and chloroform, and the organic layer was distilled under reduced pressure. The distillate was extracted with chloroform and water, and then the organic layer was dried with magnesium sulfate. Subsequently, the organic layer was dried, and then completely distilled through a vacuum distillation apparatus to prepare Compound A-3 (60.8 g, 100%).

MS: [M+H]$^+$=419

4) Preparation of Compound A-4

Compound A-3 (60.8 g, 145.5 mmol) was added to 300 ml of dimethylformamide and stirred. Then, potassium carbonate (134.1 g, 291.1 mmol) was added and refluxed. After 2 hours, the reaction mixture was cooled to room temperature and filtered. The filtrate was extracted with chloroform and water, and then the organic layer was dried with magnesium sulfate. Then, the organic layer was distilled under reduced pressure and recrystallized using ethyl acetate. The produced solid was filtered and then dried to prepare Compound A-4 (38.8 g, 69%).

MS: [M+H]$^+$=387

Preparation Example B: Preparation of Intermediate Compound B-4

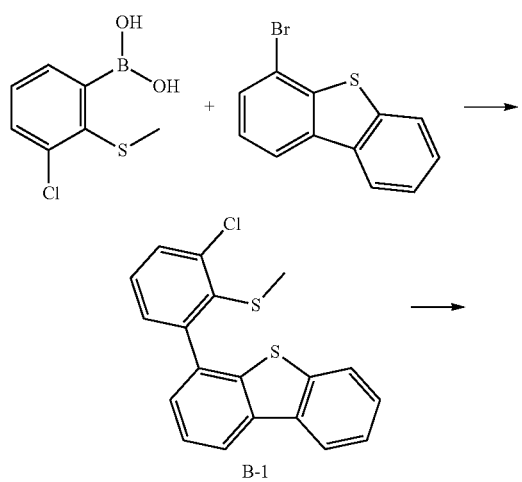

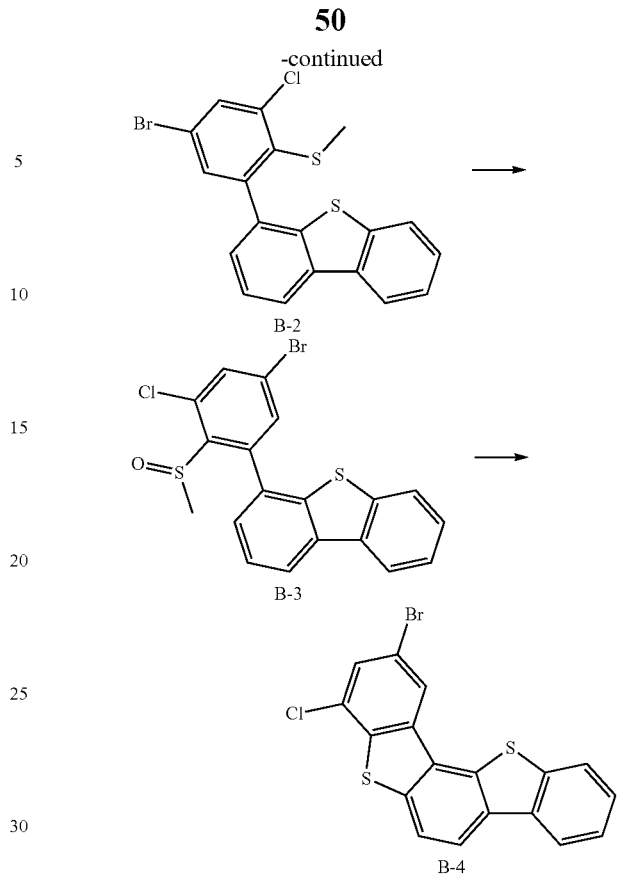

1) Preparation of Compound B-1

(3-chloro-2-(methylthio)phenyl)boronic acid (50.0 g, 247.5 mmol) and 4-bromodibenzo[b,d]thiophene (64.8 g, 247.5 mmol) were added to 400 ml of tetrahydrofuran under a nitrogen atmosphere, and the mixture was stirred and refluxed. Then, potassium carbonate (102.6 g, 742.5 mmol) was added to and dissolved in 200 ml of water and sufficiently stirred, to which tetrakistriphenyl-phosphinopalladium (8.6 g, 3 mol %) was added. After reaction for 12 hours, the temperature was lowered to room temperature, the organic layer and the aqueous layer were separated, and then the organic layer was distilled under reduced pressure. The distillate was extracted with chloroform and water, and then the organic layer was dried with magnesium sulfate. Subsequently, the organic layer was dried, and then recrystallized with ethanol to prepare Compound B-1 (61.4 g, 73%).

MS: [M+H]$^+$=341

2) Preparation of Compound B-2

Compound B-1 (61.4 g, 180.6 mmol) was added to and dissolved in 500 ml of chloroform under a nitrogen atmosphere and sufficiently stirred at 0° C., and then bromine (34.2 g, 216.7 mmol) was slowly added dropwise. The reaction mixture was gradually heated to room temperature and allowed to react for 8 hours, and then water was added to terminate the reaction.

Then, the reaction mixture was each extracted three times with water and a sodium thiosulfate solution, and the organic layer was distilled under reduced pressure. The distillate was extracted with chloroform and water, and then the organic layer was dried with magnesium sulfate. Subsequently, the organic layer was dried, and then recrystallized with ethanol to prepare Compound B-2 (52.8 g, 70%).
MS: [M+H]⁺=418

3) Preparation of Compound B-3

Compound B-2 (52.8 g, 126.3 mmol) was added to and dissolved in 500 ml of acetic acid under a nitrogen atmosphere and sufficiently stirred at room temperature, and then hydrogen peroxide (14.3 g, 126.3 mmol) was slowly added dropwise. The reaction mixture was gradually heated to room temperature and allowed to react for 24 hours, and then water was added to terminate the reaction. Then, the reaction mixture was extracted three times with water and chloroform, and the organic layer was distilled under reduced pressure. The distillate was extracted with chloroform and water, and then the organic layer was dried with magnesium sulfate. Subsequently, the organic layer was dried, and then completely distilled through a vacuum distillation apparatus to prepare Compound B-3 (54.8 g, 100%).
MS: [M+H]⁺=435

4) Preparation of Compound B-4

Compound B-3 (54.8 g, 126.3 mmol) was dissolved in 300 ml of dimethylformamide under a nitrogen atmosphere, and the mixture was stirred. Then, potassium carbonate (116.4 g, 252.7 mmol) was added and refluxed. After 2 hours, the temperature was raised to room temperature, and filtered. The filtrate was extracted with chloroform and water, and then the organic layer was dried with magnesium sulfate. Subsequently, the organic layer was distilled under reduced pressure and recrystallized using ethyl acetate. The resulting solid was filtered and then dried to prepare Compound B-4 (27.4 g, 54%).
MS: [M+H]⁺=403

Preparation Example 1: Preparation of Compound 1

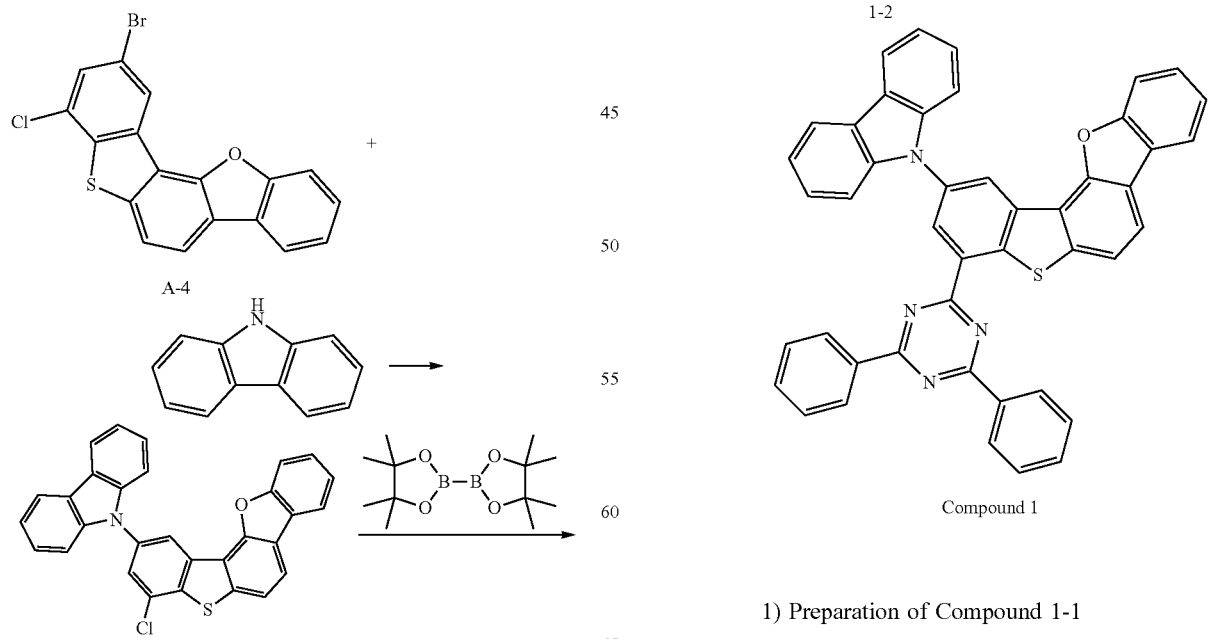

1) Preparation of Compound 1-1

The compound A-4 (20.0 g, 51.8 mmol) prepared in Preparation Example A and 9H-carbazole (10.4 g, 62.2 mmol) were added to and dissolved in 100 ml of xylene, to which sodium tert-butoxide (14.3 g, 103.7 mmol) was added and heated. Bis(tri-tert-butylphosphine)palladium (0.8 g, 3 mol %) was added and stirred under reflux for 12 hours. When the reaction was completed, the temperature was lowered to room temperature and the produced solid was filtered. The solid was dissolved in 700 mL of chloroform and washed twice with water. The organic layer was separated, and anhydrous magnesium sulfate was added thereto. The mixture was stirred and then filtered, and the filtrate was distilled under reduced pressure. The concentrated compound was purified through a silica column using chloroform and ethyl acetate to prepare a pale green solid compound 1-1 (13.2 g, 54%).

MS: [M+H]⁺=474

2) Preparation of Compound 1-2

The compound 1-1 (13.2 g, 27.9 mmol), bis(pinacolato) diboron (7.8 g, 30.7 mmol), and potassium acetate (5.5 g, 55.9 mmol) were mixed under a nitrogen atmosphere, to which 200 ml of dioxane was added and heated while stirring. Bis(dibenzylideneacetone)palladium (0.5 g, 0.8 mmol) and tricyclohexylphosphine (0.5 g, 1.6 mmol) were added under a reflux condition, and the mixture was heated and stirred for 3 hours. After completion of the reaction, the reaction mixture was cooled to room temperature and then filtered. Water was poured into the filtrate, extracted with chloroform, and the organic layer was dried with anhydrous magnesium sulfate. After distillation under reduced pressure, the product was recrystallized with ethanol to prepare Compound 1-2 (15.2 g, 83%).

MS: [M+H]⁺=566

3) Preparation of Compound 1

Compound 1-2 (15.2 g, 26.9 mmol) and 2-chloro-4,6-diphenyl-1,3,5-trazine (7.2 g, 26.9 mmol) were added to 200 ml of tetrahydrofuran under a nitrogen atmosphere, and the mixture was stirred and refluxed. Then, potassium carbonate (11.2 g, 80.7 mmol) was added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 1 (7.9 g, 44%).

MS: [M+H]⁺=671

Preparation Example 2: Preparation of Compound 2

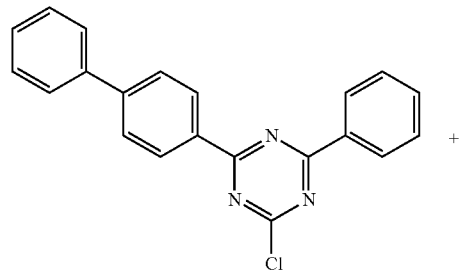

-continued

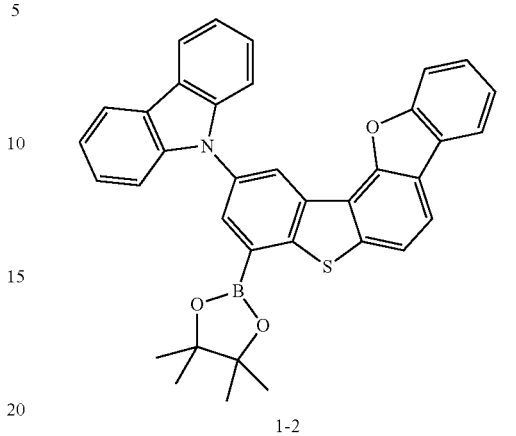

1-2

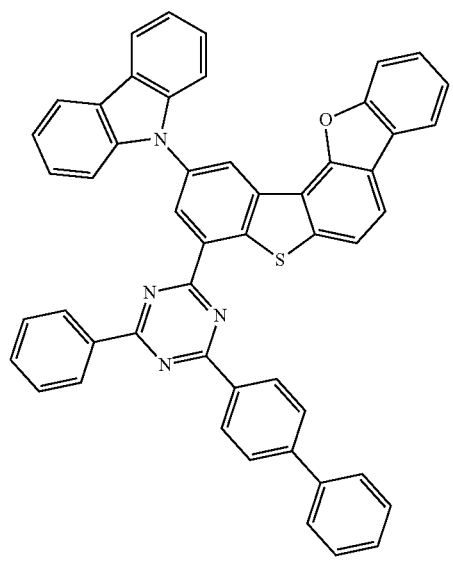

Compound 2

The compound 1-2 (15.2 g, 26.9 mmol) prepared in Preparation Example 1 and 2-([1,1'-biphenyl]-4-yl)-4-chloro-6-phenyl-1,3,5-triazine (9.2 g, 26.9 mmol) were added to 200 ml of tetrahydrofuran under a nitrogen atmosphere, and the mixture was stirred and refluxed. Then, potassium carbonate (11.2 g, 80.7 mmol) was and added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 2 (11.2 g, 56%).

MS: [M+H]⁺=747

Preparation Example 3: Preparation of Compound 3

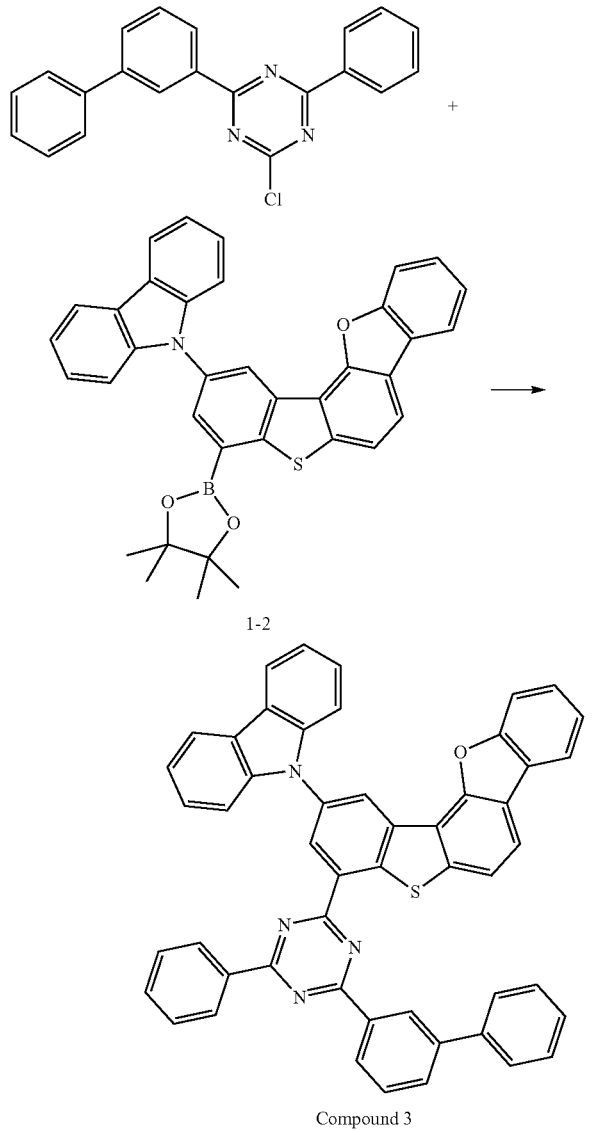

Compound 3

The compound 1-2 (15.2 g, 26.9 mmol) prepared in Preparation Example 1 and 2-([1,1'-biphenyl]-3-yl)-4-chloro-6-phenyl-1,3,5-triazine (9.2 g, 26.9 mmol) were added to 200 ml of tetrahydrofuran under a nitrogen atmosphere, and the mixture was stirred and refluxed. Then, potassium carbonate (11.2 g, 80.7 mmol) was added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 3 (12.2 g, 61%).

MS: [M+H]$^+$=747

Preparation Example 4: Preparation of Compound 4

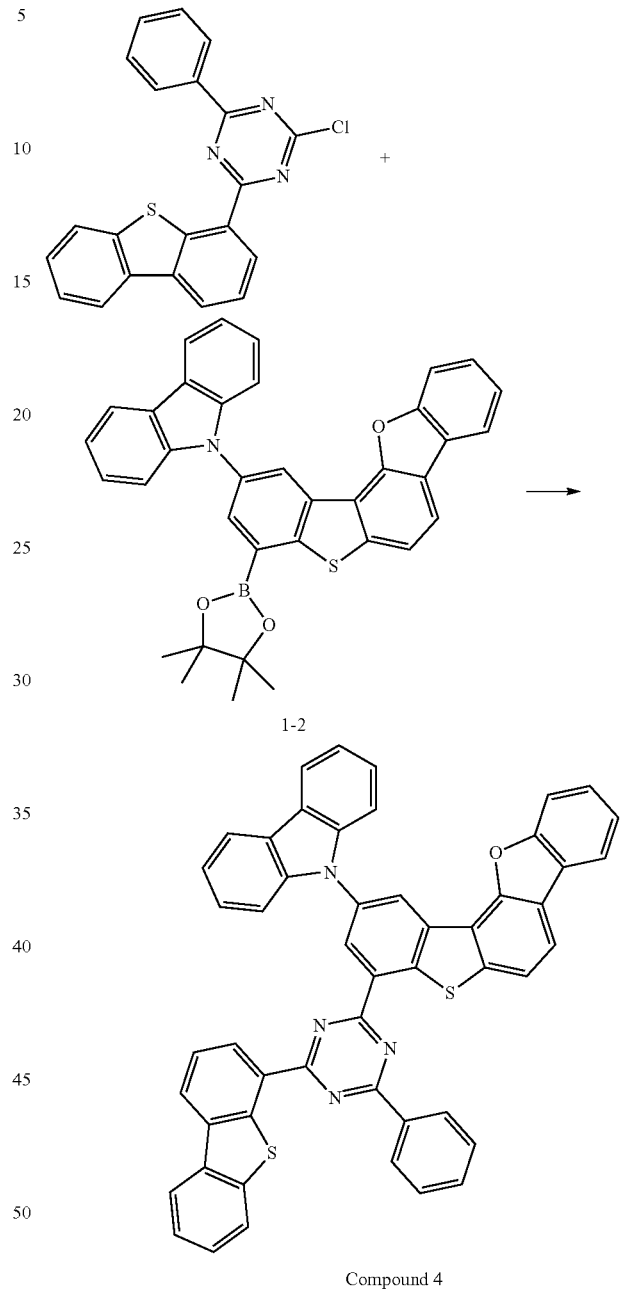

Compound 4

The compound 1-2 (15.2 g, 26.9 mmol) prepared in Preparation Example 1 and 2-chloro-4-(dibenzo[b,d]thiophen-4-yl)-6-phenyl-1,3,5-triazine (10.0 g, 26.9 mmol) were added to 200 ml of tetrahydrofuran under a nitrogen atmosphere, and the mixture was stirred and refluxed. Then, potassium carbonate (11.2 g, 80.7 mmol) was added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 4 (14.6 g, 70%).

MS: [M+H]⁺=777

Preparation Example 5: Preparation of Compound 5 room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 5 (10.0 g, 50%).

MS: [M+H]⁺=747

Preparation Example 6: Preparation of Compound 6

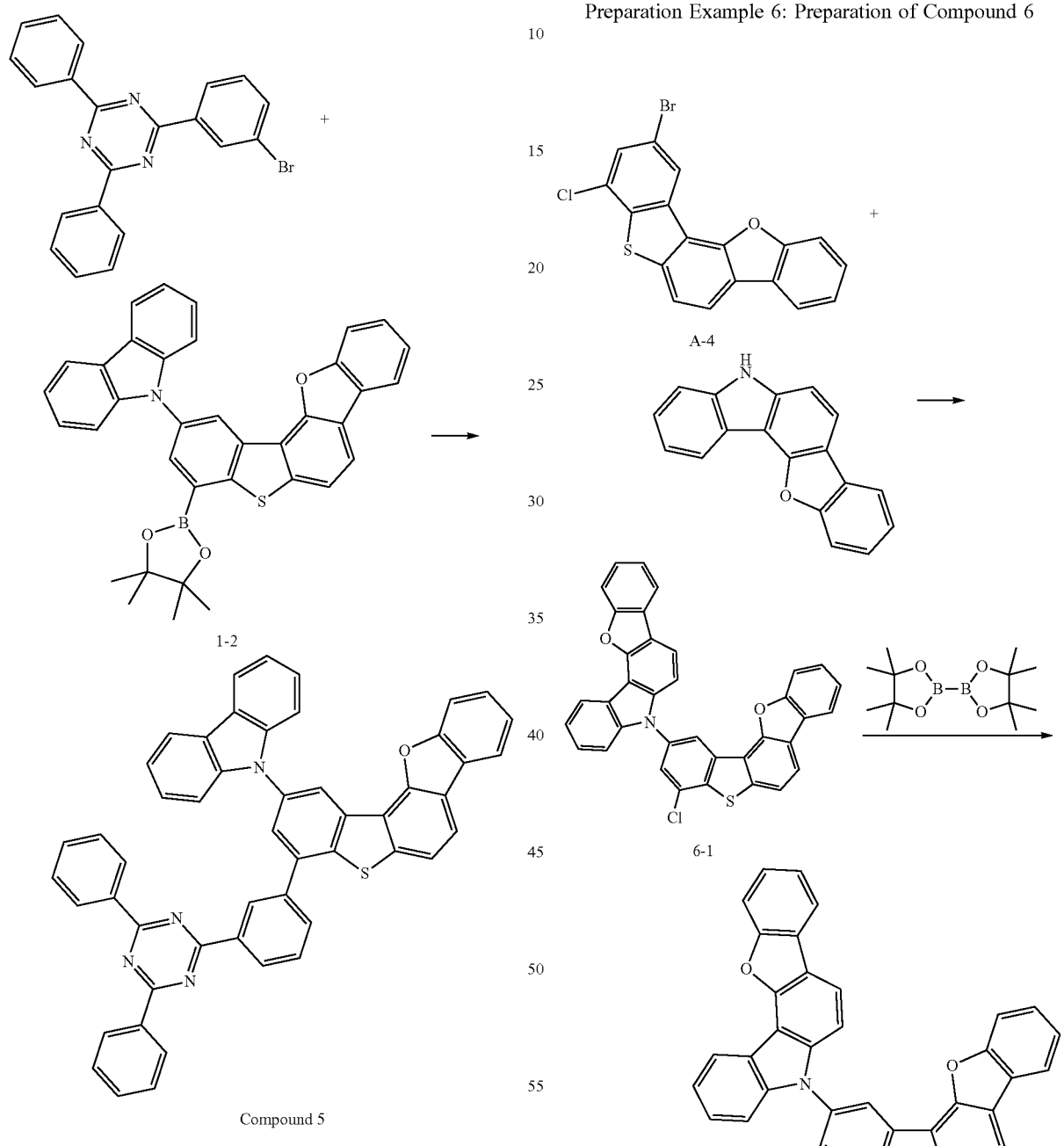

The compound 1-2 (15.2 g, 26.9 mmol) prepared in Preparation Example 1 and 2-(3-bromophenyl)-4,6-diphenyl-1,3,5-triazine (10.0 g, 26.9 mmol) were added to 200 ml of tetrahydrofuran under a nitrogen atmosphere, and the mixture was stirred and refluxed. Then, potassium carbonate (11.2 g, 80.7 mmol) was added to and dissolved in 30 ml of water and sufficiently stirred, to which tetrakistriphenylphosphinopalladium (0.9 g, 3 mol %) was added. After reaction for 4 hours, the reaction mixture was cooled to

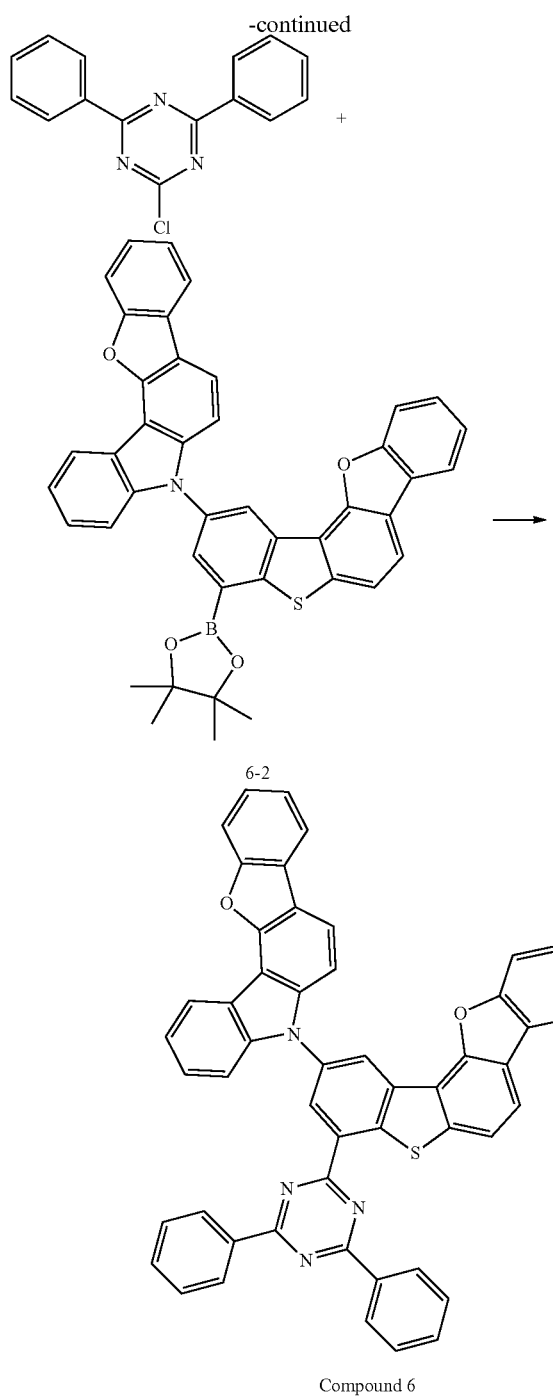

6-2

Compound 6

1) Preparation of Compound 6-1

The compound A-4 (20.0 g, 51.8 mmol) prepared in Preparation Example A and 5H-benzofuro[3,2-c]carbazole (16.0 g, 62.2 mmol) was added to and dissolved in 100 ml of xylene, to which sodium tert-butoxide (14.3 g, 103.7 mmol) was added, and heated. Bis(tri-tert-butylphosphine) palladium (0.8 g, 3 mol %) was added and stirred under reflux for 12 hours. When the reaction was completed, the temperature was lowered to room temperature and the produced solid was filtered. The solid was dissolved in 700 mL of chloroform and washed twice with water. The organic layer was separated, and anhydrous magnesium sulfate was added thereto. The mixture was stirred and then filtered, and the filtrate was distilled under reduced pressure. The concentrated compound was purified through a silica column using chloroform and ethyl acetate to prepare a pale green solid compound 6-1 (19.3 g, 66%).

MS: $[M+H]^+=564$

2) Preparation of Compound 6-2

The compound 6-1 (19.3 g, 34.3 mmol), bis(pinacolato)diboron (9.6 g, 37.7 mmol), and potassium acetate (6.7 g, 68.6 mmol) were mixed under a nitrogen atmosphere, to which 200 ml of dioxane was added, and heated while stirring. Bis(dibenzylideneacetone)palladium (0.6 g, 1.0 mmol) and tricyclohexylphosphine (0.6 g, 2.0 mmol) were added under a reflux condition, and the mixture was heated and stirred for 3 hours. After completion of the reaction, the reaction mixture was cooled to room temperature and then filtered. Water was poured into the filtrate, extracted with chloroform, and the organic layer was dried with anhydrous magnesium sulfate. After distillation under reduced pressure, the product was recrystallized with ethanol to prepare Compound 6-2 (17.5 g, 78%).

MS: $[M+H]^+=656$

3) Preparation of Compound 6

Compound 6-2 (17.5 g, 26.7 mmol) and 2-chloro-4,6-diphenyl-1,3,5-trazine (8.6 g, 32.1 mmol) were added to 200 ml of tetrahydrofuran under a nitrogen atmosphere, and the mixture was stirred and refluxed. Then, potassium carbonate (11.1 g, 80.1 mmol) was and added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 6 (10.2 g, 50%).

MS: $[M+H]^+=761$

Preparation Example 7: Preparation of Compound 7

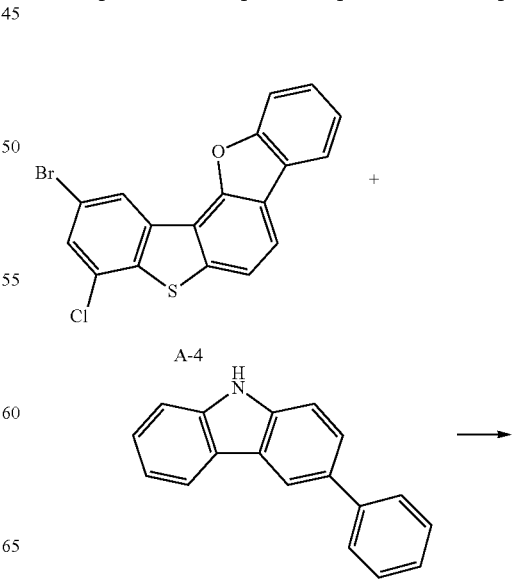

A-4

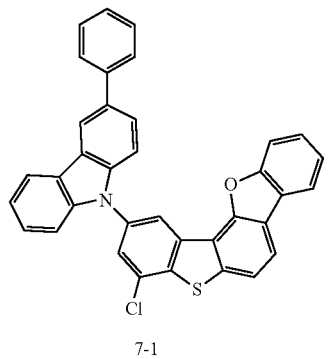

7-1

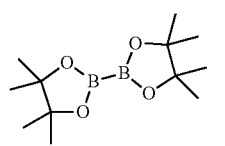

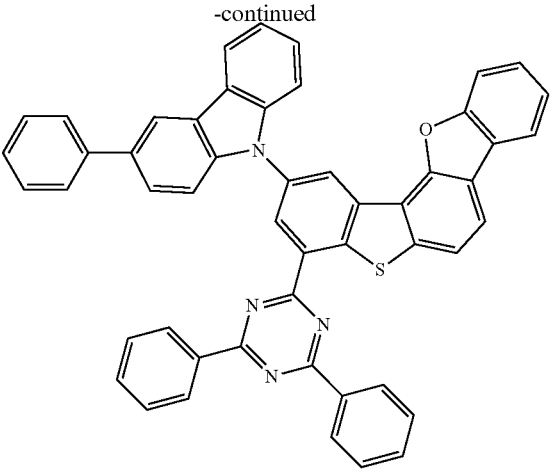

Compound 7

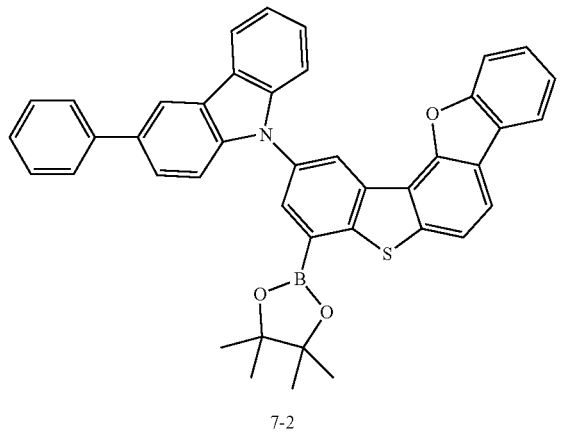

7-2

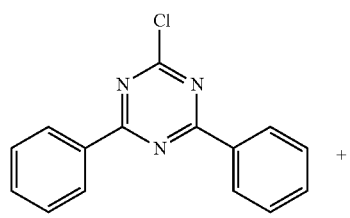

+

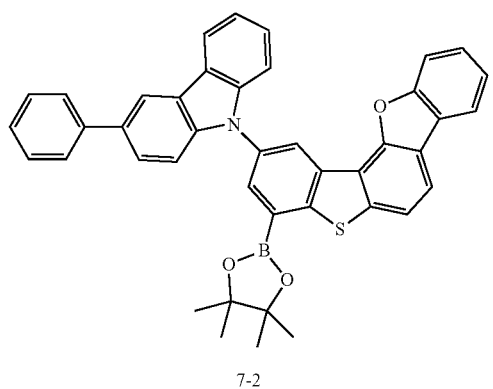

7-2

1) Preparation of Compound 7-1

The compound A-4 (20.0 g, 51.8 mmol) prepared in Preparation Example A and 3-phenyl-9H-carbazole (15.1 g, 62.2 mmol) were added to and dissolved in 100 ml of xylene, to which sodium tert-butoxide (14.3 g, 103.7 mmol) was added and heated. Bis(tri-tert-butylphosphine)palladium (0.8 g, 3 mol %) was added and stirred under reflux for 12 hours. When the reaction was completed, the temperature was lowered to room temperature and the produced solid was filtered. The solid was dissolved in 700 mL of chloroform and washed twice with water. The organic layer was separated, and anhydrous magnesium sulfate was added thereto. The mixture was stirred and then filtered, and the filtrate was distilled under reduced pressure. The concentrated compound was purified through a silica column using chloroform and ethyl acetate to prepare a pale green solid compound 7-1 (17.9 g, 63%).
MS: $[M+H]^+=550$ 2) Preparation of Compound 7-2

The compound 7-1 (17.9 g, 32.6 mmol), bis(pinacolato)diboron (9.1 g, 35.9 mmol), and potassium acetate (6.4 g, 65.2 mmol) were mixed under a nitrogen atmosphere, to which 200 ml of dioxane was added and heated while stirring. Bis(dibenzylideneacetone)palladium (0.6 g, 1.0 mmol) and tricyclohexylphosphine (0.6 g, 2.0 mmol) were added under a reflux condition, and the mixture was heated and stirred for 3 hours. After completion of the reaction, the reaction mixture was cooled to room temperature and then filtered. Water was poured into the filtrate, extracted with chloroform, and the organic layer was dried with anhydrous magnesium sulfate. After distillation under reduced pressure, the product was recrystallized with ethanol to prepare Compound 7-2 (16.9 g, 81%).
MS: $[M+H]^+=642$ 3) Preparation of Compound 7

Compound 7-2 (16.9 g, 26.4 mmol) and 2-chloro-4,6-diphenyl-1,3,5-triazine (8.4 g, 31.6 mmol) were added to 200 ml of tetrahydrofuran under a nitrogen atmosphere, and the mixture was stirred and refluxed. Then, potassium carbonate (10.9 g, 79.1 mmol) was added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 7 (8.9 g, 45%).

MS: $[M+H]^+=747$

Preparation Example 8: Preparation of Compound 8

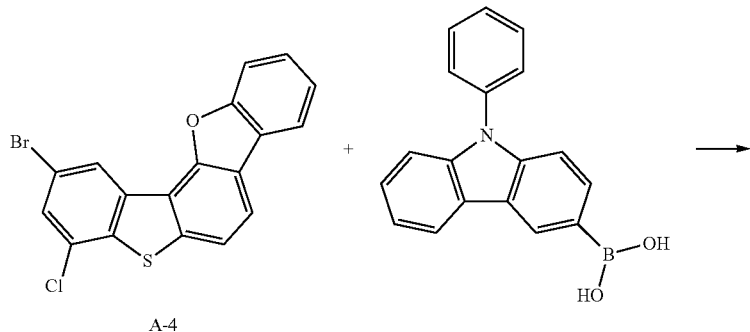

A-4

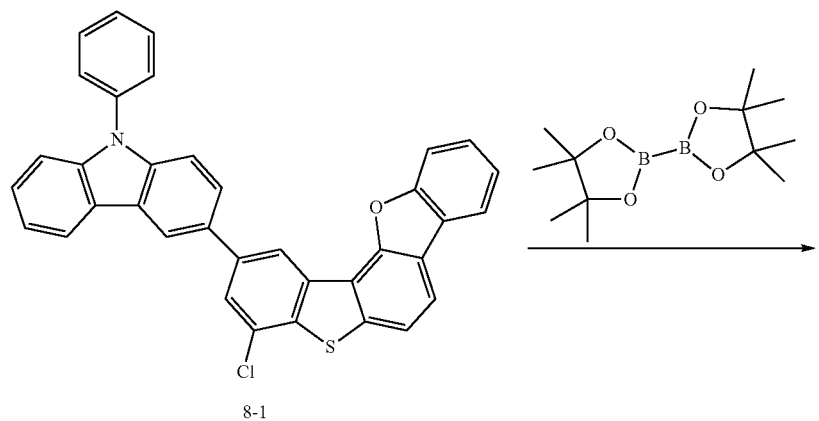

8-1

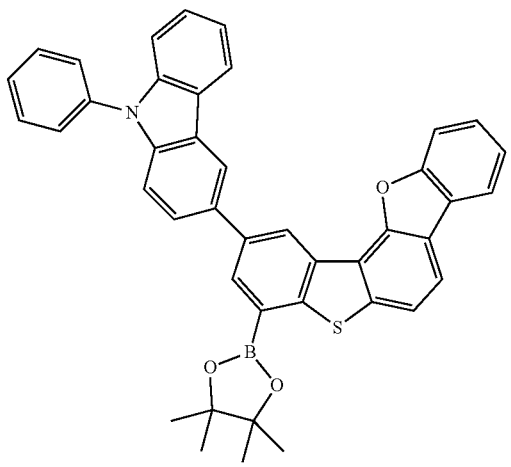

8-2

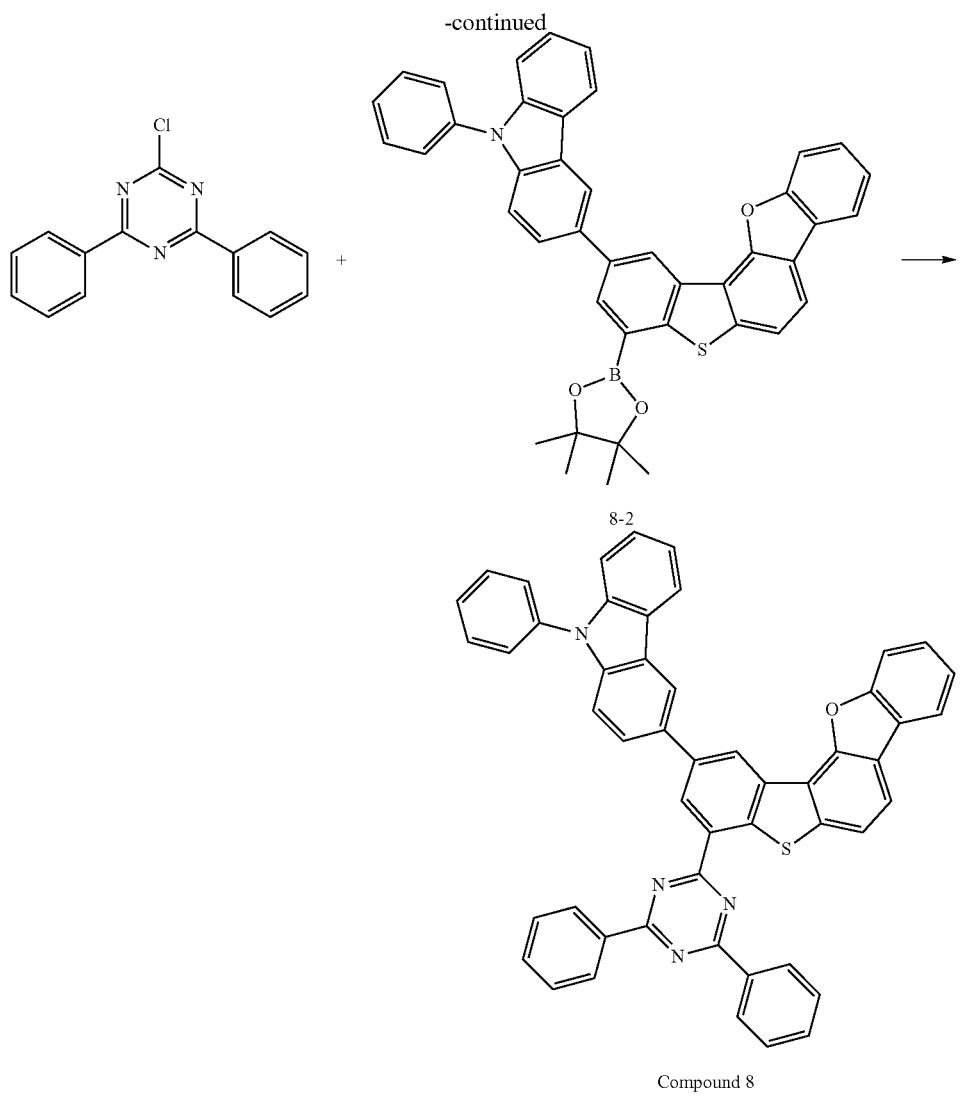

Compound 8

1) Preparation of Compound 8-1

The compound A-4 (20.0 g, 51.8 mmol) prepared in Preparation Example A and (9-phenyl-9H-carbazol-3-yl) boronic acid (16.4 g, 62.2 mmol) were added to 200 mL of tetrahydrofuran and dissolved. Potassium carbonate (21.5 g, 103.7 mmol) was dissolved in water and added, and the mixture was heated. Tetrakistriphenyl-phosphinopalladium (1.8 g, 3 mol %) was added thereto, and the mixture was stirred under reflux for 12 hours. When the reaction was completed, the temperature was lowered to room temperature and the produced solid was filtered. The solid was dissolved in 700 mL of chloroform and washed twice with water. The organic layer was separated, and anhydrous magnesium sulfate was added thereto. The mixture was stirred and then filtered, and the filtrate was distilled under reduced pressure. The concentrated compound was purified through a silica column using chloroform and ethyl acetate to prepare a pale green solid compound 8-1 (21.6 g, 76%).

MS: $[M+H]^+$=550

2) Preparation of Compound 8-2

The compound 8-1 (21.6 g, 39.3 mmol), bis(pinacolato) diboron (11.0 g, 43.3 mmol) and potassium acetate (7.7 g, 78.7 mmol) were mixed under a nitrogen atmosphere, to which 200 ml of dioxane was added and heated while stirring. Bis(dibenzylideneacetone)palladium (0.7 g, 1.2 mmol) and tricyclohexylphosphine (0.7 g, 2.4 mmol) were added under a reflux condition, and the mixture was heated and stirred for 4 hours. After completion of the reaction, the reaction mixture was cooled to room temperature and then filtered. Water was poured into the filtrate, extracted with chloroform, and the organic layer was dried with anhydrous magnesium sulfate. After distillation under reduced pressure, the product was recrystallized with ethanol to prepare Compound 8-2 (17.4 g, 69%).

MS: $[M+H]^+$=642

3) Preparation of Compound 8

Compound 8-2 (17.4 g, 27.1 mmol) and 2-chloro-4,6-diphenyl-1,3,5-trazine (8.7 g, 32.6 mmol) were added to 200 ml of tetrahydrofuran under a nitrogen atmosphere, and the mixture was stirred and refluxed. Then, potassium carbonate (11.3 g, 81.4 mmol) was added to and dissolved in 30 ml of water and sufficiently stirred, to which tetrakistriphenylphosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 8 (10.5 g, 52%).

MS: [M+H]$^+$=747

Preparation Example 9: Preparation of Compound 9

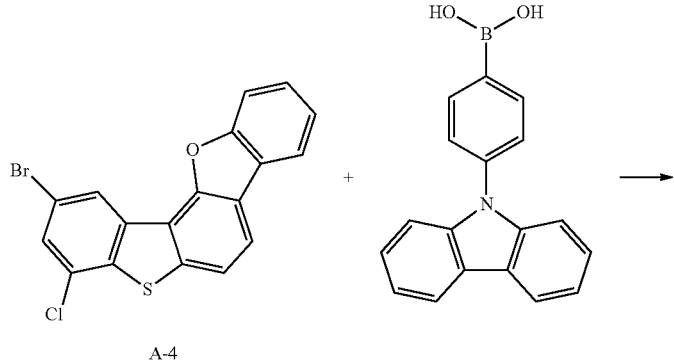

A-4

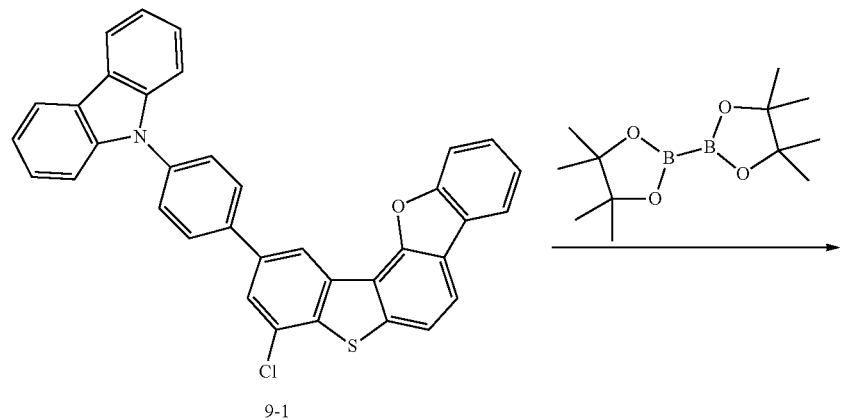

9-1

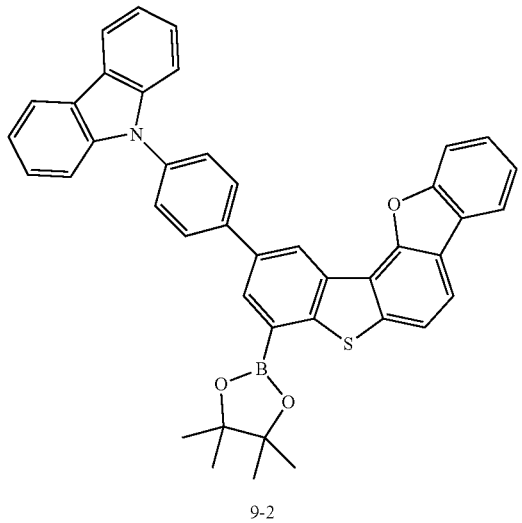

9-2

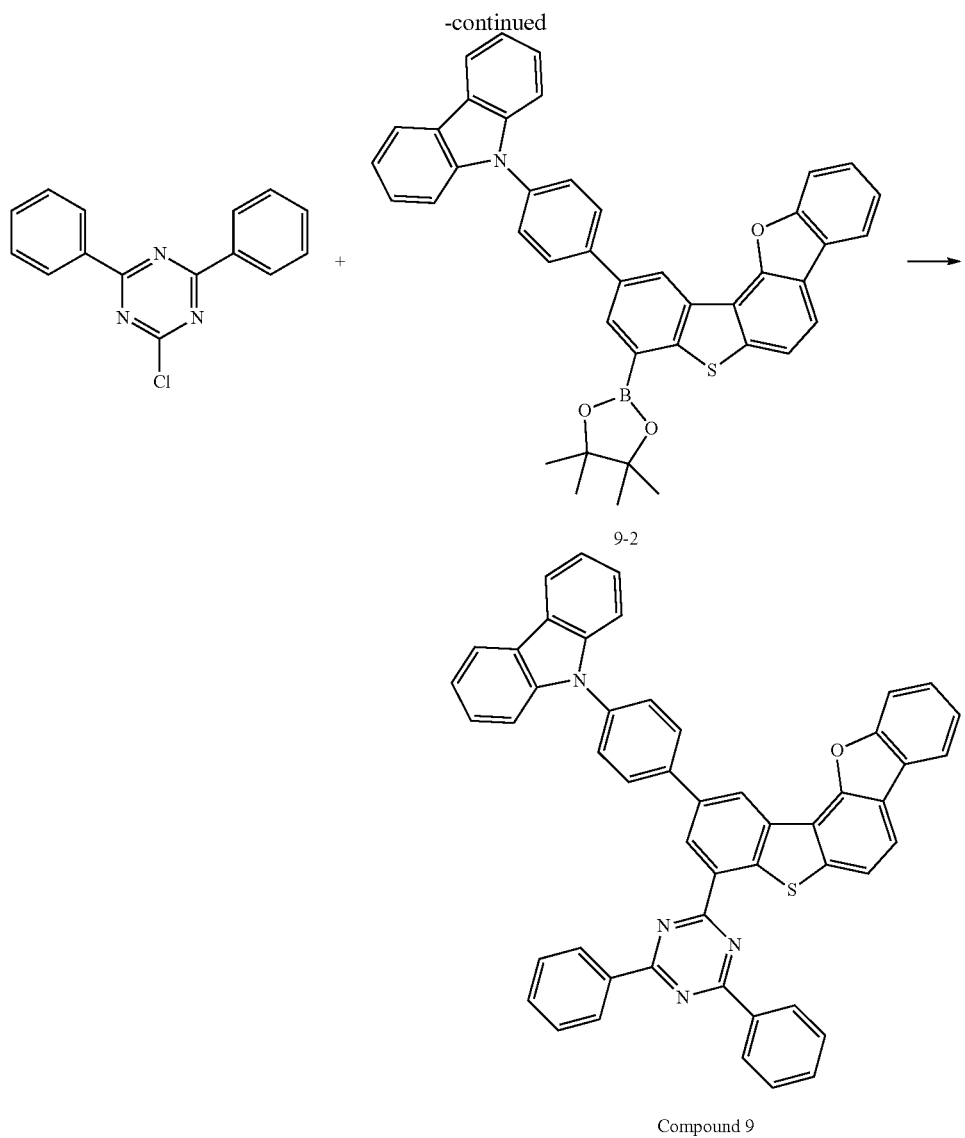

Compound 9

1) Preparation of Compound 9-1

The compound A-4 (20.0 g, 51.8 mmol) prepared in Preparation Example A and (4-(9H-carbazol-9-yl)phenyl)boronic acid (16.4 g, 62.2 mmol) were added to 200 mL of tetrahydrofuran and dissolved. Potassium carbonate (21.5 g, 103.7 mmol) was dissolved in water and added, and the mixture was heated. Tetrakistriphenyl-phosphinopalladium (1.8 g, 3 mol %) was added thereto, and the mixture was stirred under reflux for 12 hours. When the reaction was completed, the temperature was lowered to room temperature and the produced solid was filtered. The solid was dissolved in 700 mL of chloroform and washed twice with water. The organic layer was separated, and anhydrous magnesium sulfate was added thereto. The mixture was stirred and then filtered, and the filtrate was distilled under reduced pressure. The concentrated compound was purified through a silica column using chloroform and ethyl acetate to prepare a pale green solid compound 9-1 (19.6 g, 69%).

MS: $[M+H]^+$=550

2) Preparation of Compound 9-2

The compound 9-1 (19.6 g, 35.7 mmol), bis(pinacolato)diboron (10.0 g, 39.3 mmol), and potassium acetate (7.0 g, 71.4 mmol) were mixed under a nitrogen atmosphere, to which 200 ml of dioxane was added and heated while stirring. Bis(dibenzylideneacetone)palladium (0.6 g, 1.1 mmol) and tricyclohexylphosphine (0.6 g, 2.2 mmol) were added under a reflux condition, and the mixture was heated and stirred for 4 hours. After completion of the reaction, the reaction mixture was cooled to room temperature and then filtered. Water was poured into the filtrate, extracted with chloroform, and the organic layer was dried over anhydrous magnesium sulfate. After distillation under reduced pressure, the product was recrystallized with ethanol to prepare Compound 9-2 (16.7 g, 73%).

MS: $[M+H]^+$=642

3) Preparation of Compound 9

Compound 9-2 (16.7 g, 26.0 mmol) and 2-chloro-4,6-diphenyl-1,3,5-triazine (8.3 g, 31.3 mmol) were added to 200 ml of tetrahydrofuran under a nitrogen atmosphere, and the mixture was stirred and refluxed. Then, potassium carbonate (10.8 g, 78.1 mmol) was added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 9 (12.8 g, 66%).

MS: $[M+H]^+=747$

Preparation Example 10: Preparation of Compound 10

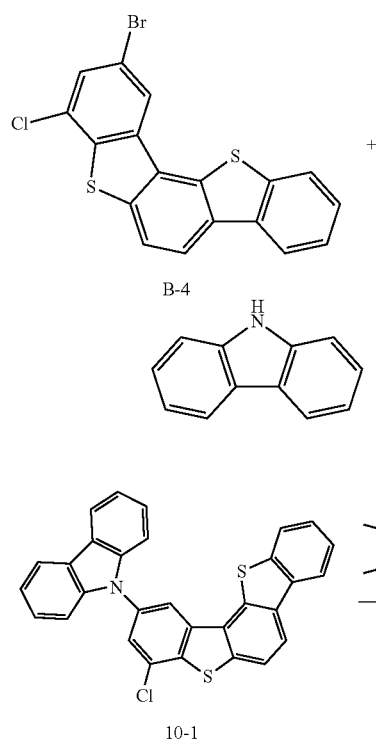

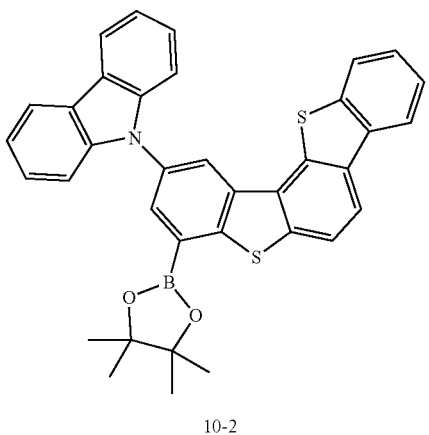

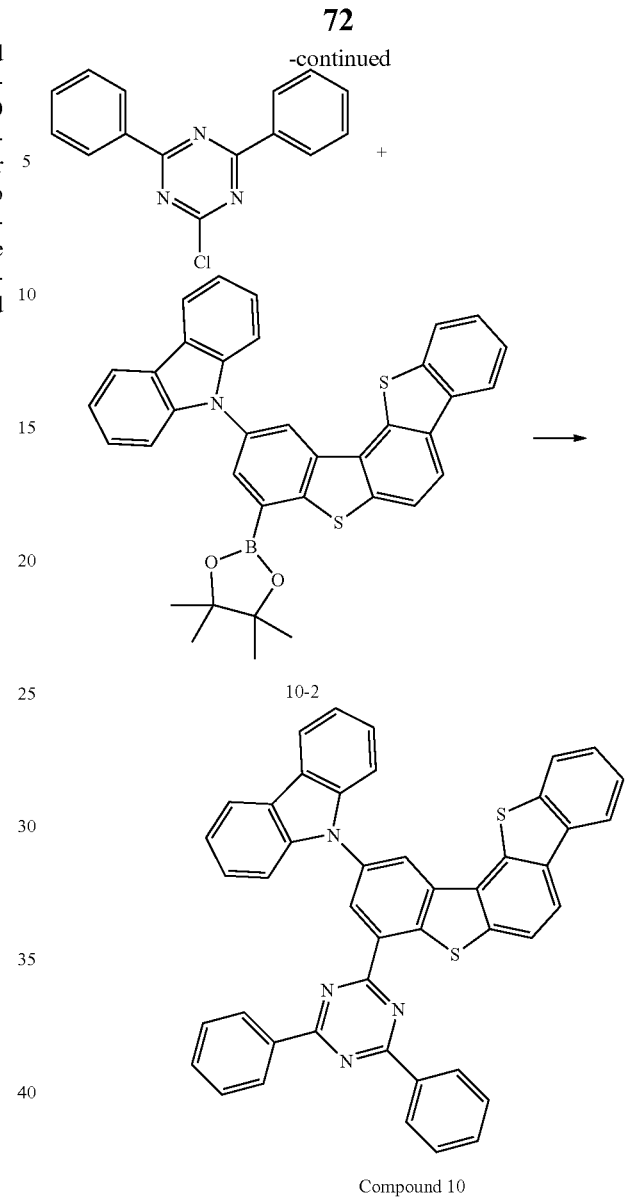

1) Preparation of Compound 10-1

The compound B4 (20.0 g, 49.8 mmol) prepared in Preparation Example B and 9H-carbazol (10.0 g, 59.7 mmol) were added to and dissolved in 100 mL of xylene, and then sodium tert-butoxide (13.8 g, 99.5 mmol) was added and heated. Bis(tri-tert-butylphosphine)palladium (0.8 g, 3 mol %) was added thereto, and the mixture was stirred under reflux for 12 hours. When the reaction was completed, the temperature was lowered to room temperature and the produced solid was filtered. The solid was dissolved in 700 mL of chloroform and washed twice with water. The organic layer was separated, and anhydrous magnesium sulfate was added thereto. The mixture was stirred and then filtered, and the filtrate was distilled under reduced pressure. The concentrated compound was purified through a silica column using chloroform and ethyl acetate to prepare a pale green solid compound 10-1 (16.5 g, 68%).

MS: $[M+H]^+=490$

2) Preparation of Compound 10-2

The compound 10-1 (16.5 g, 33.7 mmol), bis(pinacolato)diboron (9.4 g, 37.1 mmol) and potassium acetate (6.6 g, 67.5 mmol) were mixed under a nitrogen atmosphere, to which 200 ml of dioxane was added and heated while stirring. Bis(dibenzylideneacetone)palladium (0.6 g, 1.0 mmol) and tricyclohexylphosphine (0.6 g, 2.0 mmol) were added under a reflux condition, and the mixture was heated and stirred for 3 hours. After completion of the reaction, the reaction mixture was cooled to room temperature and then filtered. Water was poured into the filtrate, extracted with chloroform, and the organic layer was dried with anhydrous magnesium sulfate. After distillation under reduced pressure, the product was recrystallized with ethanol to prepare Compound 10-2 (14.5 g, 74%).

MS: [M+H]$^+$=582

3) Preparation of Compound 10

Compound 10-2 (14.5 g, 24.9 mmol) and 2-chloro-4,6-diphenyl-1,3,5-triazine (8.0 g, 29.9 mmol) were added to 200 ml of tetrahydrofuran under a nitrogen atmosphere, and the mixture was stirred and refluxed. Then, potassium carbonate (10.3 g, 74.8 mmol) was added to and dissolved in 30 ml of water and sufficiently stirred, to which tetrakistriphenyl-phosphinopalladium (0.9 g, 3 mol %) was added. After reaction for 4 hours, the reaction mixture was cooled to room temperature and then filtered. The filtrate was dissolved in chloroform, extracted with water, and then the organic layer was dried with magnesium sulfate. Subsequently, the organic layer was dried, and then recrystallized with ethyl acetate to prepare Compound 10 (12.3 g, 72%).

MS: [M+H]$^+$=687

Example 1: Preparation of Organic Light Emitting Device

A glass substrate on which ITO (indium tin oxide) was coated as a thin film to a thickness of 1300 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the ITO transparent electrode thus prepared, the following compound HI-1 was thermally vacuum deposited to a thickness of 50 Å to form a hole injection layer. The following compound HT-1 was thermally vacuum deposited on the hole injection layer to a thickness of 250 Å to form a hole transport layer, and the following compound HT-2 was vacuum deposited on the HT-1 deposited film to a thickness of 50 Å to form an electron blocking layer.

The compound 1 prepared in the previous Preparation Example 1, the following compound YGH-1, and a phosphorescent dopant YGD-1 were co-deposited at a weight ratio of 44:44:12 on the HT-2 deposited film to form a light emitting layer with a thickness of 400 Å.

The following compound ET-1 was vacuum deposited on the light emitting layer to a thickness of 250 Å to form an electron transport layer, and the following compound ET-2 and Li were vacuum deposited at a weight ratio of 98:2 to form an electron injection layer with a thickness of 100 Å.

Aluminum was deposited on the electron injection layer to a thickness of 1000 Å to form a cathode.

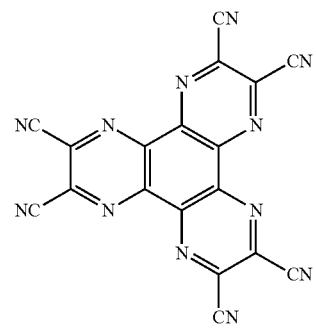

HI-1

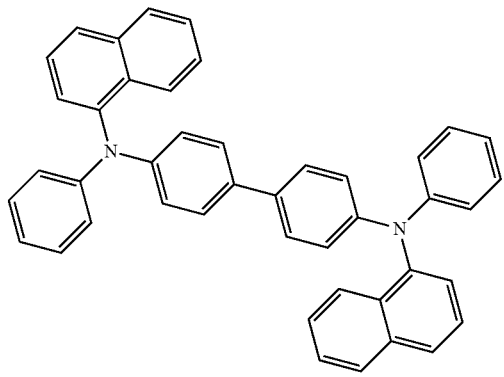

HT-1

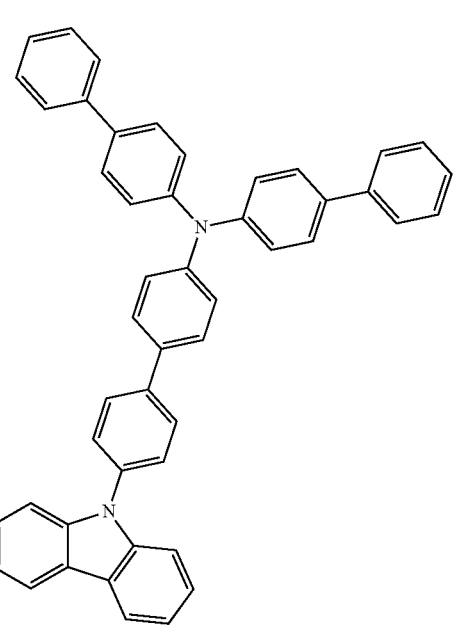

HT-2

YGH-1

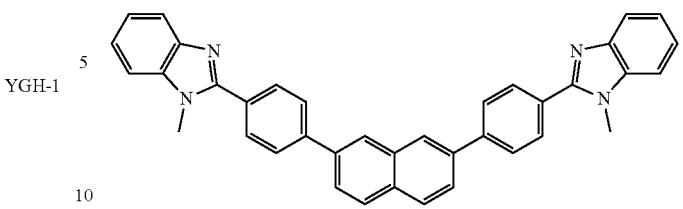
ET-2

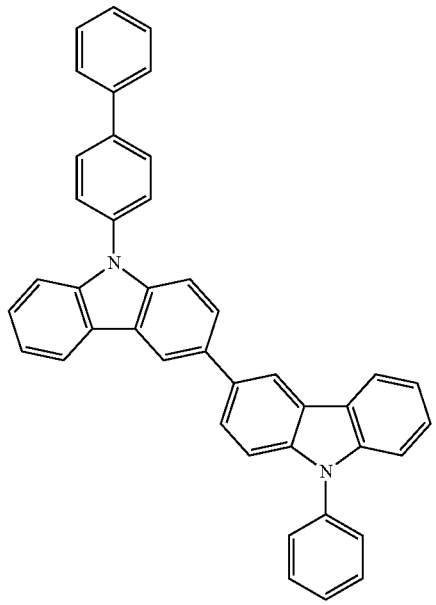

In the above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1 \times 10^{-7}$ to $5 \times 10^{-8}$ torr.

Examples 2 to 10

An organic light emitting device was manufactured in the same manner as in Example 1, except that the compounds shown in Table 1 below were used instead of Compound 1 of Preparation Example 1.

The structures of the compounds used in the examples are as follows:

YGD-1

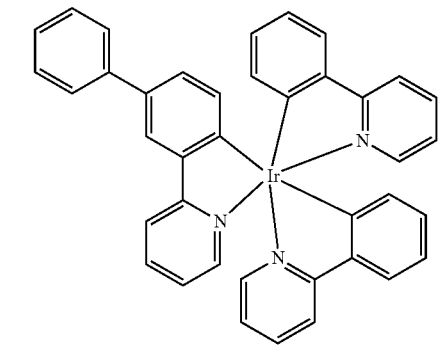

Compound 1

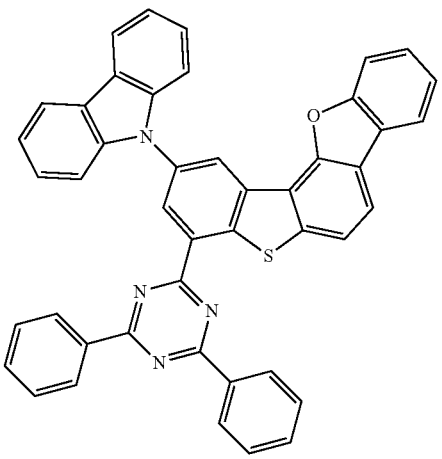

ET-1

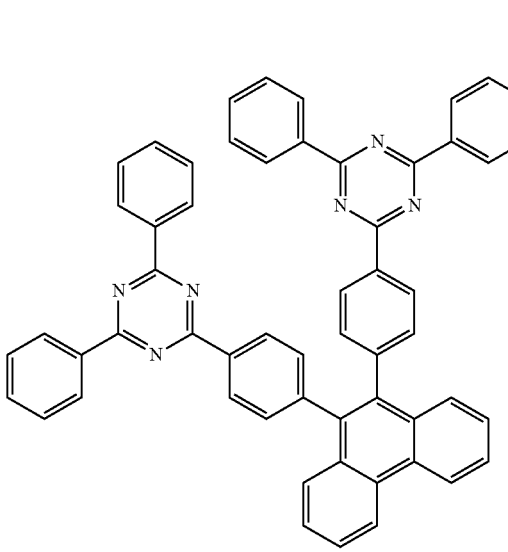

Compound 2

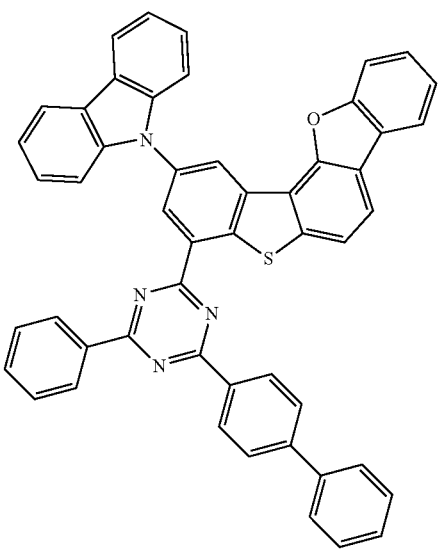

Compound 3
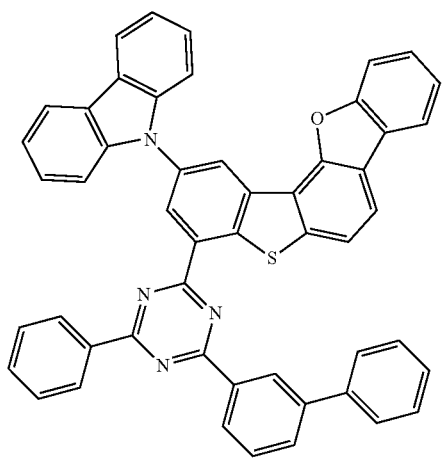
Compound 4
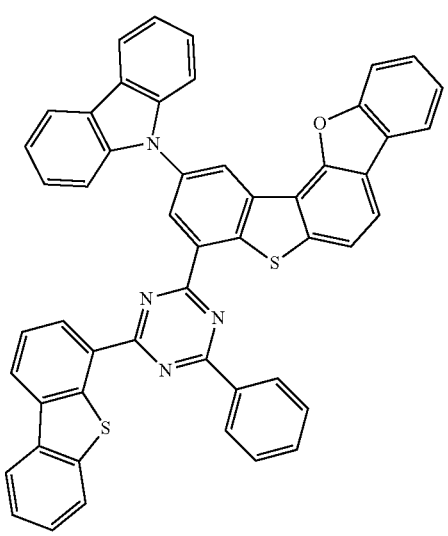
Compound 5
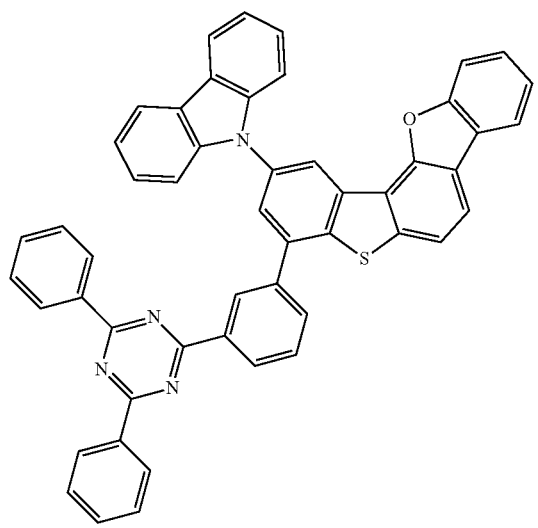
Compound 6
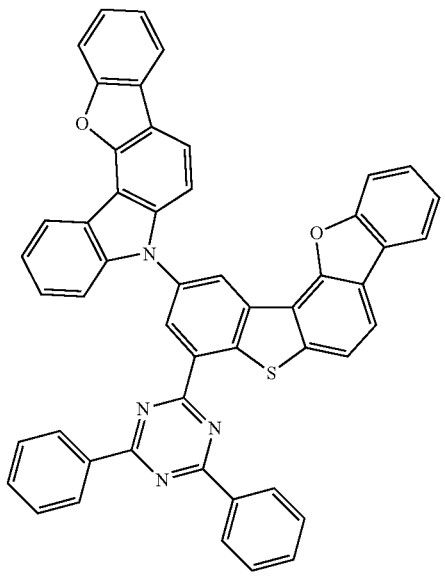
Compound 7
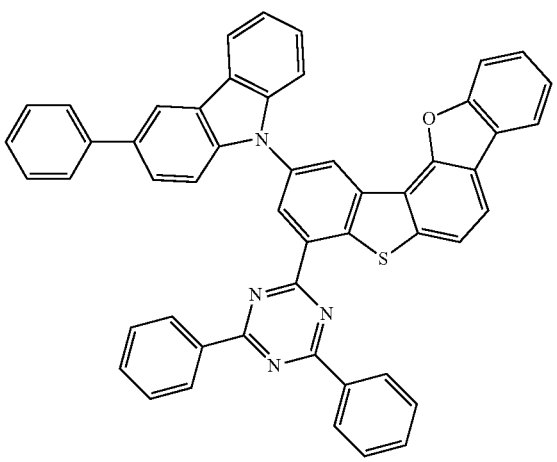
Compound 8
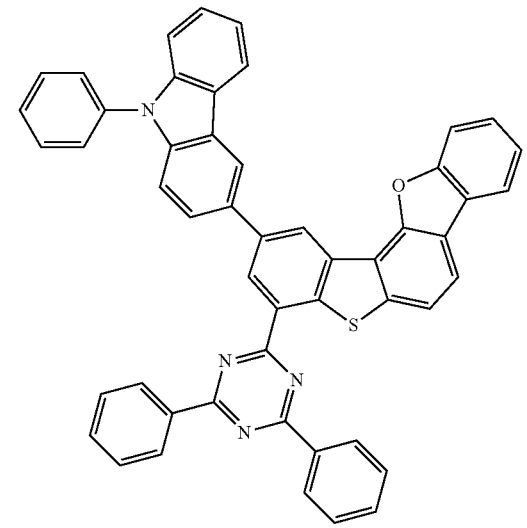

-continued

Compound 9

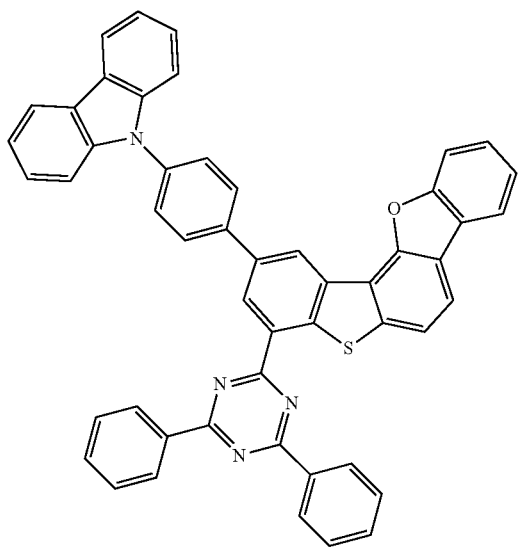

Compound 10

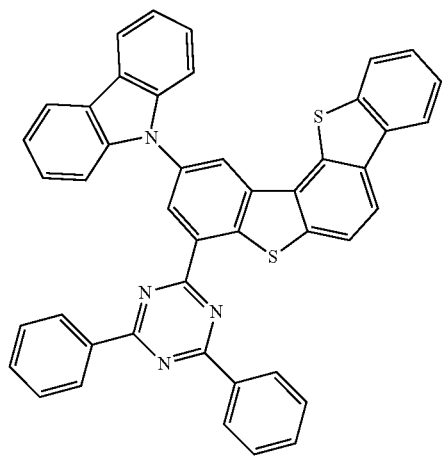

Comparative Examples 1 to 4

An organic light emitting device was manufactured in the same manner as in Example 1, except that the compounds shown in Table 1 below were used instead of Compound 1 of Preparation Example 1. The structures of the compounds CE1, CE2, CE3, and CE4 used in Table 1 below are as follows.

CE1

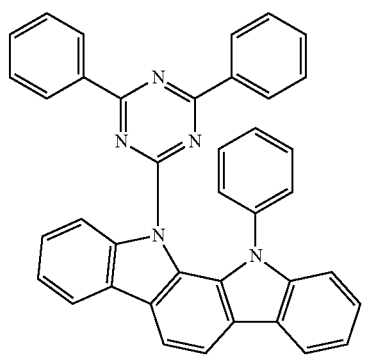

-continued

CE2

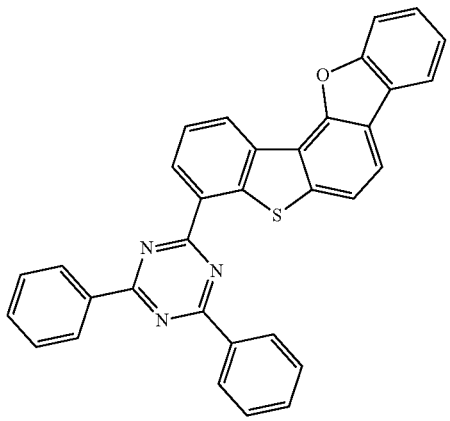

CE3

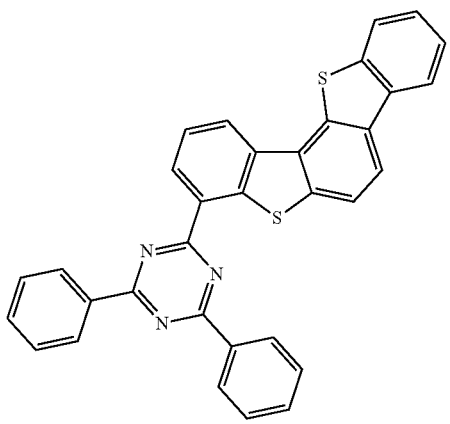

CE4

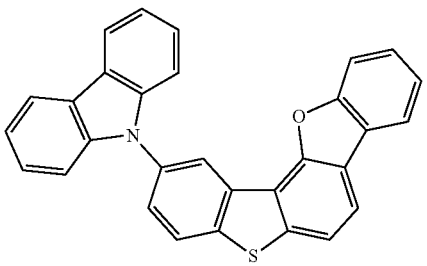

Experimental Example 1

The voltage and efficiency at current density of 10 mA/cm$^2$, the color coordinates, and the lifetime (LT$_{95}$) at a current density of 50 mA/cm$^2$ were measured by applying a current to the organic light emitting devices manufactured in the examples and comparative examples above, and the results are shown in Table 1 below. At this time, the lifetime (LT$_{95}$) means the time required for the luminance to be reduced to 95% of the initial luminance.

TABLE 1

| | Compound (Light emitting layer host) | Voltage (V) (@10 mA/cm$^2$) | Efficiency (Cd/A) (@10 mA/cm$^2$) | Color coordinates (x, y) | Lifetime (h) (LT$_{95}$, @50 mA/cm$^2$) |
|---|---|---|---|---|---|
| Example 1 | Compound 1 | 3.9 | 82 | 0.45, 0.53 | 184 |
| Example 2 | Compound 2 | 3.9 | 81 | 0.46, 0.53 | 180 |
| Example 3 | Compound 3 | 3.8 | 82 | 0.46, 0.54 | 194 |
| Example 4 | Compound 4 | 3.7 | 80 | 0.46, 0.54 | 220 |
| Example 5 | Compound 5 | 4.0 | 84 | 0.46, 0.53 | 135 |
| Example 6 | Compound 6 | 4.0 | 80 | 0.46, 0.54 | 195 |
| Example 7 | Compound7 | 3.9 | 82 | 0.46, 0.54 | 187 |
| Example 8 | Compound 8 | 3.9 | 83 | 0.46, 0.54 | 184 |
| Example 9 | Compound 9 | 4.1 | 81 | 0.46, 0.53 | 125 |
| Example 10 | Compound 10 | 4.2 | 79 | 0.46, 0.54 | 120 |
| Comparative Example 1 | CE1 | 4.5 | 70 | 0.46, 0.54 | 90 |
| Comparative Example 2 | CE2 | 4.0 | 79 | 0.46, 0.55 | 100 |
| Comparative Example 3 | CE3 | 4.2 | 78 | 0.46, 0.55 | 60 |
| Comparative Example 4 | CE4 | 5.1 | 62 | 0.44, 0.61 | 45 |

As shown in Table 1, it was confirmed that the organic light emitting device using the compound of the present invention as a host material in the light emitting layer exhibited significantly improved lifetime characteristics while having an equivalent level of efficiency, as compared with an organic light emitting device using a material of the comparative examples as a host material in the light emitting layer.

This is considered to be because, in the case of a compound having a structure in which a triazine-based substituent and a carbazole-based substituent are simultaneously bonded to a benzofurodibenzothiophene or benzothienodibenzothiophene core, it has increased charge stability compared to compounds having a structure in which only one of these substituents is bonded.

| <Description of symbols> |
|---|
| 1: substrate |
| 2: anode |
| 3: light emitting layer |
| 4: cathode |
| 5: hole injection layer |
| 6: hole transport layer |
| 7: electron blocking layer |
| 8: electron transport layer |
| 9: electron injection layer |

What is claimed is:

1. A compound of Chemical Formula 1:

Chemical Formula 1

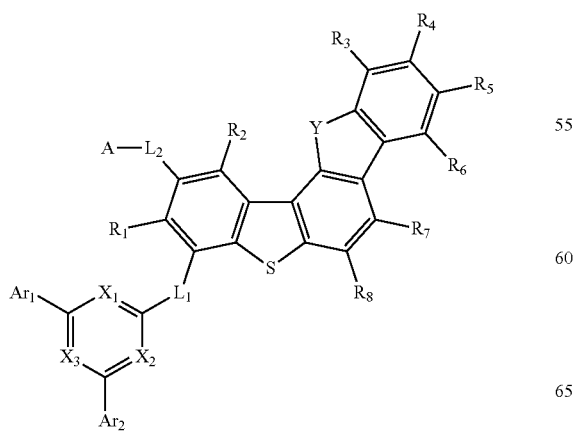

wherein, in Chemical Formula 1:
$X_1$ to $X_3$ are each independently N or CH, provided that at least two of $X_1$ to $X_3$ are N;
Y is O or S;
$L_1$ and $L_2$ are each independently a single bond, a substituted or unsubstituted $C_{6-60}$ arylene, or a substituted or unsubstituted $C_{2-60}$ heteroarylene containing one or more heteroatoms selected from the group consisting of O, N, Si, and S; and
A is one of the following Chemical Formula 2 or 3:

[Chemical Formula 2]

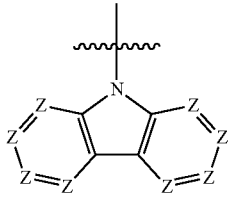

[Chemical Formula 3]

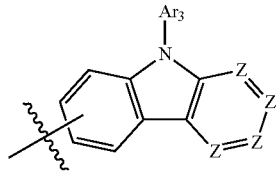

wherein, in Chemical Formulae 2 and 3:
each Z is independently CR, or two adjacent Zs are C that are linked to the following Chemical Formula 4 to form a fused ring, and the rest are each independently CR;

Chemical Formula 4

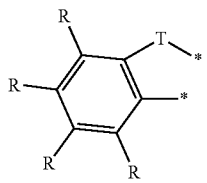

wherein, in Chemical Formula 4:

T is O, S, $CQ_1Q_2$, or $NAr_4$;

$Ar_1$ to $Ar_4$ are each independently a substituted or unsubstituted $C_{6-60}$ aryl or a substituted or unsubstituted $C_{2-60}$ heteroaryl containing one or more selected from the group consisting of N, O, and S;

R and $R_1$ to $R_8$ are each independently hydrogen, deuterium, a halogen, cyano, nitro amino a substituted or unsubstituted $C_{1-60}$ alkyl, a substituted or unsubstituted $C_{1-60}$ haloalkyl a substituted or unsubstituted $C_{1-60}$ alkoxy, a substituted or unsubstituted $C_{1-60}$ haloalkoxy, a substituted or unsubstituted $C_{3-60}$ cycloalkyl a substituted or unsubstituted $C_{2-60}$ alkenyl, a substituted or unsubstituted $C_{6-60}$ aryl, a substituted or unsubstituted $C_{6-60}$ aryloxyl, or a substituted or unsubstituted $C_{2-60}$ heteroaryl containing one or more heteroatoms selected from the group consisting of N, O, and S;

$Q_1$ and $Q_2$ are each independently hydrogen, deuterium, a halogen, cyano, nitro amino a substituted or unsubstituted $C_{1-60}$ alkyl, or a substituted or unsubstituted $C_{6-60}$ aryl; and

* indicates a point which is attached to two adjacent Z of Chemical Formula 2 or 3.

2. The compound according to claim 1,
wherein $L_1$ and $L_2$ are each independently a single bond, phenylene, or biphenylylene.

3. The compound according to claim 1,
wherein $Ar_1$ and $Ar_2$ are each independently phenyl, biphenyl, terphenylyl, naphthyl, phenanthrenyl, dibenzothiophenyl, or carbazolyl.

4. The compound according to claim 1,
wherein A is any one of Chemical Formulas 4a to 4n:

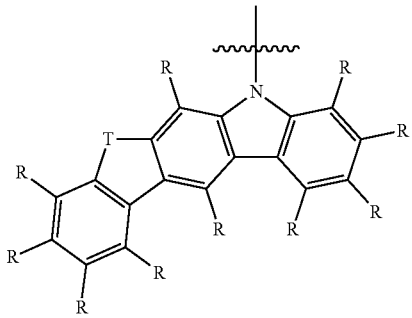

4a

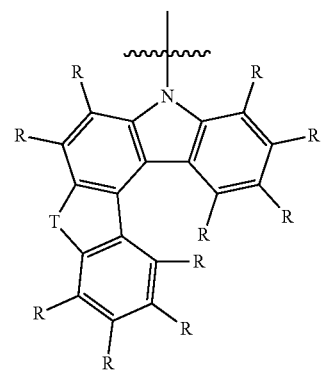

4b

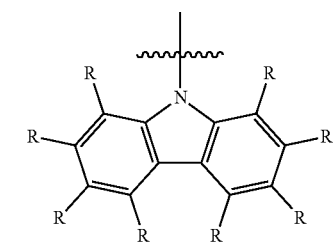

4c

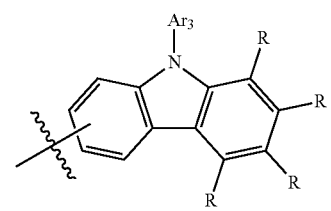

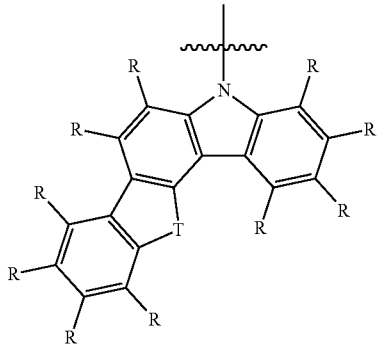

-continued

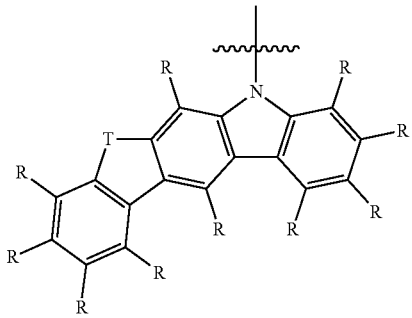

4d

4e

4f

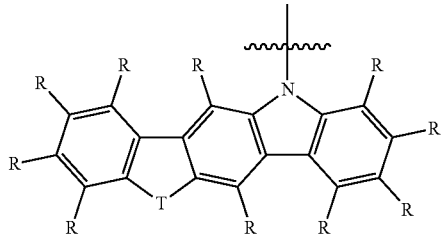

4g

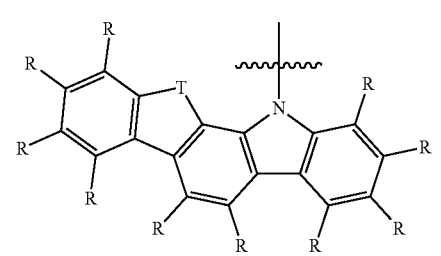

4h

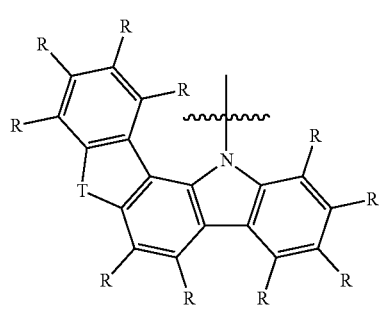

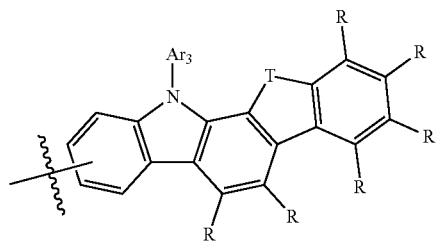
4i
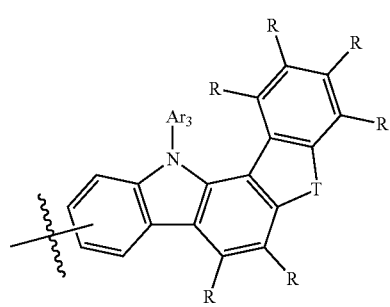
4j
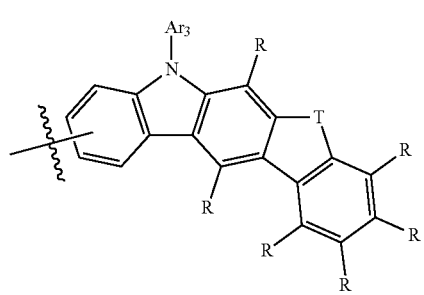
4k
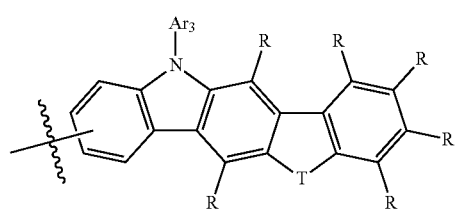
4l
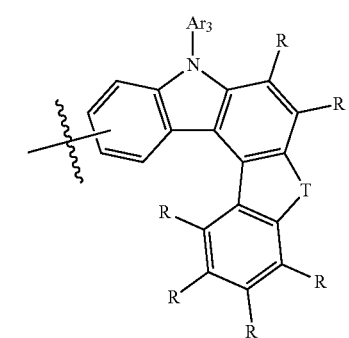
4m
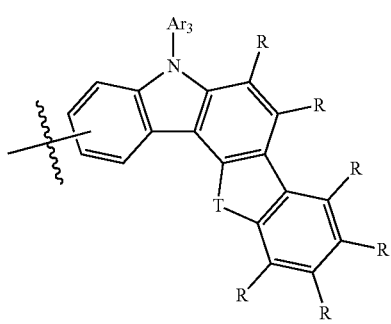
4n
wherein, in Chemical Formulas 4a to 4n:
T is O, S, $CQ_1Q_2$, or $NAr_4$;
$Ar_3$ and $Ar_4$ are each independently a $C_{6-20}$ aryl;
each R is independently hydrogen or a $C_{6-20}$ aryl; and
$Q_1$ and $Q_2$ are each independently hydrogen, a $C_{1-10}$ alkyl, or a $C_{6-20}$ aryl.
5. The compound according to claim 4,
wherein A is any one of Chemical Formulas 5a to 5l:
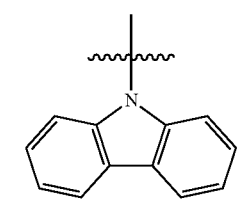
5a
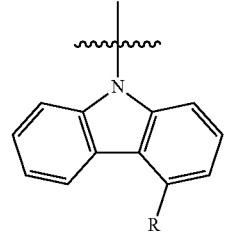
5b
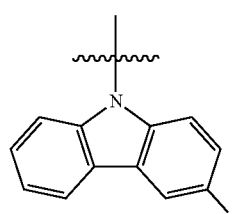
5c
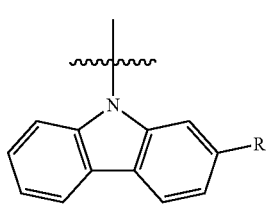
5d 5e 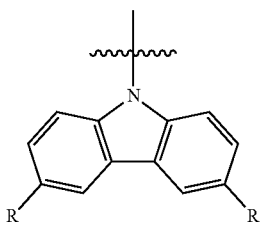

5f 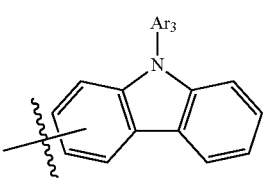

5g 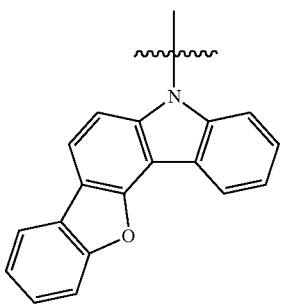

5h 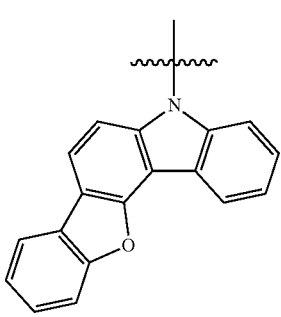

5i 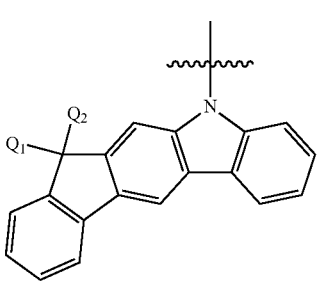

5j 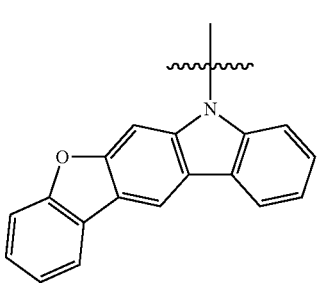

5k 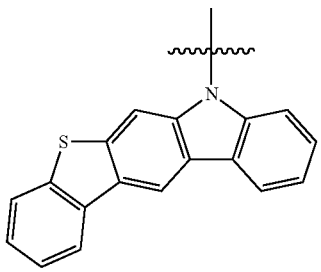

5l 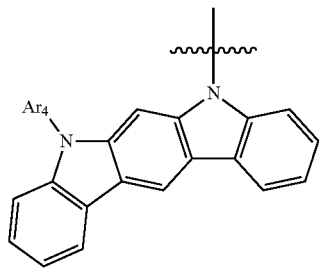

wherein, in Chemical Formulas 5a to 5l:
R, Ar$_3$, and Ar$_4$ are each independently a C$_{6\text{-}20}$ aryl; and
Q$_1$ and Q$_2$ are each independently a C$_{1\text{-}10}$ alkyl.

6. The compound according to claim 5, wherein:
R, Ar$_3$, and Ar$_4$ are phenyl; and
Q$_1$ and Q$_2$ are methyl.

7. The compound according to claim 1, wherein:
the compound is any one of Chemical Formulas 1-1 to 1-3:

Chemical Formula 1-1

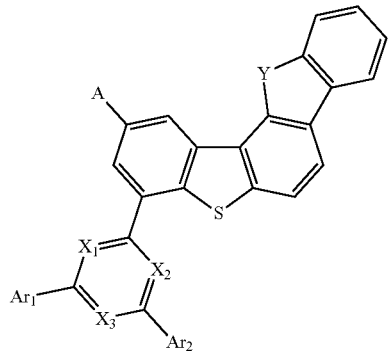

Chemical Formula 1-2

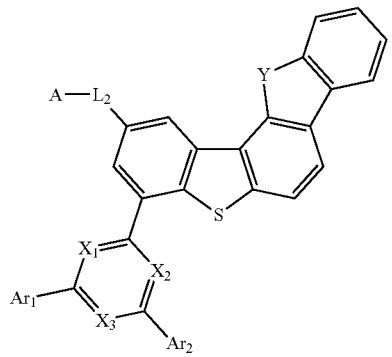

Chemical Formula 1-3

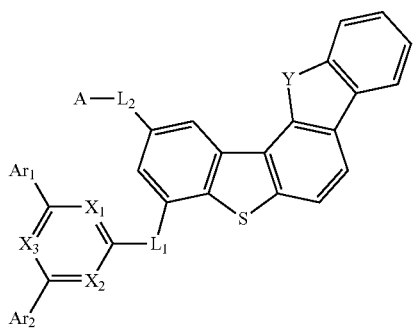

wherein, in Chemical Formulas 1-1 to 1-3:

$X_1$ to $X_3$, Y, A, $Ar_1$, and $Ar_2$ are the same as those defined in claim 1; and $L_1$ and $L_2$ are each independently a substituted or unsubstituted $C_{6-60}$ arylene, or a substituted or unsubstituted $C_{2-60}$ heteroarylene containing one or more heteroatoms selected from the group consisting of O, N, Si, and S.

8. The compound according to claim 1, wherein the compound is any one selected from the group consisting of the following compounds:

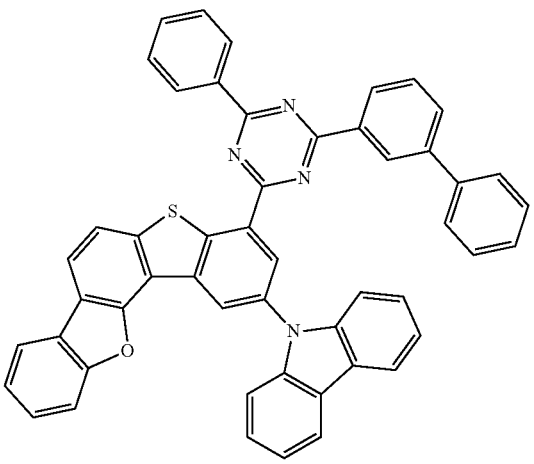

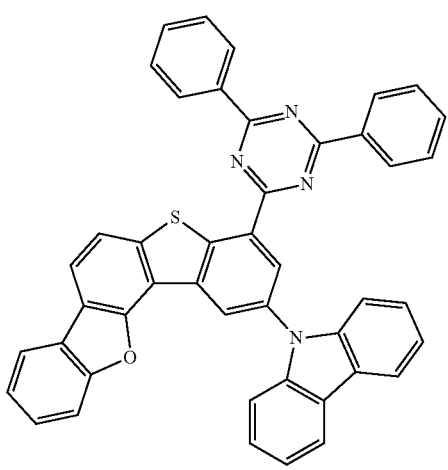

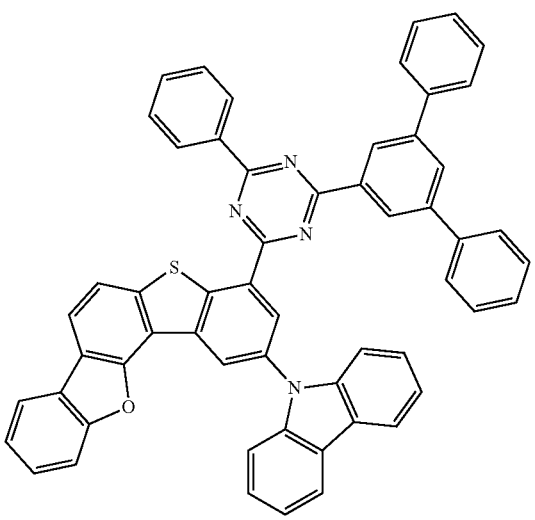

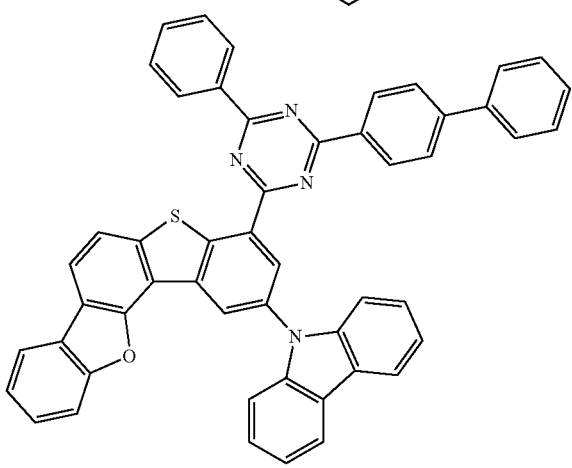

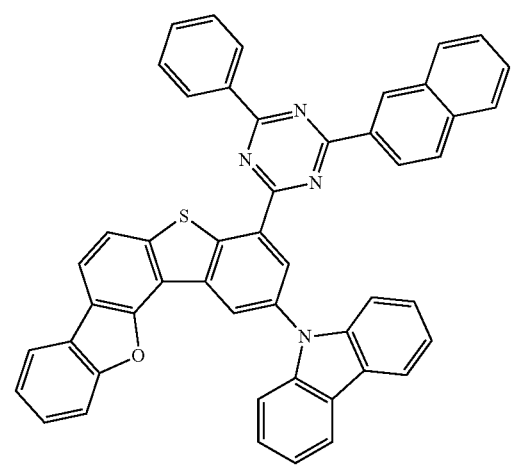

91
-continued
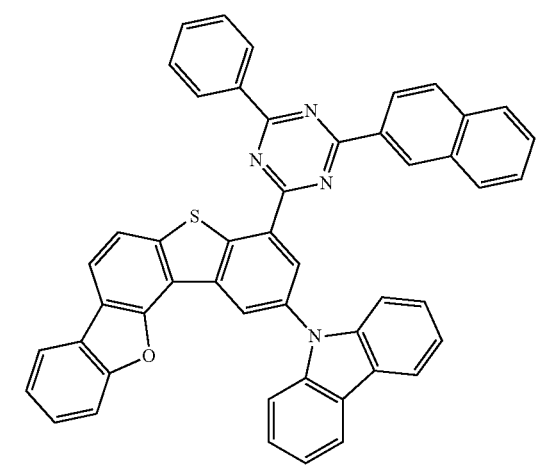
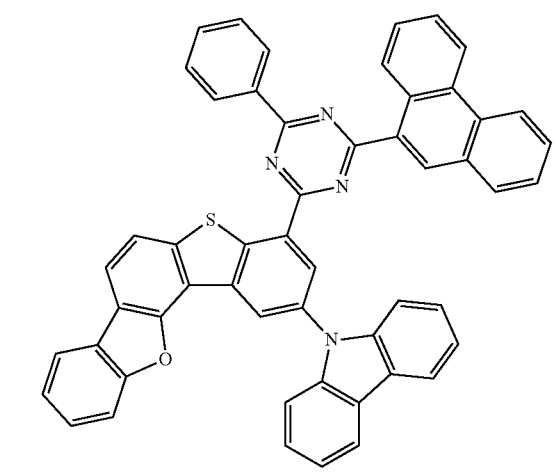
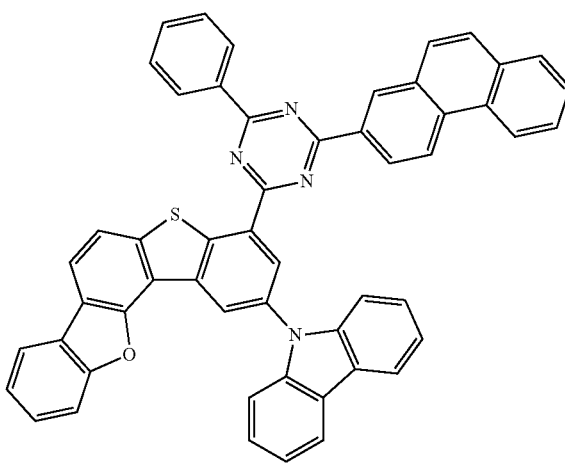
92
-continued
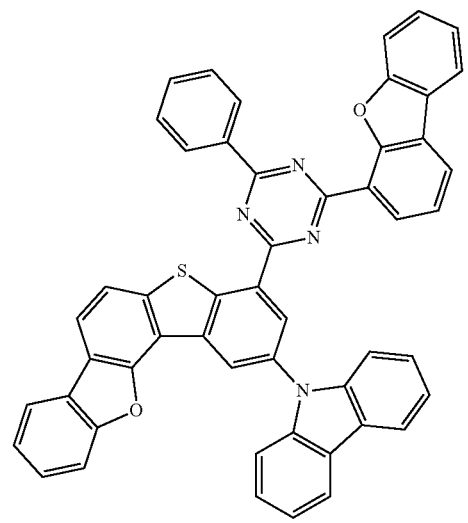
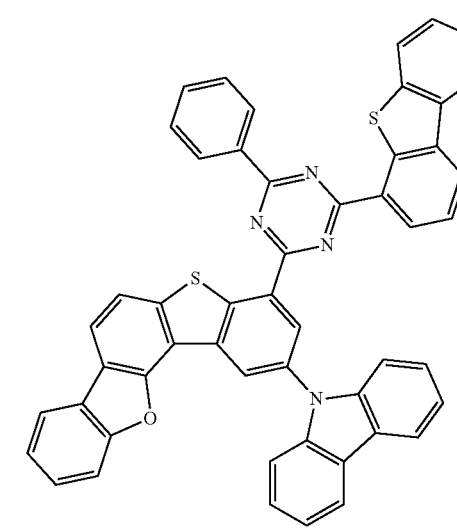
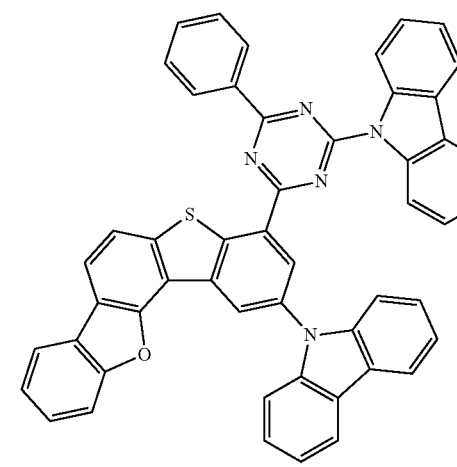

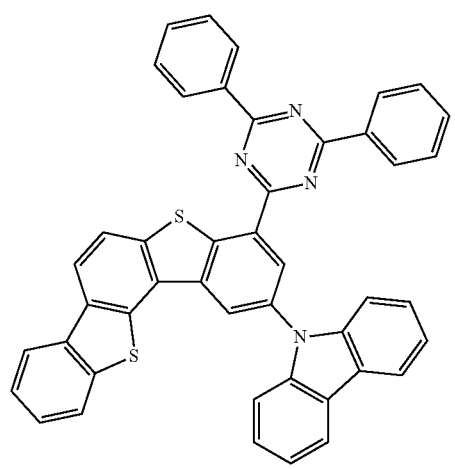
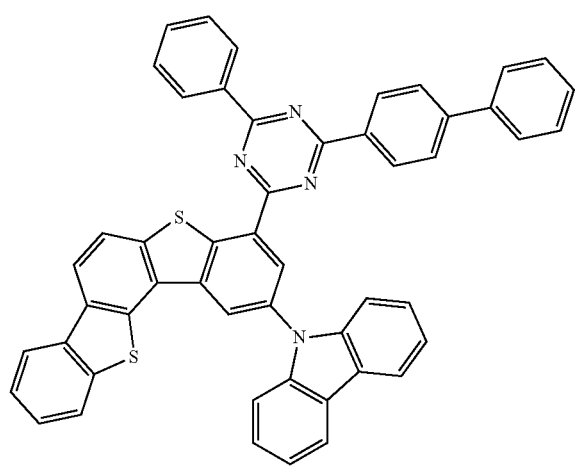
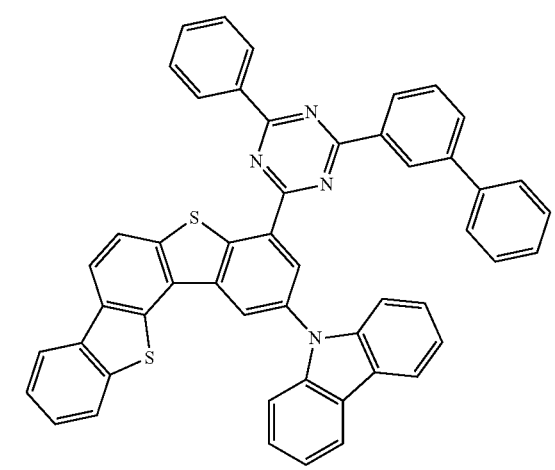
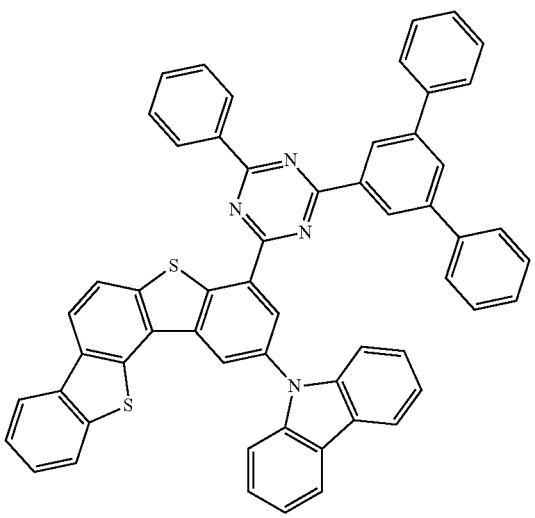
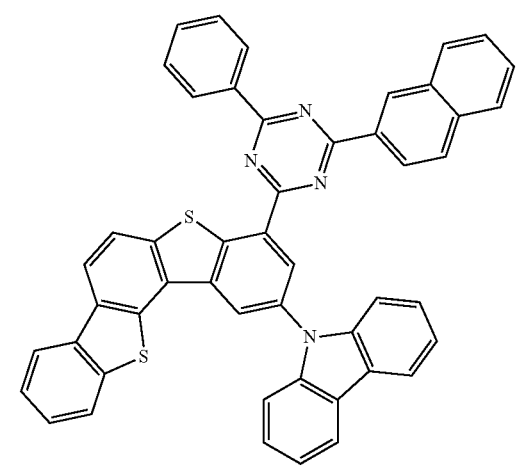
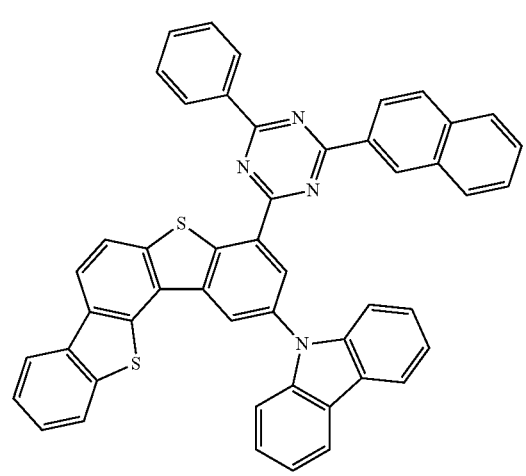

95
-continued
96
-continued
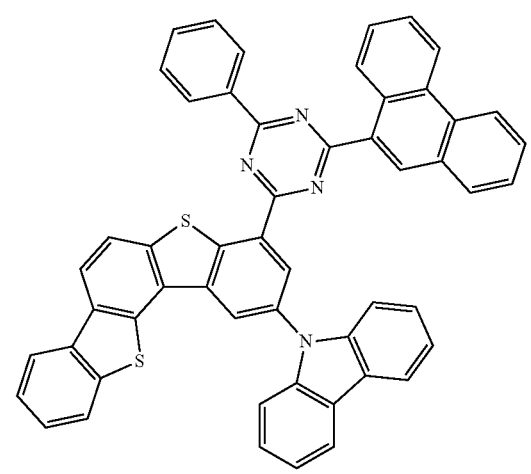
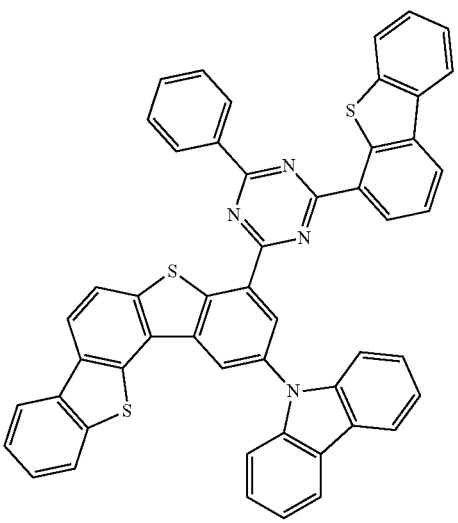
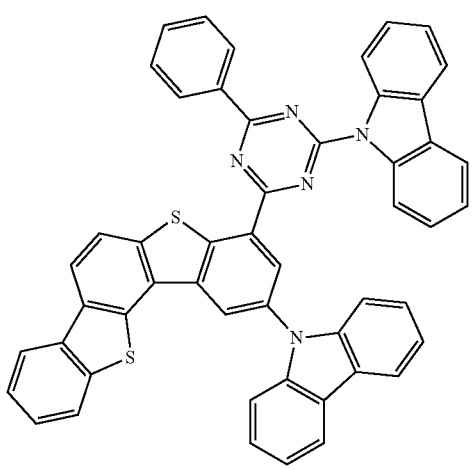 [SMILES: c1ccc(-c2nc(-c3cc(-n4c5ccccc5c5ccccc54)cc4c3sc3ccc5c6ccccc6sc5c34)nc(-n3c4ccccc4c4ccccc43)n2)cc1]
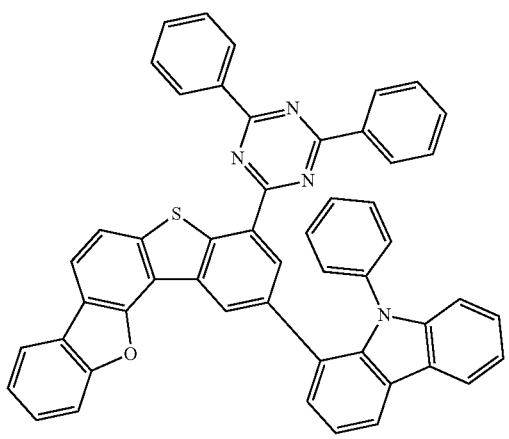

97
-continued
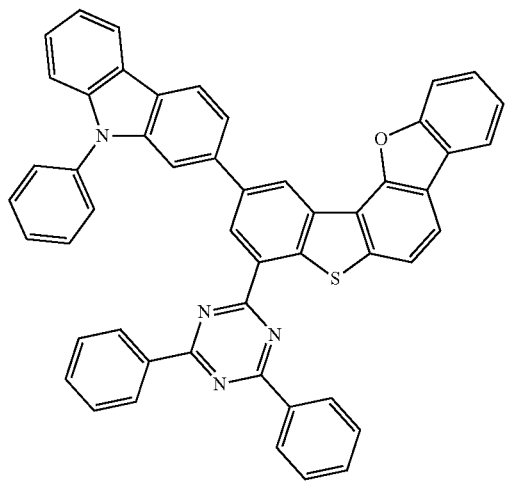
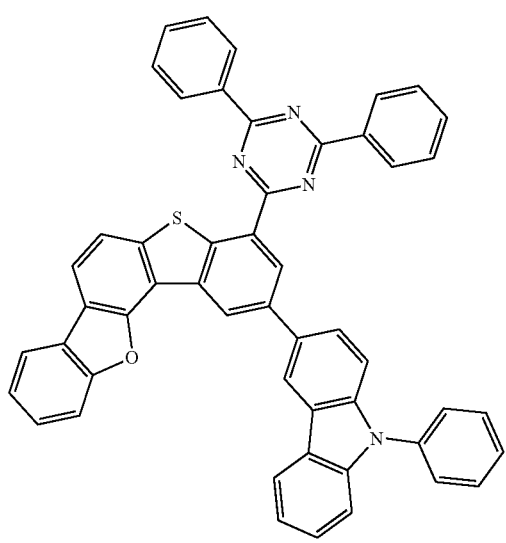
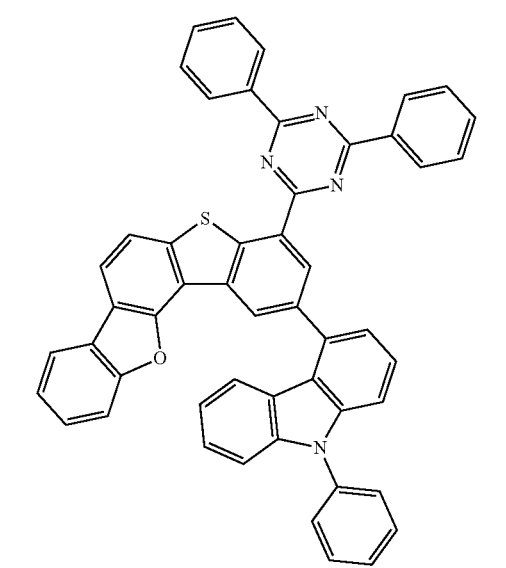
98
-continued
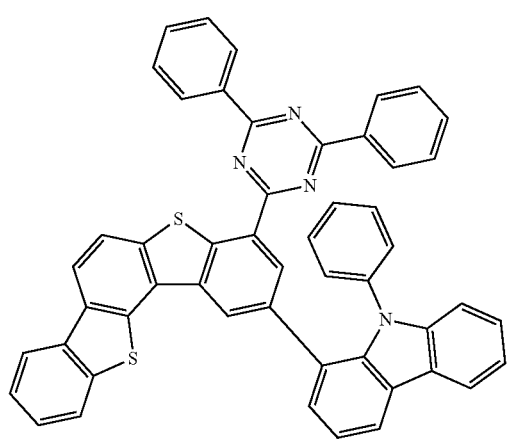
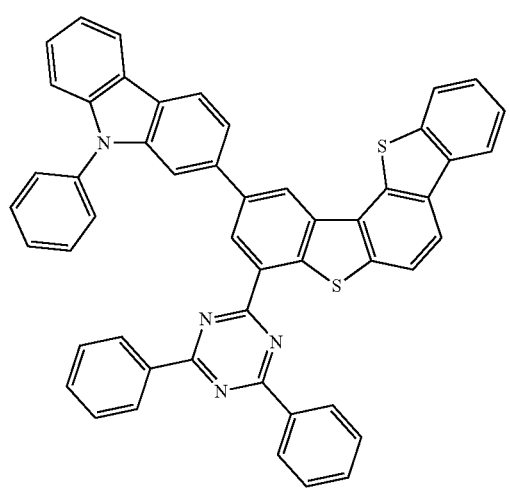
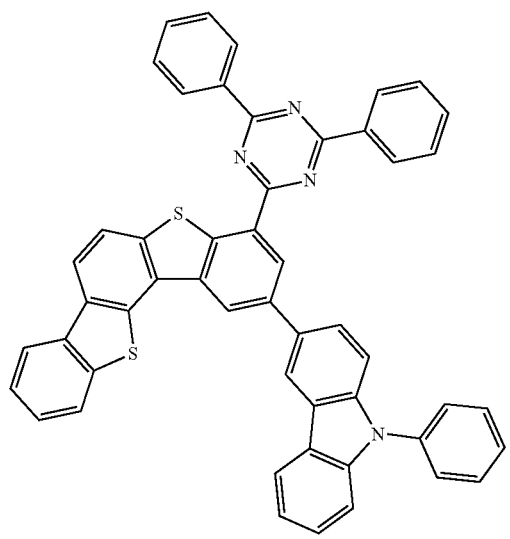

99
-continued
100
-continued
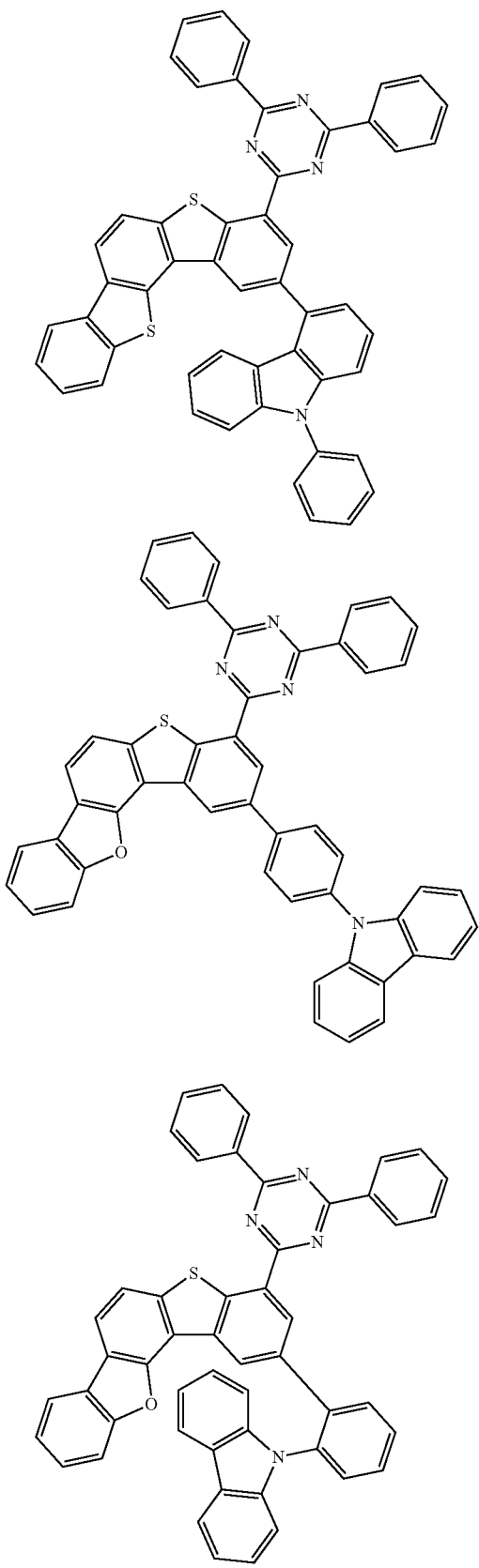
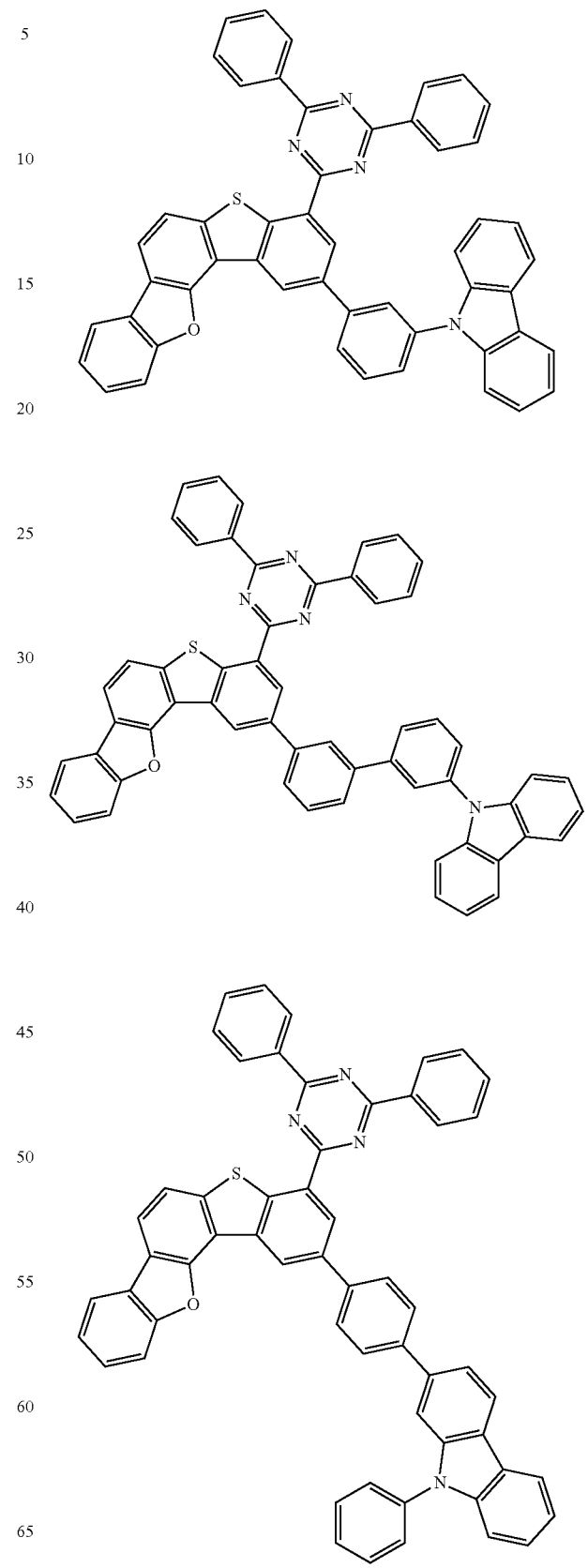

101
-continued
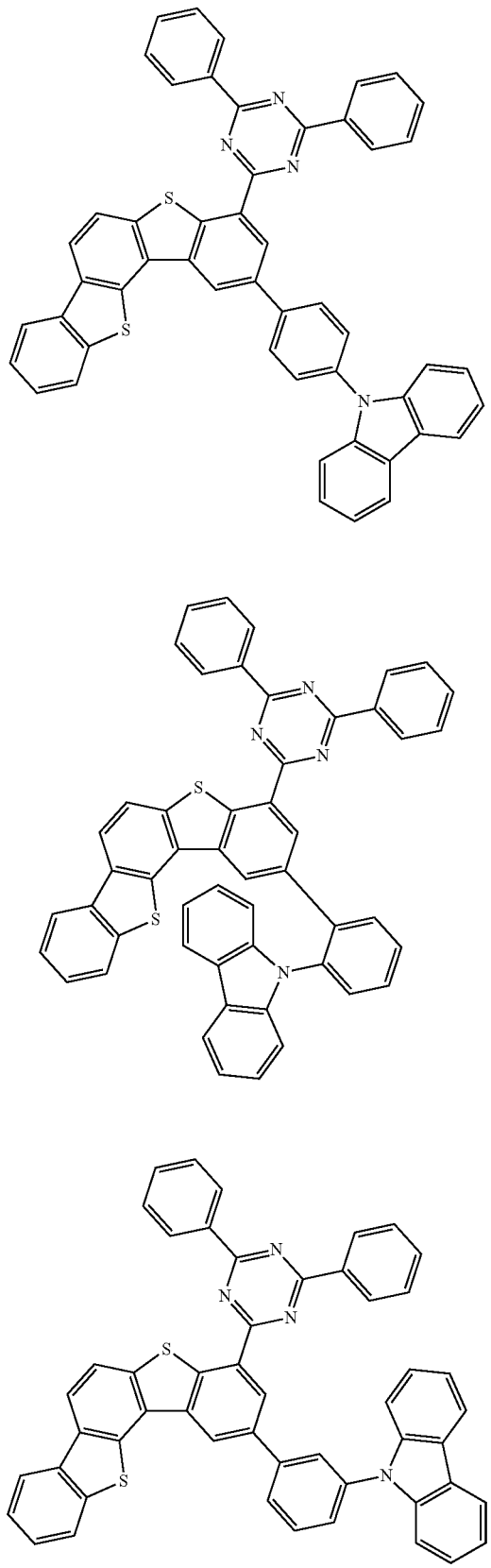
102
-continued
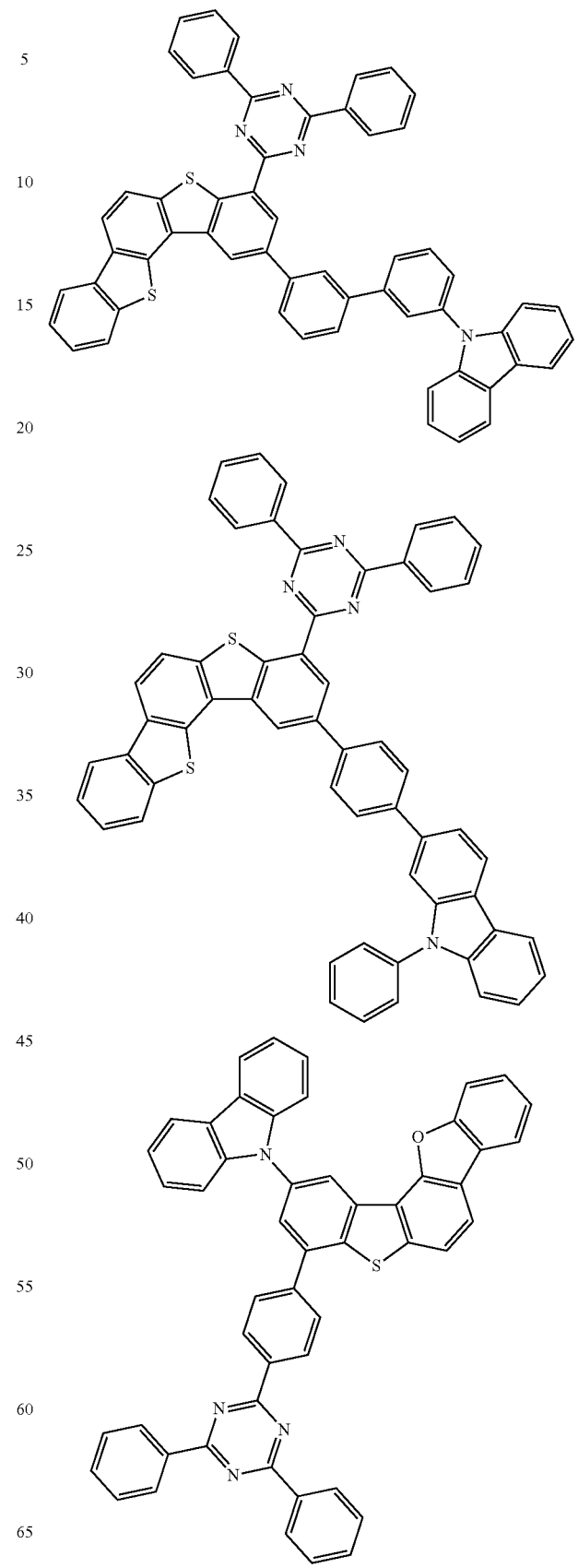

103
-continued
104
-continued
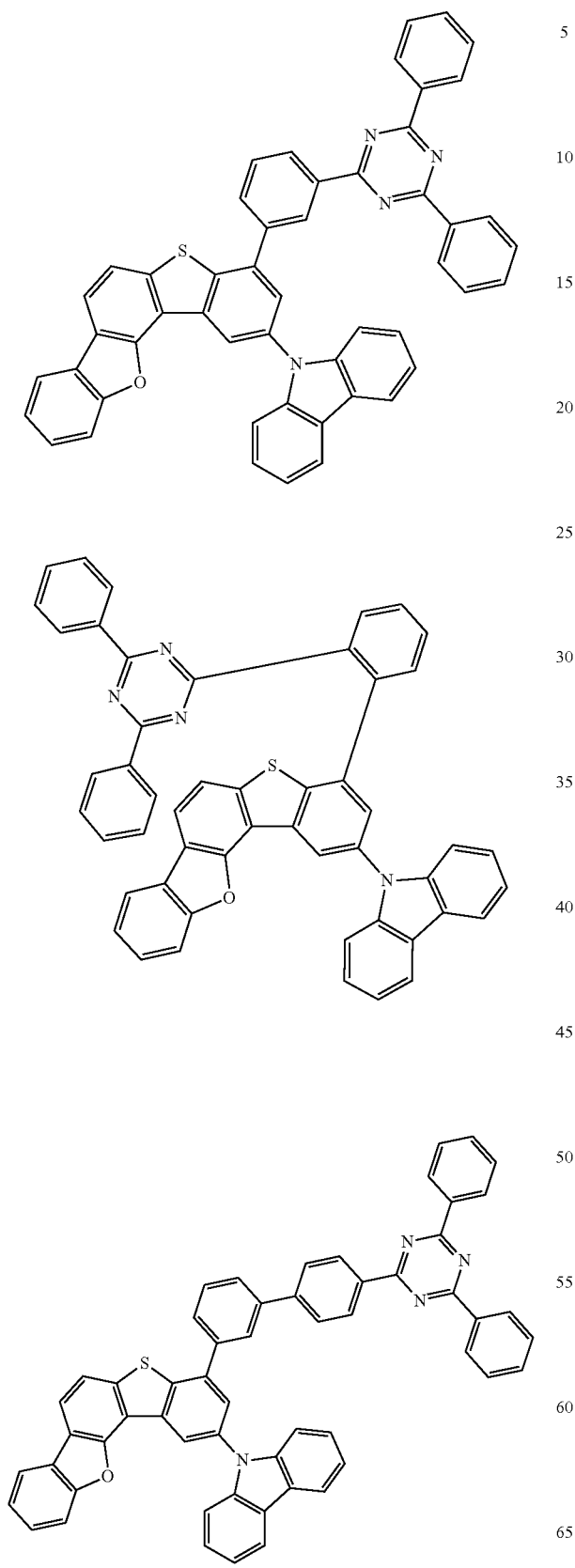
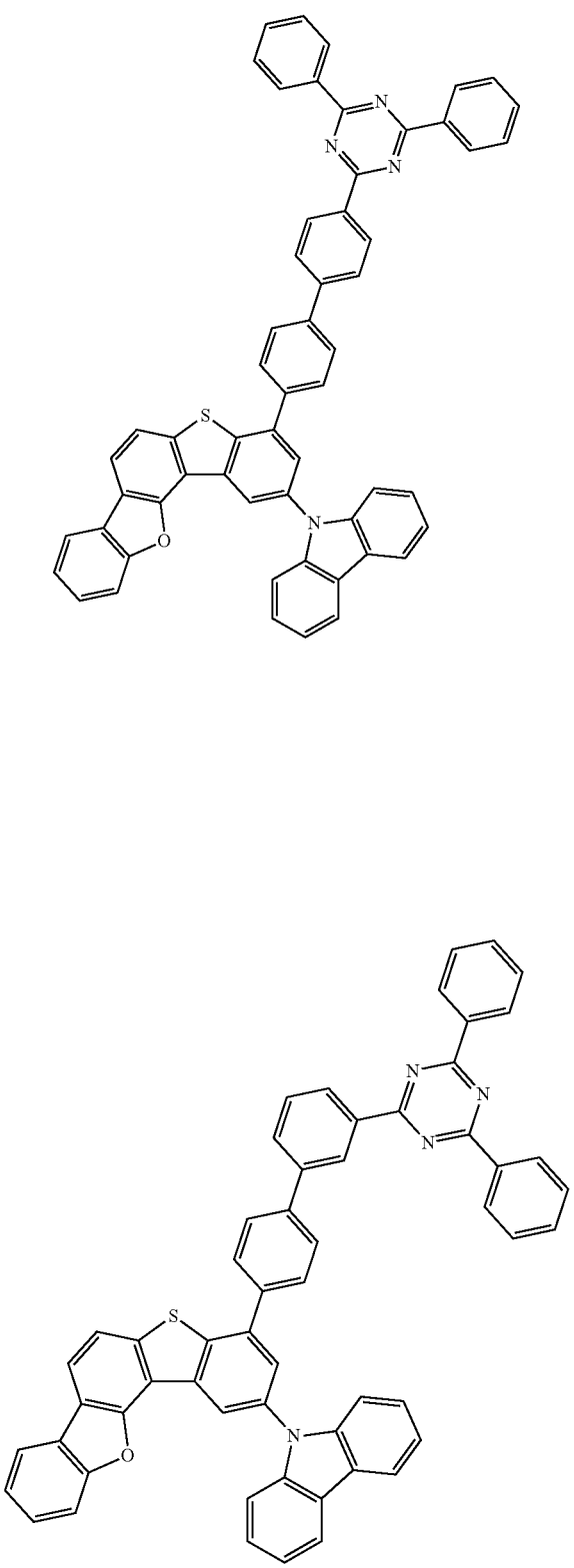

105
-continued
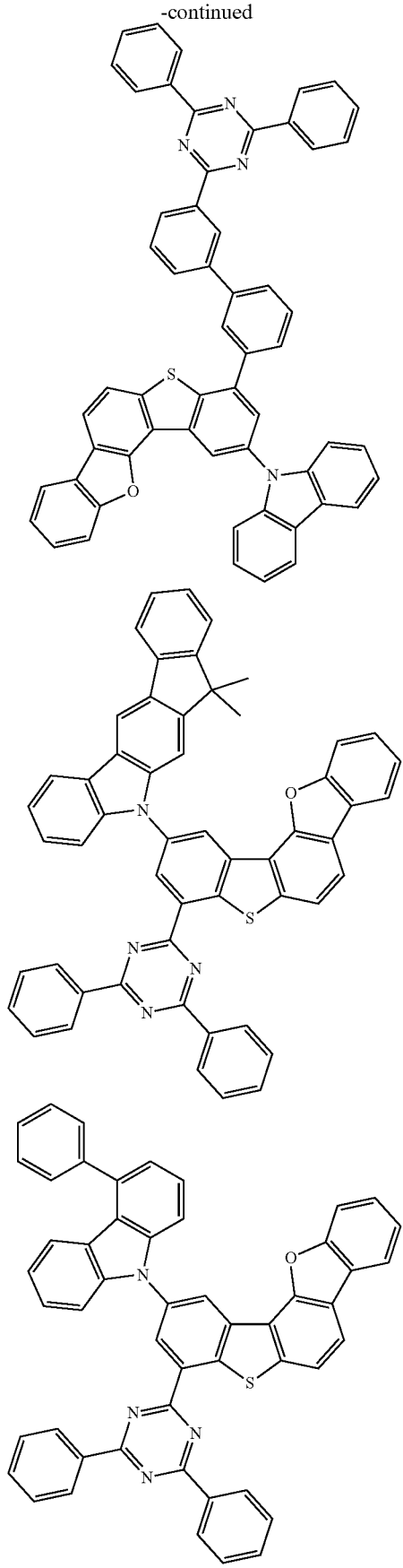
106
-continued
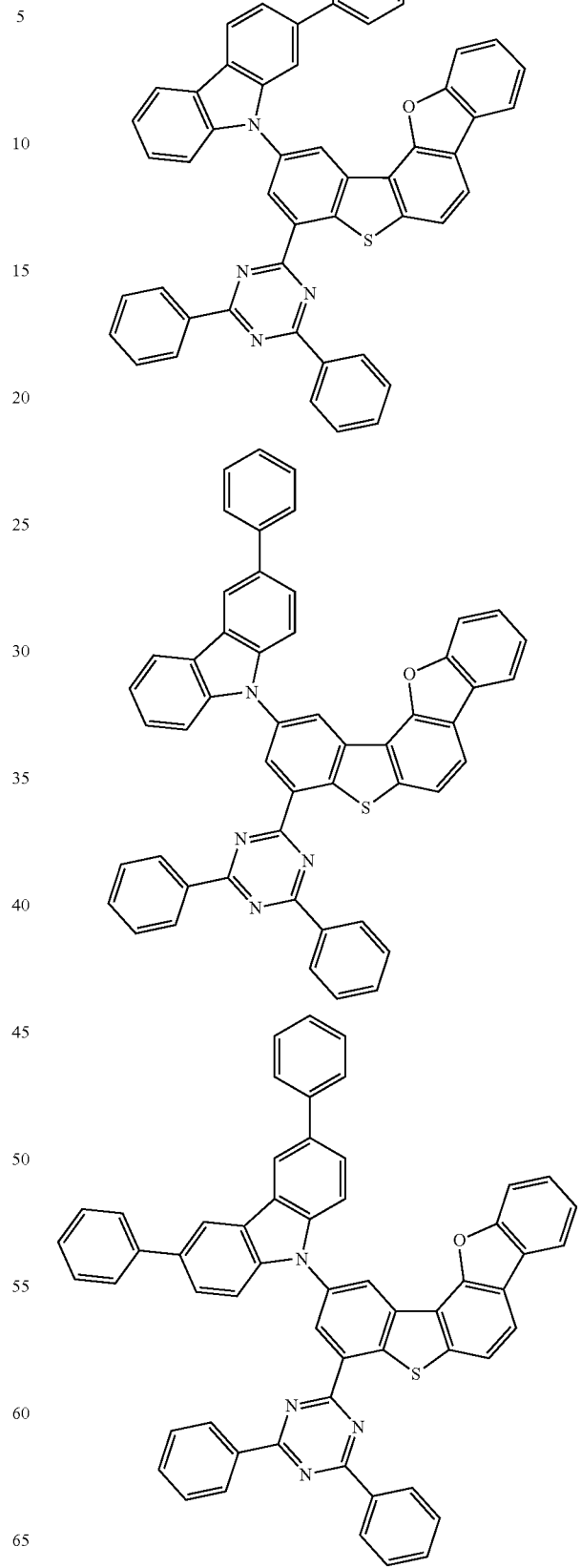

107
-continued
108
-continued
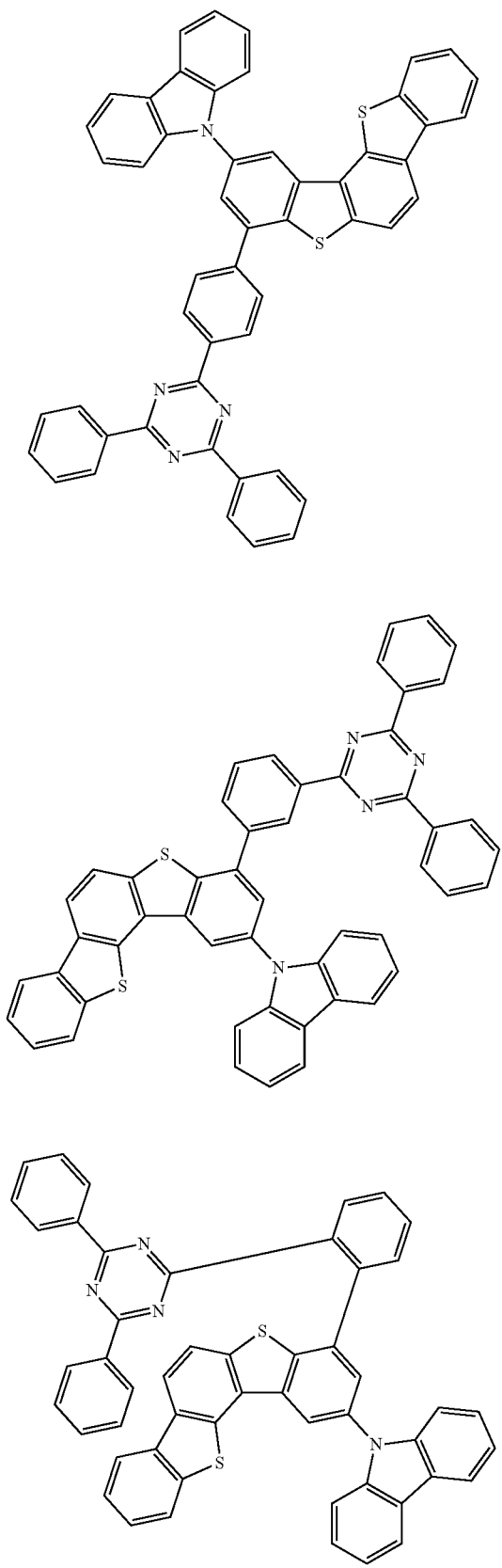 [SMILES: c1ccc(-c2nc(-c3ccccc3)nc(-c3ccc(-c4cc(-n5c6ccccc6c6ccccc65)cc5c4sc4ccc6c7ccccc7sc6c45)cc3)n2)cc1 ; c1ccc(-c2nc(-c3ccccc3)nc(-c3cccc(-c4cc(-n5c6ccccc6c6ccccc65)cc5c4sc4ccc6c7ccccc7sc6c45)c3)n2)cc1 ; c1ccc(-c2nc(-c3ccccc3)nc(-c3ccccc3-c3cc(-n4c5ccccc5c5ccccc54)cc4c3sc3ccc5c6ccccc6sc5c34)n2)cc1]
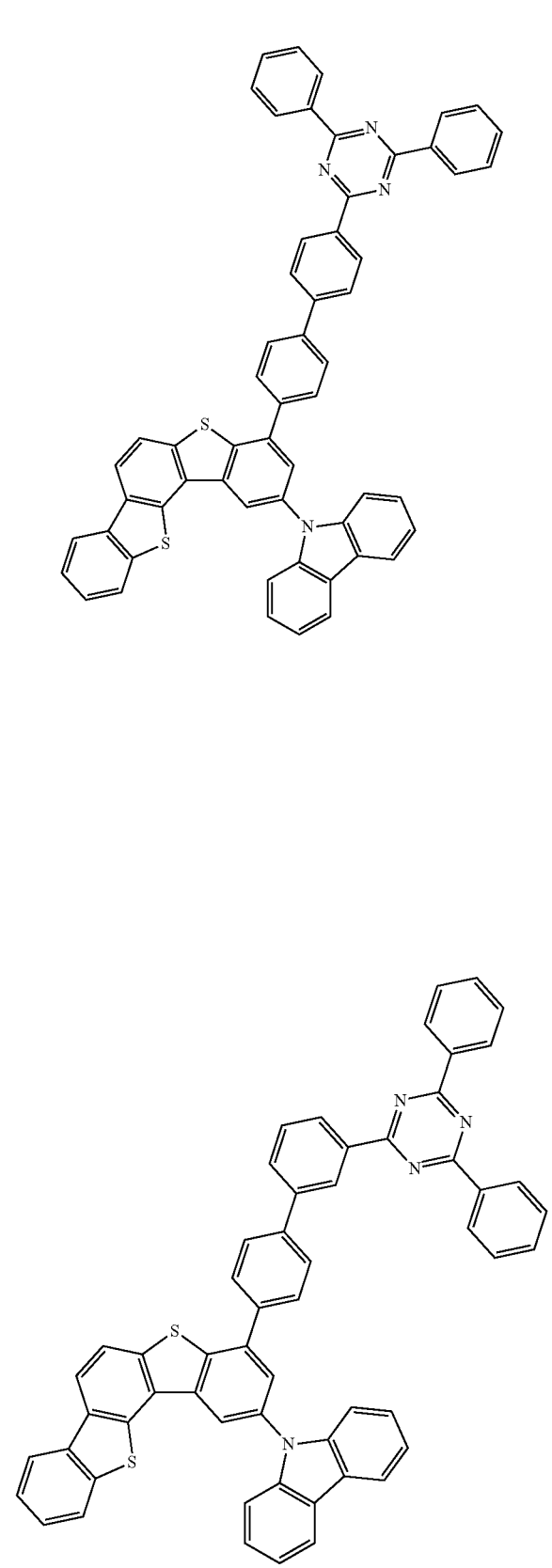

-continued
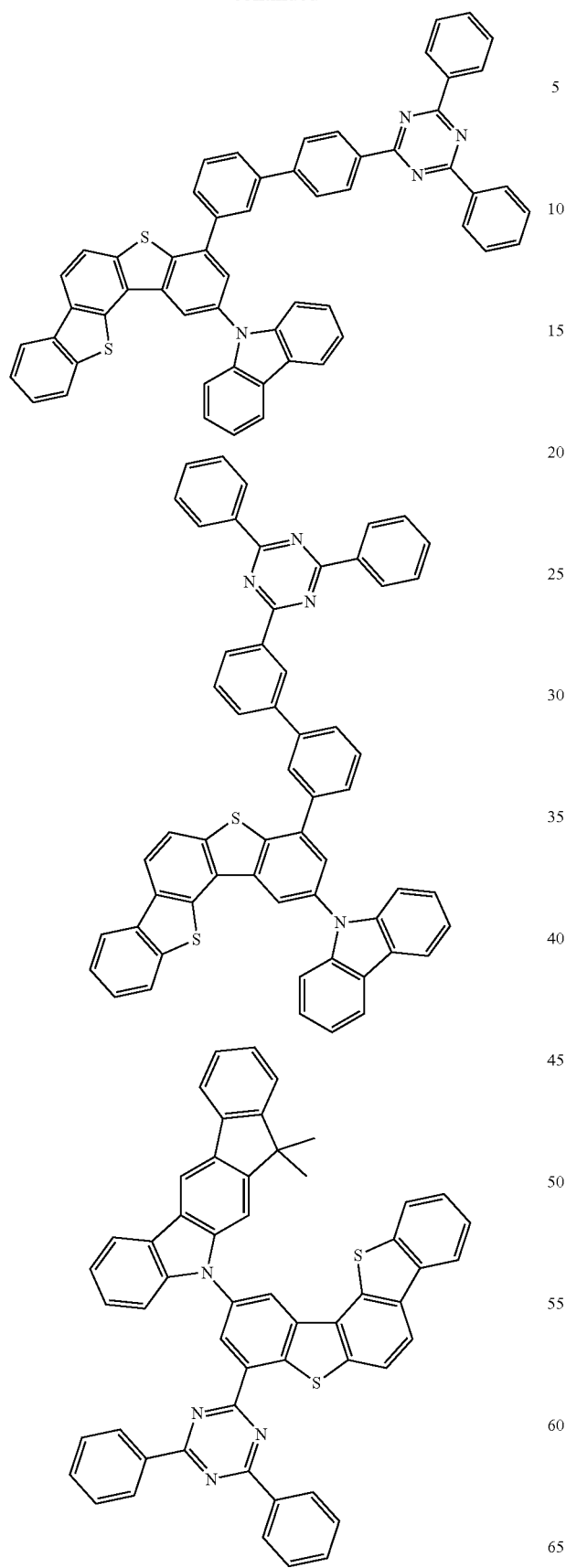
-continued
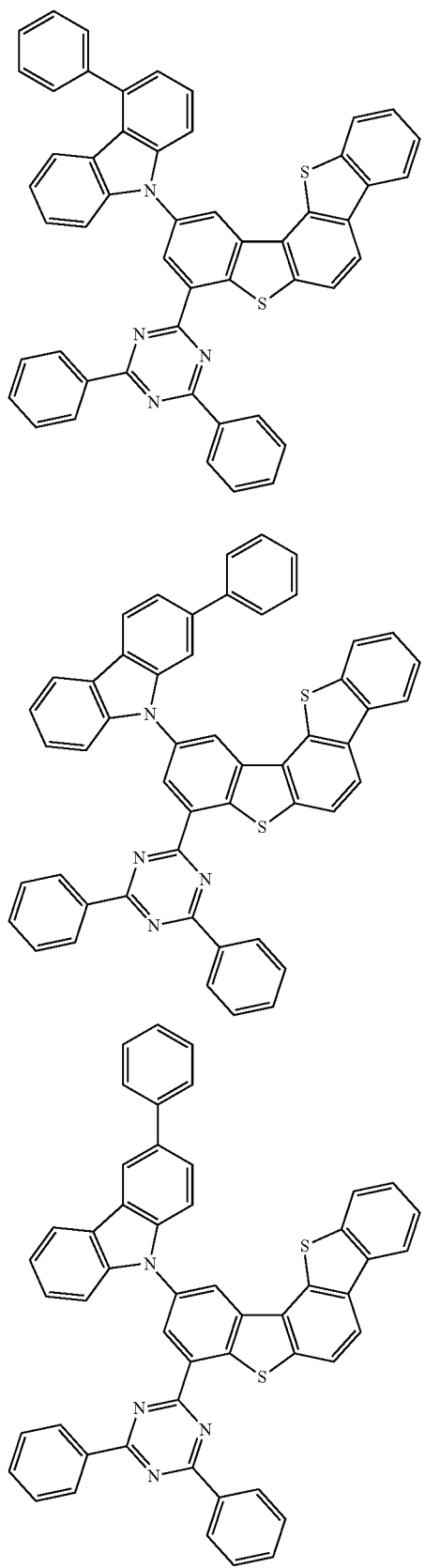

-continued
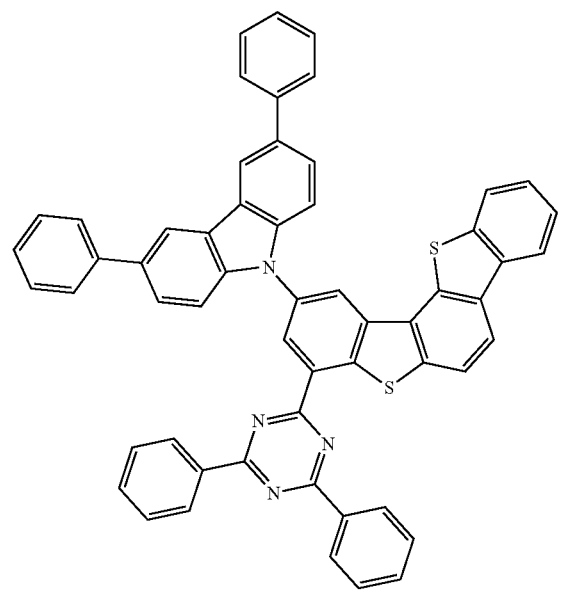
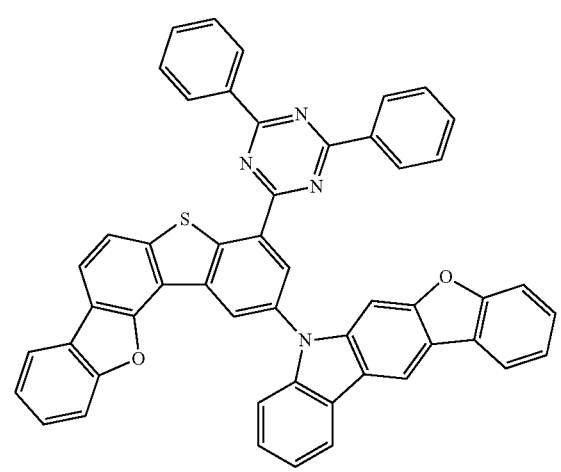
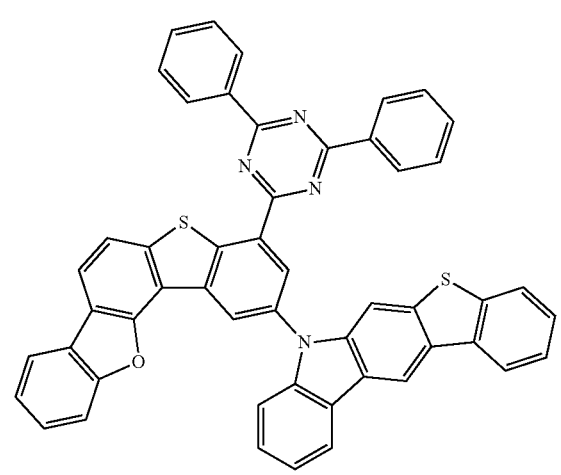
-continued
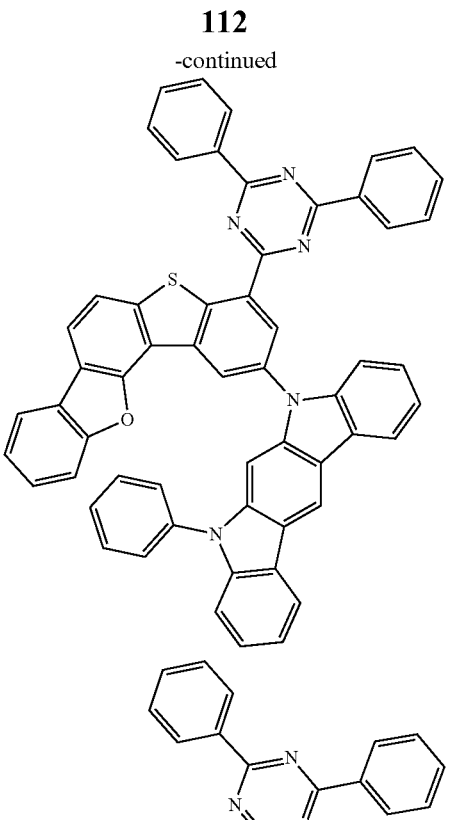
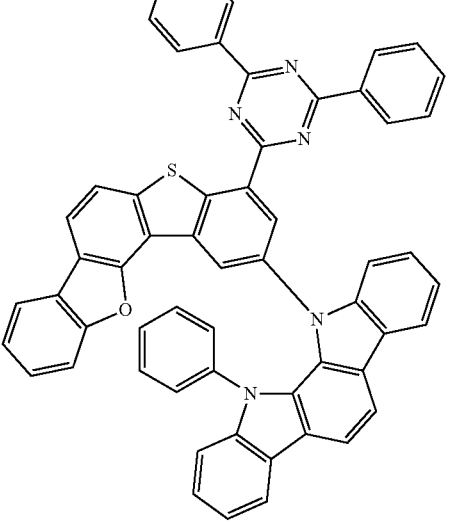
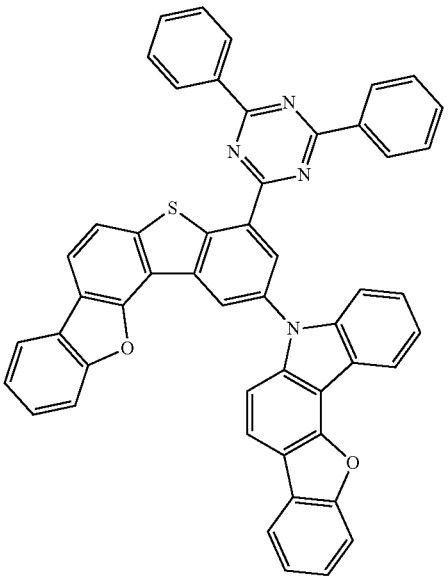

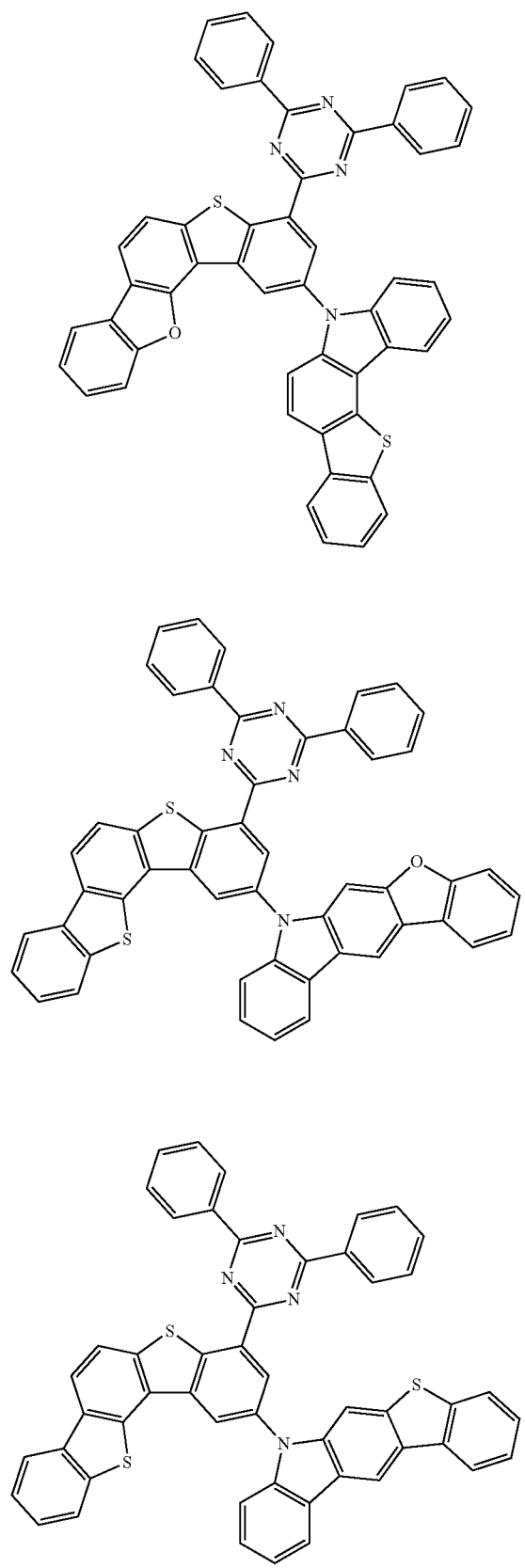
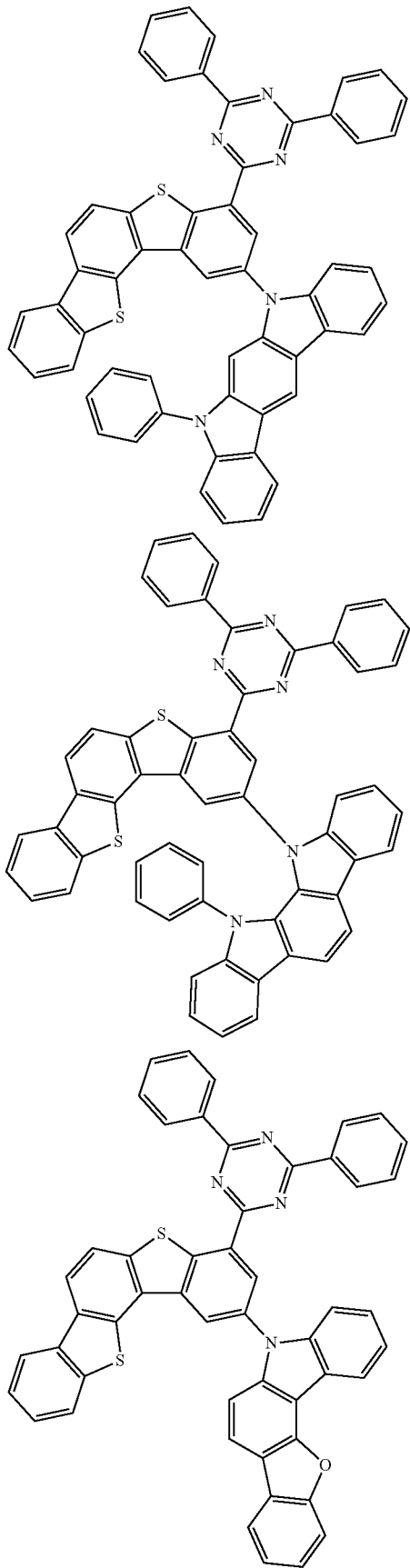

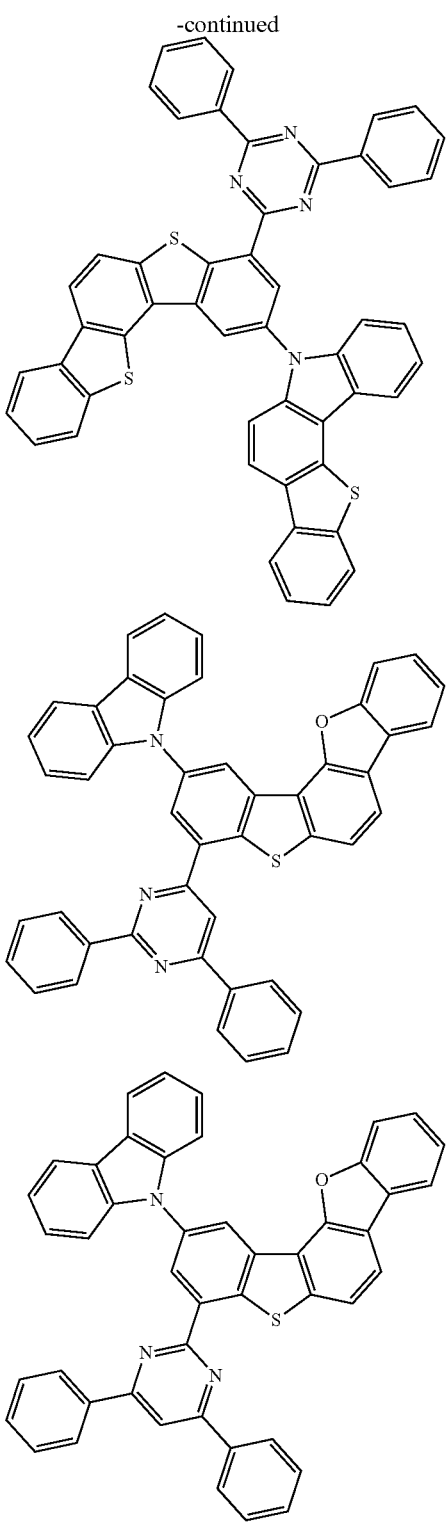
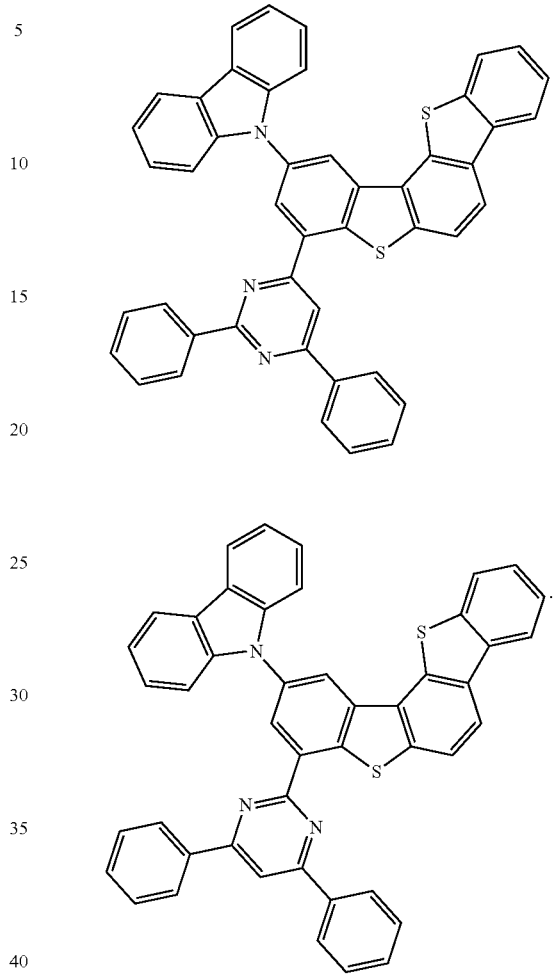

9. An organic light emitting device comprising: a first electrode; a second electrode provided opposite to the first electrode; and one or more organic material layers provided between the first electrode and the second electrode, wherein one or more layers of the organic material layers comprise the compound of claim 1.

10. The organic light emitting device according to claim 9, wherein:

the one or more organic material layers include a light emitting layer;

the light emitting layer includes two or more kinds of hosts; and one of the hosts is the compound.

* * * * *

UNITED STATES PATENT AND TRADEMARK OFFICE
CERTIFICATE OF CORRECTION

PATENT NO. : 11,680,071 B2
APPLICATION NO. : 17/055706
DATED : June 20, 2023
INVENTOR(S) : Min Woo Jung et al.

It is certified that error appears in the above-identified patent and that said Letters Patent is hereby corrected as shown below:

In the Claims

In Claim 1, at Column 83, the text at Lines 7-17 should read as follows:
—R and $R_1$ to $R_8$ are each independently hydrogen, deuterium, a halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{2-60}$ heteroaryl containing one or more heteroatoms selected from the group consisting of N, O, and S;—

In Claim 5, at Column 87, the compound at Lines 33-43 should appear as follows:

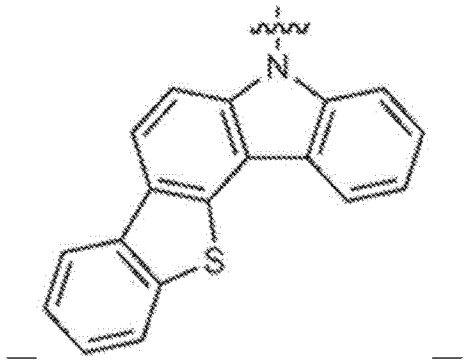

In Claim 7, at Column 89, the text at Lines 19-20 should read as follows:
—$X_1$ to $X_3$, Y, A, $Ar_1$, and $Ar_2$ are the same as defined in claim 1; and—

Signed and Sealed this
Thirtieth Day of January, 2024

Katherine Kelly Vidal
*Director of the United States Patent and Trademark Office*